United States Patent
Charati et al.

(10) Patent No.: US 11,613,581 B2
(45) Date of Patent: Mar. 28, 2023

(54) ANTIBODIES AND ANTIBODY-DRUG CONJUGATES SPECIFIC FOR CD123 AND USES THEREOF

(71) Applicant: Pfizer Inc., New York, NY (US)

(72) Inventors: Manoj Baburao Charati, Mahwah, NJ (US); Yoon-Chi Han, New York, NY (US); Madan Katragadda, Acton, MA (US); Nicole Melissa Piché-Nicholas, Waltham, MA (US); Lawrence Nathan Tumey, Vestal, NY (US)

(73) Assignee: Pfizer, Inc., New York, NY (US)

( * ) Notice: Subject to any disclaimer, the term of this patent is extended or adjusted under 35 U.S.C. 154(b) by 269 days.

(21) Appl. No.: 16/758,124

(22) PCT Filed: Oct. 16, 2018

(86) PCT No.: PCT/IB2018/058013
§ 371 (c)(1),
(2) Date: Apr. 22, 2020

(87) PCT Pub. No.: WO2019/082020
PCT Pub. Date: May 2, 2019

(65) Prior Publication Data
US 2020/0283536 A1 Sep. 10, 2020

Related U.S. Application Data

(60) Provisional application No. 62/577,922, filed on Oct. 27, 2017.

(51) Int. Cl.
*C07K 16/28* (2006.01)
*A61K 47/68* (2017.01)
(Continued)

(52) U.S. Cl.
CPC ...... *C07K 16/2866* (2013.01); *A61K 47/6803* (2017.08); *A61K 47/6851* (2017.08);
(Continued)

(58) Field of Classification Search
CPC ............ C07K 16/2866; C07K 2317/73; C07K 2317/76; A61K 47/6803; A61K 47/6851;
(Continued)

(56) References Cited

U.S. PATENT DOCUMENTS 3,773,919 A 11/1973 Boswell et al.
4,485,045 A 11/1984 Regen
(Continued)

FOREIGN PATENT DOCUMENTS

EP 3700929 A1 9/2020
WO 87/04462 A1 7/1987
(Continued)

OTHER PUBLICATIONS

Chailyan, A., et al (2011) The association of heavy and light chain variable domains in antibodies: implications for antigen specificity FEBS Journal 278; 2858-2866 (Year: 2011).*

(Continued)

*Primary Examiner* — Larry D Riggs, II
*Assistant Examiner* — Audrey L Buttice
(74) *Attorney, Agent, or Firm* — Saul Ewing LLP

(57) ABSTRACT

The present invention provides antibodies that specifically bind to CD123. The invention further relates to immunoconjugates (e.g., antibody-drug conjugates, or ADCs) comprising such antibodies, antibody encoding nucleic acids, and methods of obtaining such antibodies. The invention further relates to therapeutic methods for use of these antibodies and ADCs for the treatment of a condition
(Continued)

associated with cells expressing CD123 (e.g., cancer or autoimmune disease).

26 Claims, 3 Drawing Sheets

Specification includes a Sequence Listing.

(51) Int. Cl.
    *A61P 35/00*     (2006.01)
    *C12N 15/63*     (2006.01)
    *A61K 39/00*     (2006.01)

(52) U.S. Cl.
    CPC .............. *A61P 35/00* (2018.01); *C12N 15/63* (2013.01); *A61K 2039/505* (2013.01)

(58) Field of Classification Search
    CPC ... A61K 2039/505; A61P 35/00; C12N 15/63; C07F 9/65586; C07F 9/6561
    See application file for complete search history.

(56) References Cited

U.S. PATENT DOCUMENTS

| | | | |
|---|---|---|---|
| 4,544,545 A | 10/1985 | Ryan et al. | |
| 4,683,195 A | 7/1987 | Mullis et al. | |
| 4,683,202 A | 7/1987 | Mullis | |
| 4,754,065 A | 6/1988 | Levenson et al. | |
| 4,800,159 A | 1/1989 | Mullis et al. | |
| 5,013,556 A | 5/1991 | Woodle et al. | |
| 5,663,149 A | 9/1997 | Pettit et al. | |
| 5,981,568 A | 11/1999 | Kunz et al. | |
| 2009/0252742 A1 | 10/2009 | Bergstein | |
| 2013/0129753 A1 | 5/2013 | Doroski et al. | |
| 2017/0043033 A1 | 2/2017 | Strop et al. | |
| 2020/0283536 A1 | 9/2020 | Charati et al. | |

FOREIGN PATENT DOCUMENTS

| | | | | |
|---|---|---|---|---|
| WO | 99/58572 A1 | 11/1999 | | |
| WO | 00/53211 A2 | 9/2000 | | |
| WO | 2012/059882 A2 | 5/2012 | | |
| WO | 2012145493 A1 | 10/2012 | | |
| WO | 2015/015448 A2 | 2/2015 | | |
| WO | 2015/110935 A1 | 7/2015 | | |
| WO | WO-2016116626 A1 * | 7/2016 | .............. | A61P 35/00 |
| WO | 2016/201065 A1 | 12/2016 | | |
| WO | 2017/004026 A1 | 1/2017 | | |
| WO | WO-2019018525 A1 * | 1/2019 | .............. | A61K 35/17 |
| WO | 2019082020 A1 | 5/2019 | | |

OTHER PUBLICATIONS

Tang, Y., et al (2017) Real-Time Analysis on Drug-Antibody Ratio of Antibody-Drug Conjugates for Synthesis, Process Optimization, and Quality Control Scientific Reports 7(7763); 1-10 (Year: 2017).*
Aalberse et al, "IgG4 breaking the rules", Immunology 105(1):9-19 (2002).
Al-Lazikani et al, "Standard Conformations for the Canonical Structures of Immunoglobulins", J. Mol. Biol. 273:927-948 (1997).
Armour et al, "Recombinant human IgG molecules lacking Fcgamma receptor I binding and monocyte triggering activities", Eur. J. Immunol. 29:2613-2624 (1999).
Armour et al, "Differential binding to human FcgammaRIIa and FcgammaRIIb receptors by human IgG wildtype and mutant antibodies", Molecular Immunology 40(9):585-593 (2003).
Boger et al, "CC-1065 and the duocarmycins: Unraveling the keys to a new class of naturally derived DNA alkylating agents", Proc. Natl. Acad. Sci., USA 92:3642-3649 (1995).
Chothia et al, "Conformations of immunoglobulin hypervariable regions", Nature 342:877-883 (1989).
Eppstein et al, "Biological activity of liposome-encapsulated murine interferon gamma is mediated by a cell membrane receptor", Proc. Natl. Acad. Sci., USA 82:3688-3692 (1985).
Fellouse et al, "High-throughput Generation of Synthetic Antibodies from Highly Functional Minimalist Phage-displayed Libraries", J. Mol. Biol. 373(4):924-940 (2007).
Gentle et al, "Direct Production of Proteins with N-Terminal Cysteins for Site-Specific Conjugation", Bioconjugate Chem. 15:658-663 (2004).
Han et al, "Abstract 935: Generation and preclinical characterization of CD123-CPI antibody-drug conjugate (ADC)", Cancer Research 78(Issue 13 Supplement):935 (2018).
Hwang et al, "Hepatic uptake and degradation of unilamellar sphingomyelin/cholesterol liposomes: A kinetic study", Proc. Natl. Acad. Sci., USA 77(7):4030-4034 (1980).
Jayasena, "Aptamers: An Emerging Class of Molecules That Rival Antibodies in Diagnostics", Clinical Chemistry 45(9):1628-1650 (1999).
Junutula et al, "Site-specific conjugation of a cytotoxic drug to an antibody improves the therapeutic index", Nature Biotechnology 26:925-932 (2008).
Li et al, "Design, synthesis and evaluation of anti-CD123 antibody drug conjugates", Bioorganic & Medicinal Chemistry 24(22):5855-5860 (2016).
Mac Callum et al, "Antibody-antigen Interactions: Contact Analysis and Binding Site Topography", J. Mol. Biol. 262:732-745 (1996).
Makabe et al., "Thermodynamic Consequences of Mutations in Vernier Zone Residues of a Humanized Anti-human Epidermal Growth Factor Receptor Murine Antibody, 528", The Journal of Biological Chemistry 283(2):1156-1166 (2008).
Myers et al, "Optimal alignments in linear space", Computer Applications in the Biosciences (CABIOS) 4(1):11-17 (1988).
Nicolaou et al, "Calicheamicin θI1: A Rationally Designed Molecule with Extremely Potent and Selective DNA Cleaving Properties and Apoptosis Inducing Activity", Angew. Chem. Int. Ed. Engl. 33(2):183-186 (1994).
PCT International Search Report and Written Opinion for PCT/IB2018/058013 dated Feb. 28, 2019.
Pettit et al, "Specific Activities of Dolastatin 10 and Peptide Derivatives against Cryptococcus neoformans", Antimicrobial Agents and Chemotherapy 42(11):2961-2965 (1998).
Remillard, "Antimitotic Activity of the Potent Tumor Inhibitor Maytansine", Science 189:1002-1005 (1975).
Saitou et al, "The Neighbor-joining Method: A New Method for Reconstructing Phylogenetic Trees", Molecular Biology Evolution 4(4):406-425 (1987).
Strop et al, "Location Matters: Site of Conjugation Modulates Stability and Pharmacokinetics of Antibody Drug Conjugates", Chemistry & Biology 20(2):161-167 (2013).
Tanaka et al, "N-terminal glycine-specific protein conjugation catalyzed by microbial transglutaminase", FEBS Letters 579(10):2092-2096 (2005).
Ward et al, "Binding activities of a repertoire of single immunoglobulin variable domains secreted from *Escherichia coli*", Nature 341:544-546 (1989).
Mariuzza, R. A. et al., "The Structural Basis of Antigen-Antibody Recognition," Annual Review of Biophysics and Biophysical Chemistry, (1987) 16:139-159.
Roitt I. et al.,"Immunologia," Moscow, Mir, (2000), Chap. 6, pp. 110-111.
Singer, M. et al., "Genes & Genomes, A Changing Perspective," Univ Science Books, (1991) : pp. 67-69.

* cited by examiner

ANTIBODIES AND ANTIBODY-DRUG CONJUGATES SPECIFIC FOR CD123 AND USES THEREOF

RELATED APPLICATIONS

This application is a § 371 national stage application of PCT International Application No. PCT/IB2018/058013, filed Oct. 16, 2018, which claims the benefit of U.S. Provisional Application No. 62/577,922, filed Oct. 27, 2017, which are incorporated by reference herein in their entirety.

REFERENCE TO SEQUENCE LISTING

This application is being filed electronically via EFS-Web and includes an electronically submitted sequence listing in .txt format. The .txt file contains a sequence listing entitled "PC72333_SEQ_LIST_ST25.txt" created on Oct. 27, 2017 and having a size of 78 KB. The sequence listing contained in this .txt file is part of the specification and is incorporated herein by reference in its entirety.

FIELD

The present invention relates to antibodies, e.g., full length antibodies which specifically bind to CD123. The invention further relates to conjugates (e.g., antibody-drug conjugates, or "ADCs") comprising the CD123 antibodies, compositions comprising the CD123 antibodies or their conjugates, and methods of using the CD123 antibodies or their conjugates for treating conditions associated with cells expressing CD123 (e.g., cancer).

BACKGROUND

CD123 is the alpha chain of the interleukin-3 receptor (IL-3Rα or IL3RAa) that forms a heterodimer with the common beta chain CD131 to help transmit the signal of IL-3. The biological role of IL-3 is to stimulate the survival and proliferation of multipotent cells. CD123 is believed to be involved in stimulating proliferation of acute myeloid leukemia (AML) cells and has a direct function in tumor biology. CD123 is frequently expressed on leukemic stem cells (LSCs), a cell population associated with relapse in patients. Among normal tissues, CD123 expression is mostly limited to hematopoietic cells, particularly plasmacytoid dendritic cells (pDC), which constitute <0.4% of peripheral blood mononuclear cells in human. As components of the innate immunity, pDCs produce large amount of type 1 interferons (IFN-α/β) in respond to viral and bacterial stimuli. Importantly, CD123 is not expressed on hematopoietic stem cells.

New cases of leukemia, lymphoma and myeloma are expected to account for 10.2 percent of the estimated 1,688,780 new cancer cases diagnosed in the US in 2017. CD123 is expressed on cancer cells in a variety of hematological malignancies including acute myeloid leukemia (AML) where its expression is >80%. Examples of blood cancer cells that express CD123 include blasts and leukemia stem cells. Diseases associated with the expression of CD123 include AML, myelodysplastic syndrome (MDS; low and high risk), acute lymphocytic leukemia (ALL, all subtypes), diffuse large B-cell lymphoma (DLBCL), chronic myeloid leukemia (CML), and blastic plasmacytoid dendritic cell neoplasm (BPDCN).

Currently, treatments for these diseases include over 50 individual drugs with others under study and in clinical trials. Radiation therapy is also commonly used to treat blood cancers and sometimes it is administered along with drug therapy. Immunotherapy, gene therapy and personalized medicine are also used. However, these therapies can have significant side effects and adverse reactions. Thus, there is a need for new and improved treatments for CD123 (IL-3Rα)-expressing blood cancers.

SUMMARY

The invention disclosed herein is directed to antibodies that bind to CD123, and conjugates, such as antibody-drug conjugates (ADCs), comprising antibodies that bind to CD123, and methods of preparing and using such antibodies and ADCs to treat disorders.

Provided herein are antibodies which specifically binds to CD123. In some embodiments, the invention provides an isolated antibody which specifically binds to CD123, wherein the antibody comprises: a heavy chain variable region (VH) comprising comprising three complementarity determining regions (CDRs) of a VH comprising the amino acid sequence of SEQ ID NO: 6, 24, 32, 44, 51, or 64, and a light chain variable region (VL) comprising three CDRs of a VL comprising the amino acid sequence of SEQ ID NO: 17, 28, 39, 48, 57, or 71. In some embodiments, the VH can comprise (i) a VH CDR1 comprising the amino acid sequence of SEQ ID NO: 7, 33, 52, or 65; (ii) a VH CDR2 comprising the amino acid sequence of SEQ ID NO: 8, 25, 34, 45, 53, or 66; and (iii) a VH CDR3 comprising the amino acid sequence of SEQ ID NO: 9, 35, 46, or 67. In some embodiments, the VL region can comprise (i) a VL CDR1 comprising the amino acid sequence of SEQ ID NO: 18, 40, 58, or 72; (ii) a VL CDR2 comprising the amino acid sequence of SEQ ID NO: 19, 42, 60, or 74; and (iii) a VL CDR3 comprising the amino acid sequence of SEQ ID NO: 20, 42, 60, or 74. In some embodiments, the VH can comprise (i) a VH CDR1 comprising the amino acid sequence of SEQ ID NO: 7; (ii) a VH CDR2 comprising the amino acid sequence of SEQ ID NO: 25; and (iii) a VH CDR3 comprising the amino acid sequence of SEQ ID NO: 9. In some embodiments, the VL can comprise (i) a VL CDR1 comprising the amino acid sequence of SEQ ID NO: 18; (ii) a VL CDR2 comprising the amino acid sequence of SEQ ID NO: 19; and (iii) a VL CDR3 comprising the amino acid sequence of SEQ ID NO: 20. In some embodiments, the VH can comprise the sequence shown in SEQ ID NO: 24 or a variant thereof with one or several conservative amino acid substitutions in residues that are not within a CDR and/or the VL can comprise the amino acid sequence shown in SEQ ID NO: 28 or a variant thereof with one or several amino acid substitutions in amino acids that are not within a CDR. In some embodiments, the antibody can comprise a light chain comprising the sequence shown in SEQ ID NO: 30 and a heavy chain comprising the sequence shown in SEQ ID NO: 27.

Also provided is an isolated antibody which specifically binds to CD123 and comprises a heavy chain variable region produced by the expression vector with ATCC Accession No. PTA-124283 and a light chain variable region produced by the expression vector with ATCC Accession No. PTA-124284.

Also provided are isolated antibodies which specifically bind to CD123 and compete for binding to CD123 with an antibody comprising a heavy chain variable region (VH) comprising three CDRs of a VH comprising the amino acid sequence of SEQ ID NOs: 6, 24, 32, 44, 51, or 64; and a VL comprising three CDRs of a VL comprising the amino acid sequence of SEQ ID NO: 17, 28, 39, 48, 57, or 71.

Also provided are isolated CD123 antibodies comprising a VH comprising the amino acid sequences of SEQ ID NOs: 7, 8, and 9 and a VL comprising the amino acid sequences of SEQ ID NOs: 18, 19, and 20.

Also provided are isolated CD123 antibodies comprising a VH comprising the amino acid sequences of SEQ ID NOs: 7, 25, and 9 and a VL comprising the amino acid sequences of SEQ ID NOs: 18, 19, and 20.

Also provided are isolated CD123 antibodies comprising a VH comprising the amino acid sequences of SEQ ID NOs: 33, 34, and 35 and a VL comprising the amino acid sequences of SEQ ID NOs: 40, 41, and 42.

Also provided are isolated CD123 antibodies comprising a VH comprising the amino acid sequences of SEQ ID NOs: 33, 45, and 46 and a VL comprising the amino acid sequences of SEQ ID NOs: 40, 41, and 42.

Also provided are isolated CD123 antibodies comprising a VH comprising the amino acid sequences of SEQ ID NOs: 52, 53, and 54 and a VL comprising the amino acid sequences of SEQ ID NOs: 58, 59, and 60.

Also provided are isolated CD123 antibodies comprising a VH comprising the amino acid sequences of SEQ ID NOs: 65, 66, and 67 and a VL comprising the amino acid sequences of SEQ ID NOs: 72, 73, and 74.

In some embodiments, the CD123 antibodies as described herein can comprise an acyl donor glutamine-containing tag engineered at a specific site. In some embodiments, the tag can comprise an amino acid sequence selected from the group consisting of Q, LQG, LLQGG (SEQ ID NO:77), LLQG (SEQ ID NO:78), LSLSQG (SEQ ID NO: 79), GGGLLQGG (SEQ ID NO: 80), GLLQG (SEQ ID NO: 81), LLQ, GSPLAQSHGG (SEQ ID NO: 82), GLLQGGG (SEQ ID NO: 83), GLLQGG (SEQ ID NO: 84), GLLQ (SEQ ID NO: 85), LLQLLQGA (SEQ ID NO: 86), LLQGA (SEQ ID NO: 87), LLQYQGA (SEQ ID NO: 88), LLQGSG (SEQ ID NO: 89), LLQYQG (SEQ ID NO: 90), LLQLLQG (SEQ ID NO: 91), SLLQG (SEQ ID NO: 92), LLQLQ (SEQ ID NO: 93), LLQLLQ (SEQ ID NO: 94), LLQGR (SEQ ID NO: 95), LLQGPP (SEQ ID NO: 96), LLQGPA (SEQ ID NO: 97), GGLLQGPP (SEQ ID NO: 98), GGLLQGA (SEQ ID NO: 99), LLQGPGK (SEQ ID NO: 100), LLQGPG (SEQ ID NO: 101), LLQGP (SEQ ID NO: 102), LLQGP (SEQ ID NO: 103), LLQPGK (SEQ ID NO: 104), LLQAPGK (SEQ ID NO: 105), LLQGAPG (SEQ ID NO: 106), LLQGAP (SEQ ID NO: 107), and LLQLQG (SEQ ID NO: 108). In some embodiments, the glutamine-containing tag is LLQG (SEQ ID NO: 78).

In some embodiments, the CD123 antibodies as described herein can comprise an amino acid modification at position 222, 340, or 370. In some embodiments, the amino acid modification can be a substitution from lysine to arginine. In some embodiments, the amino acid modification can be K222R.

In some embodiments, the CD123 antibodies as described herein can comprise a linker. In some embodiments, the linker can be cleavable. In some embodiments, the linker can be selected from the group consisting of Ac-Lys-Gly (acetyl-lysine-glycine), aminocaproic acid, Ac-Lys-β-Ala (acetyl-lysine-β-alanine), amino-PEG2 (polyethylene glycol)-C2, amino-PEG3-C2, amino-PEG6-C2, Ac-Lys-Val-Cit-PABC (acetyl-lysine-valine-citrulline-p-aminobenzyloxycarbonyl), amino-PEG6-C2-Val-Cit-PABC, aminocaproyl-Val-Cit-PABC, [(3R,5R)-1-{3-[2-(2-amino-ethoxy)ethoxy]propanoyl}piperidine-3,5-diyl]bis-Val-Cit-PABC, [(3S,5S)-1-{3-[2-(2-aminoethoxy)ethoxy]propanoyl}piperidine-3,5-diyl]bis-Val-Cit-PABC, putrescine, and Ac-Lys-putrescine. In some embodiments, the linker can be Ac-Lys-Val-Cit-PABC (acetyl-lysine-valine-citrulline-p-aminobenzyloxycarbonyl).

In some embodiments, the antibody as described herein comprises a constant region. In some embodiments, the antibody is a humanized antibody. In some embodiments, the antibody is of the human IgG1, IgG2 or IgG2Δa, IgG3, or IgG4 subclass. In some embodiments, the antibody is an IgG1 antibody. In some embodiments, the antibody comprises a N60G mutation.

Also provided are conjugates that comprise a CD123 antibody as described herein conjugated to an agent. In some embodiments, the agent can be selected from the group consisting of a cytotoxic agent, an immunomodulating agent, an imaging agent, a therapeutic protein, a biopolymer, and an oligonucleotide. In some embodiments, the agent can be a cytotoxic agent. In some embodiments, the cytotoxic agent can be selected from the group consisting of an anthracycline, an auristatin, a camptothecin, a combretastatin, a CBI dimer, a cyclopropylpyrroloindoline (CPI) dimer, a CTI dimer, a dolastatin, a duocarmycin, an enediyne, a geldanamycin, an indolino-benzodiazepine dimer, a maytansine, a puromycin, a pyrrolobenzodiazepine dimer, a taxane, a vinca alkaloid, a tubulysin, a hemiasterlin, a spliceostatin, a pladienolide, and stereoisomers, isosteres, analogs, or derivatives thereof. In some embodiments, the cytotoxic agent can be a CPI dimer. In some embodiments, the CPI dimer is CPI-8314. In some embodiments, the CPI dimer can have the following structure:

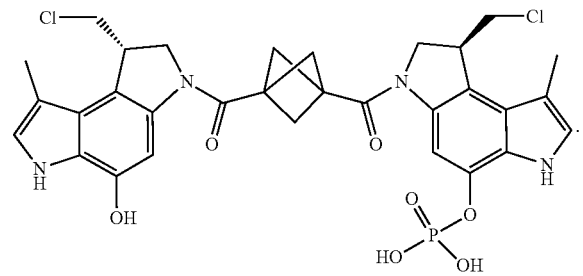 [SMILES: Cc1c[nH]c2c(O)cc3c(c12)[C@H](CCl)CN3C(=O)C12CC(C(=O)N3C[C@@H](CCl)c4c3cc(OP(=O)(O)O)c3[nH]cc(C)c43)(C1)C2]

In some embodiments, the cytotoxic agent can have the IUPAC name: (8S)-8-(chloromethyl)-6-[(3-{[(1S)-1-(chloromethyl)-5-hydroxy-8-methyl-1,6-dihydropyrrolo[3,2-e]indol-3(2H)-yl]carbonyl}bicyclo[1.1.1]pent-1-yl)carbonyl]-1-methyl-3,6,7,8-tetrahydropyrrolo[3,2-e]indol-4-yl dihydrogen phosphate. In some embodiments, the cytotoxic agent can be C31H31Cl2N4O7P, or a pharmaceutically acceptable salt or solvate. In some embodiments, the cytotoxic agent can be in trifluoroacetic acid (TFA) salt form: C31H31Cl2N4O7P.C2HF3O2.

In other embodiments, the cytotoxic agent can be MMAD (Monomethyl Auristatin D), 0101 (2-methylalanyl-N-[(3R, 4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide), 3377 (N,2-dimethylalanyl-N-{(1S,2R)-4-{(2S)-2-[(1R,2R)-3-{[(1S)-1-carboxyl-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide), 0131 (2-methyl-L-proly-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1- oxoheptan-4-yl]-N-methyl-L-valinamide), or 0121 (2-methyl-L-proly-N-[(3R,4S,5S)-1-{(2S)-2-[(1R,2R)-3-{[(2S)-1-methoxy-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide).

In some embodiments, the conjugate can comprise the formula: antibody-(acyl donor glutamine-containing tag)-(linker)-(cytotoxic agent). In some embodiments, the acyl donor glutamine-containing tag can comprise an amino acid sequence LLQG (SEQ ID NO: 78) and the linker can comprise acetyl-lysine-valine-citrulline-p-aminobenzyloxycarbonyl. In some embodiments, the acyl donor glutamine-containing tag can be inserted in the antibody at position E294-N297. In some embodiments, the conjugate can further comprise an amino acid substitution from lysine to arginine at antibody position 222, according to the numbering of the EU index of Kabat (K222R).

Also provided are pharmaceutical compositions comprising a therapeutically effective amount of a CD123 antibody described herein, or a CD123 ADC described herein, and a pharmaceutically acceptable carrier.

Also provided are isolated polynucleotides comprising a nucleotide sequence encoding a CD123 antibody described herein. Also provided are vectors comprises such polynucleotides.

Also provided are isolated host cells that recombinantly produce any of the CD123 antibodies described herein. Also provided are methods of producing an antibody, comprising culturing such host cells under conditions that result in production of the antibody, and isolating the antibody from the host cells or culture.

Also provided are methods of treating a condition associated with cells expressing CD123 in a subject comprising administering to a subject in need thereof a therapeutically effective amount of a pharmaceutical composition comprising any of the CD123 antibodies described herein, or the conjugate of any of the antibodies, and a pharmaceutically acceptable carrier. In some embodiments, the condition is cancer. In some embodiments, the cancer can be a cancer selected from the group consisting of acute myeloid leukemia (AML), acute lymphocytic leukemia (ALL), Blastic Plasmacytoid Dendritic Cell Neoplasm (BPDCN), hairy cell leukemia, B-cell non-Hodgkin's lymphoma (NHL), multiple myeloma, malignant plasma cell neoplasm, Hodgkin's lymphoma, nodular lymphocyte predominant Hodgkin's lymphoma, Kahler's disease and Myelomatosis, plasma cell leukemia, plasmacytoma, B-cell prolymphocytic leukemia, chronic lymphocytic leukemia (CLL), chronic myeloid leukemia (CML), follicular lymphoma, Burkitt's lymphoma, marginal zone lymphoma, mantle cell lymphoma, large cell lymphoma, precursor B-lymphoblastic lymphoma, myeloid leukemia, Waldenstrom's macroglobulienemia, diffuse large B cell lymphoma, follicular lymphoma, marginal zone lymphoma, mucosa-associated lymphatic tissue lymphoma, small cell lymphocytic lymphoma, mantle cell lymphoma, Burkitt lymphoma, primary mediastinal (thymic) large B-cell lymphoma, lymphoplasmactyic lymphoma, Waldenstrom macroglobulinemia, nodal marginal zone B cell lymphoma, splenic marginal zone lymphoma, intravascular large B-cell lymphoma, primary effusion lymphoma, lymphomatoid granulomatosis, T cell/histiocyte-rich large B-cell lymphoma, primary central nervous system lymphoma, primary cutaneous diffuse large B-cell lymphoma (leg type), EBV positive diffuse large B-cell lymphoma of the elderly, diffuse large B-cell lymphoma associated with inflammation, intravascular large B-cell lymphoma, ALK-positive large B-cell lymphoma, plasmablastic lymphoma, large B-cell lymphoma arising in HHV8-associated multicentric Castleman disease, B-cell lymphoma unclassified with features intermediate between diffuse large B-cell lymphoma and Burkitt lymphoma, B-cell lymphoma unclassified with features intermediate between diffuse large B-cell lymphoma and classical Hodgkin lymphoma, and other B-cell related lymphoma. In some embodiments, the cancer is AML.

Also provided are methods of inhibiting tumor growth or progression in a subject who has malignant cells expressing CD123, comprising administering to the subject in need thereof a therapeutically effective amount of a pharmaceutical composition comprising any of the CD123 antibodies provided herein, or the conjugate of any of the antibodies, and a pharmaceutically acceptable carrier.

Also provided are methods of inhibiting metastasis of malignant cells expressing CD123 in a subject, comprising administering to the subject in need thereof a therapeutically effective amount of a pharmaceutical composition comprising any of the CD123 antibodies provided herein, or the conjugate of any of the antibodies, and a pharmaceutically acceptable carrier.

Also provided are methods of inducing tumor regression in a subject who has malignant cells expressing CD123, comprising administering to the subject in need thereof a therapeutically effective amount of a pharmaceutical composition comprising any of the CD123 antibodies provided herein, or the conjugate of any of the antibodies, and a pharmaceutically acceptable carrier.

In another aspect, the invention provides an effective amount of a composition (e.g., pharmaceutical composition) comprising the CD123 antibodies or the CD123 ADCs as described herein for treating a condition (e.g., cancer or autoimmune disorder) associated with CD123 expression in a subject in need thereof. In some embodiments, an effective amount of a composition (e.g., pharmaceutical composition) comprises the CD123 antibodies or the CD123 ADCs as described herein for inhibiting tumor growth or progression in a subject who has malignant cells expressing CD123. In some embodiments, provided is an effective amount of a composition (e.g., pharmaceutical composition) comprising the CD123 antibodies or the CD123 ADCs as described herein for inhibiting metastasis of malignant cells expressing CD123 in a subject in need thereof. In some embodiments, an effective amount of a composition (e.g., pharmaceutical composition) comprises the CD123 antibodies or the CD123 ADCs as described herein for inducing tumor regression in a subject who has malignant cells expressing CD123.

In another aspect, the invention provides the CD123 antibodies or the CD123 ADCs as described herein for use in treating a condition (e.g., cancer or autoimmune disorder) associated with CD123 expression in a subject in need thereof. In some embodiments, provided are the CD123 antibodies or the CD123 ADCs as described herein for inhibiting tumor growth or progression in a subject who has malignant cells expressing CD123. In some embodiments, provided is the CD123 antibodies or the CD123 ADCs as described herein for inhibiting metastasis of malignant cells expressing CD123 in a subject in need thereof. In some embodiments, provided is the CD123 antibodies or the CD123 ADCs as described herein for inducing tumor regression in a subject who has malignant cells expressing CD123.

In another aspect, the invention provides a use of the CD123 antibodies or the CD123 ADCs as described herein in the manufacture of a medicament for treating a condition (e.g., cancer or autoimmune disorder) associated with CD123 expression. In some embodiments, provided is a use of the CD123 antibodies or the CD123 ADCs as described herein in the manufacture of a medicament for inhibiting tumor growth or progression. In some embodiments, provided is a use of the CD123 antibodies or the CD123 ADCs as described herein in the manufacture of a medicament for inhibiting metastasis of malignant cells expressing CD123. In some embodiments, provided is a use of the CD123 antibodies or the CD123 ADCs as described herein in the manufacture of a medicament for inducing tumor regression.

Also provided herein are methods for conjugating an antibody to AcLysValCitPABC-DMAE-CO_CPI-000638314 (AcLysPABC-CPI-8314). In some embodiments, the method comprises preparing a composition comprising an antibody and AcLysPABC-CPI-8314 in a buffer comprising 30 to 100 mM KPO4 and 150 to 200 mM NaCl; adding bacterial tranglutaminase to the composition; and incubating the composition to allow conjugation of the antibody to the AcLysPABC-CPI-8314. In some embodiments, the pH of the composition is 7. In some embodiments, the composition comprises 0.5 to 2 units (U) of bacterial transglutaminase per mg of antibody. In some embodiments, the composition comprises 1 U of bacterial transglutaminase per mg of antibody. In some embodiments, the AcLysPABC-CPI-8314 is present in a 10-fold molar excess to the antibody. In some embodiments, the composition is incubated at 25° C. overnight with continuous mixing. In some embodiments, the composition further comprises 7.5% (v/v) of dimethyl sulfoxide (DMSO). In some embodiments, the buffer comprises 30 mM KPO4 and 150 mM NaCl. In some embodiments, the buffer comprises 100 mM KPO4 and 200 mM NaCl. In some embodiments, the antibody is an anti-tumor antibody. In some embodiments, the anti-tumor antibody is a CD123 antibody.

BRIEF DESCRIPTION OF THE FIGURES/DRAWINGS

DETAILED DESCRIPTION

Figure 1:
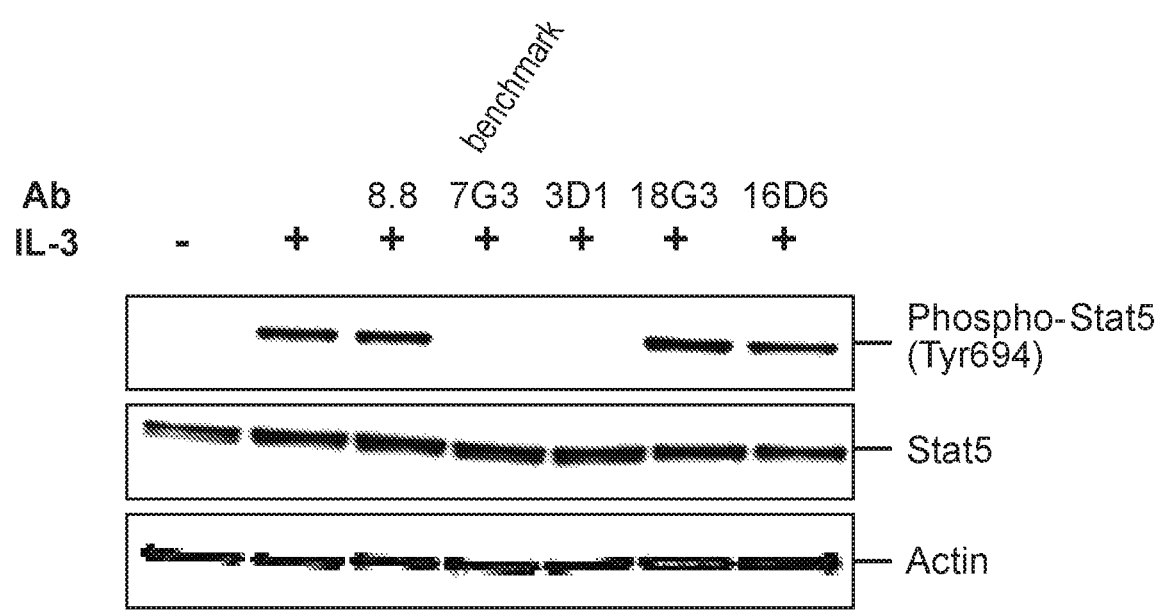
FIG. 1 depicts Western blot results from analysis of cells treated with IL-3 plus antibodies ("Ab"). 7G3 is a benchmark antibody and, 3D1, 18G3, and 16D6 are CD123 antibodies; 8.8 is a negative control antibody that does not bind CD123. STAT5, phosphorylated STAT5, and actin levels were analyzed.

The invention disclosed herein provides antibodies and antibody-drug conjugates (ADCs) that specifically bind to CD123 (e.g., human CD123). The invention also provides polynucleotides encoding these antibodies, compositions comprising these antibodies, and methods of making and using these antibodies. The invention also provides methods for treating disorders associated with CD123 expression in a subject, such as cancer or autoimmune disease.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Definitions

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also antigen-binding fragments thereof (such as Fab, Fab', F(ab')$_2$, Fv), single chain (ScFv) and domain antibodies (including, for example, shark and camelid antibodies), and fusion proteins comprising an antibody, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

The term "antigen binding fragment" or "antigen binding portion" of an antibody, as used herein, refers to one or more fragments of an intact antibody that retain the ability to specifically bind to a given antigen (e.g., CD123). Antigen binding functions of an antibody can be performed by fragments of an intact antibody. Examples of binding fragments encompassed within the term "antigen binding fragment" of an antibody include Fab; Fab'; F(ab')$_2$; an Fd fragment consisting of the heavy chain variable region (VH) and CH1 domains; an Fv fragment consisting of the VL and VH domains of a single arm of an antibody; a single domain antibody (dAb) fragment (Ward et al., Nature 341:544-546, 1989), and an isolated complementarity determining region (CDR).

An antibody, an ADC, or a polypeptide that "preferentially binds" or "specifically binds" (used interchangeably herein) to a target (e.g., CD123 protein) is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a CD123 epitope is an antibody that binds this epitope with greater affinity, avidity, more readily, and/or with greater duration than it binds to other CD123 epitopes or non-CD123 epitopes. It is also understood that by reading this definition, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

A "variable region" of an antibody refers to the variable region of the antibody light chain or the variable region of the antibody heavy chain, either alone or in combination. As known in the art, the variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al., 1997, J. Molec. Biol. 273:927-948). As used herein, a CDR may refer to CDRs defined by either approach or by a combination of both approaches.

A "CDR" of a variable domain are amino acid residues within the variable region that are identified in accordance with the definitions of the Kabat, Chothia, the accumulation of both Kabat and Chothia, AbM, contact, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the structural loop structures originally described by Chothia and others. See, e.g., Chothia et al., Nature 342:877-883, 1989. Other approaches to CDR identification include the "AbM definition," which is a compromise between Kabat and Chothia and is derived using Oxford Molecular's AbM antibody modeling software (now Accelrys®), or the "contact definition" of CDRs based on observed antigen contacts, set forth in MacCallum et al., J. Mol. Biol., 262:732-745, 1996. In another approach, referred to herein as the "conformational definition" of CDRs, the positions of the CDRs may be identified as the residues that make enthalpic contributions to antigen binding. See, e.g., Makabe et al., Journal of Biological Chemistry, 283:1156-1166, 2008. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

The terms "polypeptide", "oligopeptide", "peptide" and "protein" are used interchangeably herein to refer to chains of amino acids of any length, preferably, relatively short (e.g., 10-100 amino acids). The chain may be linear or branched, it may comprise modified amino acids, and/or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains.

Antibodies of the invention can be produced using techniques well known in the art, e.g., recombinant technologies, phage display technologies, synthetic technologies or combinations of such technologies or other technologies readily known in the art (see, for example, Jayasena, S. D., Clin. Chem., 45: 1628-50, 1999 and Fellouse, F. A., et al, J. Mol. Biol., 373(4):924-40, 2007).

As known in the art, "polynucleotide," or "nucleic acid," as used interchangeably herein, refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. If present, modification to the nucleotide structure may be imparted before or after assembly of the chain. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha- or beta-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

As known in the art a "constant region" of an antibody refers to the constant region of the antibody light chain or the constant region of the antibody heavy chain, either alone or in combination.

As used herein, "substantially pure" refers to material which is at least 50% pure (i.e., free from contaminants), more preferably, at least 90% pure, more preferably, at least 95% pure, yet more preferably, at least 98% pure, and most preferably, at least 99% pure.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As known in the art, the term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. Kabat et al., Sequences of Proteins of Immunological Interest, 5th Ed. Public Health Service, National Institutes of Health, Bethesda, Md., 1991. The Fc region of an immunoglobulin generally comprises two constant regions, CH2 and CH3.

The term "compete", as used herein with regard to an antibody, means that a first antibody, or an antigen binding fragment (or portion) thereof, binds to an epitope in a manner sufficiently similar to the binding of a second antibody, or an antigen binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. In some embodiments, the variant Fc region has at least one amino acid substitution compared to a native sequence Fc region or to the Fc region of a parent polypeptide, e.g. from about one to about ten amino acid substitutions, and preferably, from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably, at least about 90% sequence identity therewith, more preferably, at least about 95%, at least about 96%, at least about 97%, at least about 98%, at least about 99% sequence identity therewith.

As used herein, the term "CD123" refers to any form of CD123 and variants thereof that retain at least part of the activity of CD123. Unless indicated differently, such as by specific reference to human CD123, CD123 includes all mammalian species of native sequence CD123, e.g., human, canine, feline, equine, and bovine. Exemplary CD123 sequences are shown in Table 1.

TABLE 1

| SEQ ID NO: | DESCRIPTION | SEQUENCE |
| --- | --- | --- |
| 1 | Human CD123, long isoform (Signal peptide underlined) | METDTLLLWVLLLWVPGSTG TKEDPNPPITNLRMKAKAQQLTWDLNRNVTDIECVKDADY SMPAVNNSYCQFGAISLCEVTNYTVRVANPPFSTWILFPE NSGKPWAGAENLTCWIHDVDFLSCSWAVGPGAPADVQY DLYLNVANRRQQYECLHYKTDAQGTRIGCRFDDISRLSSG SQSSHILVRGRSAAFGIPCTDKFVVFSQIEILTPPNMTAKCN KTHSFMHWKMRSHFNRKFRYELQIQKRMQPVITEQVRDR TSFQLLNPGTYTVQIRARERVYEFLSAWSTPQRFECDQEE GANTRAWRTSLLIALGTLLALVCVFVICRRYLVMQRLFPRIP HMKDPIGDSFQNDKLVVWEAGKAGLEECLVTEVQVVQKT |

TABLE 1-continued

| SEQ ID NO: | DESCRIPTION | SEQUENCE |
|---|---|---|
| 2 | Human CD123, long isoform ECD with Flag and Avi tags (Signal peptide and tags underlined) | METDTLLLWVLLLWVPGSTG TKEDPNPPITNLRMKAKAQQLTWDLNRNVTDIECVKDADY SMPAVNNSYCQFGAISLCEVTNYTVRVANPPFSTWILFPE NSGKPWAGAENLTCWIHDVDFLSCSWAVGPGAPADVQY DLYLNVANRRQQYECLHYKTDAQGTRIGCRFDDISRLSSG SQSSHILVRGRSAAFGIPCTDKFVVFSQIEILTPPNMTAKCN KTHSFMHWKMRSHFNRKFRYELQIQKRMQPVITEQVRDR TSFQLLNPGTYTVQIRARERVYEFLSAWSTPQRFECDQEE GANTRAWR GGPPDYKDDDDKGGGLNDIFEAQKIEWHE |
| 3 | Human CD123, short isoform (Signal peptide underlined) | METDTLLLWVLLLWVPGSTG TKEGKPWAGAENLTCWIHDVDFLSCSWAVGPGAPADVQY DLYLNVANRRQQYECLHYKTDAQGTRIGCRFDDISRLSSG SQSSHILVRGRSAAFGIPCTDKFVVFSQIEILTPPNMTAKCN KTHSFMHWKMRSHFNRKFRYELQIQKRMQPVITEQVRDR TSFQLLNPGTYTVQIRARERVYEFLSAWSTPQRFECDQEE GANTRAWRTSLLIALGTLLALVCVFVICRRYLVMQRLFPRIP HMKDPIGDSFQNDKLVVWEAGKAGLEECLVTEVQVVQKT |
| 4 | Cynomolgus CD123, ECD with Flag and Avi tags (Signal peptide and tags underlined) | METDTLLLWVLLLWVPGSTGQ TKEDPNAPIRNLRMKEKAQQLMWDLNRNVTDVECIKGTDY SMPAMNNSYCQFGAISLCEVTNYTVRVASPPFSTWILFPE NSGTPRAGAENLTCWVHDVDFLSCSWVVGPAAPADVQY DLYLNNPNSHEQYRCLHYKTDARGTQIGCRFDDIARLSRG SQSSHILVRGRSAAVSIPCTDKFVFFSQIERLTPPNMTGEC NETHSFMHWKMKSHFNRKFRYELRIQKRMQPVRTEQVRD TTSFQLPNPGTYTVQIRARETVYEFLSAWSTPQRFECDQE EGASSRAWRGGPPDYKDDDDKGGGLNDIFEAQKIEWHE |

As used herein, "CD123 antibody" refers to an antibody that specifically binds to CD123 and modulates biological activity and/or downstream event(s) mediated by CD123. In some embodiments, the CD123 antibody is an antagonist antibody. CD123 antagonist antibodies encompass antibodies that block, antagonize, suppress or reduce (to any degree including significantly) CD123 biological activity, including downstream events mediated by CD123, such as, e.g., IL-3 binding and/or downstream signaling, STAT5 phosphorylation, and survival of multipotent cells. Examples of CD123 antibodies and CD123 antibody-drug conjugates ("CD123 ADCs") are provided herein.

As used herein, "treatment" is an approach for obtaining beneficial or desired clinical results. For purposes of this invention, beneficial or desired clinical results include, but are not limited to, one or more of the following: reducing the proliferation of (or destroying) neoplastic or cancerous cells, inhibiting metastasis of neoplastic cells, remission of a CD123 associated disease (e.g., cancer or autoimmune disease), decreasing symptoms resulting from a CD123 associated disease (e.g., cancer or autoimmune disease), increasing the quality of life of those suffering from a CD123 associated disease (e.g., cancer or autoimmune disease), decreasing the dose of other medications required to treat a CD123 associated disease (e.g., cancer or autoimmune disease), delaying the progression of a CD123 associated disease (e.g., cancer or autoimmune disease), curing a CD123 associated disease (e.g, cancer or autoimmune disease), and/or prolong survival of subjects having a CD123 associated disease (e.g., cancer or autoimmune disease).

"Ameliorating" means a lessening or improvement of one or more symptoms as compared to not administering a CD123 antibody or a CD123 ADC. "Ameliorating" also includes shortening or reduction in duration of a symptom.

As used herein, an "effective dosage" or "effective amount" of drug, compound, or pharmaceutical composition is an amount sufficient to affect any one or more beneficial or desired results. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing incidence or amelioration of one or more symptoms of various CD123 associated diseases or conditions (such as for example without limitation, cancer), decreasing the dose of other medications required to treat the disease, enhancing the effect of another medication, and/or delaying the progression of the CD123 associated disease of subjects. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

An "individual" or a "subject" is a mammal, more preferably, a human. Mammals also include, but are not limited to, farm animals, sport animals, pets, primates, horses, dogs, cats, mice and rats.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by well-known conventional methods (see, for example, Remington's Pharmaceutical Sciences, 18th edition, A. Gennaro, ed., Mack Publishing Co., Easton, Pa., 1990; and Remington, The Science and Practice of Pharmacy 21st Ed. Mack Publishing, 2005).

The term "acyl donor glutamine-containing tag" or "glutamine tag" as used herein refers to a polypeptide or a protein containing one or more Gln residue(s) that acts as a transglutaminase amine acceptor. See, e.g., PCT Publication Nos. WO2012059882 and WO2015015448, which are hereby incorporated by reference in their entireties.

The term "$k_{on}$", as used herein, refers to the rate constant for association of an antibody to an antigen. Specifically, the rate constants ($k_{on}$ and $k_{off}$) and equilibrium dissociation constants are measured using IgGs and CD123 proteins (e.g., CD123-Fc fusion protein).

The term "$k_{off}$", as used herein, refers to the rate constant for dissociation of an antibody from the antibody/antigen complex.

The term "$K_D$", as used herein, refers to the equilibrium dissociation constant of an antibody-antigen interaction.

Reference to "about" a value or parameter herein includes (and describes) embodiments that are directed to that value or parameter per se. For example, description referring to "about X" includes description of "X." Numeric ranges are inclusive of the numbers defining the range.

As used herein, CPI refers to 1,2,8,8a-tetrahydrocyclopropa[c]pyrrolo[3,2-e]indol-4(5H)-one or a substituted or derivatized form thereof. CPI can also refer to the seco form of CPI, or seco-CPI, which is also know as 8-(chloromethyl)-1-methyl-3,6,7,8-tetrahydropyrrolo[3,2-e]indol-4-ol, or a substituted or derivatized form (or forms) thereof.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular.

Exemplary methods and materials are described herein, although methods and materials similar or equivalent to those described herein can also be used in the practice or testing of the present invention. The materials, methods, and examples are illustrative only and not intended to be limiting.

CD123 Antibodies and Antibody-Drug Conjugates

The present invention provides antibodies that bind to CD123 (e.g., human CD123 (e.g., SEQ ID NO: 1)) and conjugates (such as antibody-drug conjugates, or ADCs) comprising an anti-CD123 antibody, characterized by any one or more of the following characteristics: (a) treat, prevent, ameliorate one or more symptoms of a condition associated with malignant cells expressing CD123 in a subject (e.g., cancer such as, without limitation, AML, B-ALL, HCL, etc.); (b) inhibit tumor growth or progression in a subject (who has a malignant tumor expressing CD123); (c) inhibit metastasis of cancer (malignant) cells expressing CD123 in a subject (who has one or more malignant cells expressing CD123); (d) induce regression (e.g., long-term regression) of a tumor expressing CD123; and (e) exert cytotoxic activity in malignant cells expressing CD123.

The antibodies useful in the present invention can encompass monoclonal antibodies, polyclonal antibodies, antibody fragments (e.g., Fab, Fab', F(ab')$_2$, Fv, Fc, etc.), chimeric antibodies, bispecific antibodies, heteroconjugate antibodies, single chain (ScFv), mutants thereof, fusion proteins comprising an antibody portion (e.g., a domain antibody), humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies). In some embodiments, the CD123 antibody as described herein is a monoclonal antibody. For example, the CD123 antibody can be a humanized monoclonal antibody, human antibody, or a chimeric monoclonal antibody.

In some embodiments, the antibody can comprise a modified constant region, such as, for example without limitation, a constant region that has increased potential for provoking an immune response. For example, the constant region may be modified to have increased affinity to an Fc gamma receptor such as, e.g., FcγRI, FcγRIIA, or FcγIII. In some embodiments, the antibody comprises can comprise a constant region that is immunologically inert, that is, having a reduced potential for provoking an immune response. In some embodiments, the constant region is modified as described in Eur. J. Immunol., 29:2613-2624, 1999; PCT Application No. PCT/GB99/01441; and/or UK Patent Application No. 98099518. The Fc can be human IgG1, human IgG2, human IgG3, or human IgG4. The Fc can be human IgG2 containing the mutation A330P331 to S330S331 (IgG2Δa), in which the amino acid residues are numbered with reference to the wild type IgG2 sequence. Eur. J. Immunol., 29:2613-2624, 1999. In some embodiments, the antibody comprises a constant region of IgG$_4$ comprising the following mutations (Armour et al., Molecular Immunology 40 585-593, 2003): E233F234L235 to P233V234A235 (IgG4Δc), in which the numbering is with reference to wild type IgG4. In yet another embodiment, the Fc is human IgG4 E233F234L235 to P233V234A235 with deletion G236 (IgG4Δb). In another embodiment, the Fc is any human IgG4 Fc (IgG4, IgG4Δb or IgG4Δc) containing hinge stabilizing mutation S228 to P228 (Aalberse et al., Immunology 105, 9-19, 2002). In another embodiment, the Fc can be aglycosylated Fc.

In some embodiments, the constant region can be aglycosylated by mutating the oligosaccharide attachment residue (such as Asn297) and/or flanking residues that are part of the glycosylation recognition sequence in the constant region. In some embodiments, the constant region is aglycosylated for N-linked glycosylation enzymatically. The constant region may be aglycosylated for N-linked glycosylation enzymatically or by expression in a glycosylation deficient host cell.

One way of determining binding affinity of antibodies to CD123 is by measuring binding affinity of monofunctional Fab fragments of the antibody. To obtain monofunctional Fab fragments, an antibody (for example, IgG) can be cleaved with papain or expressed recombinantly. The affinity of a CD123 Fab fragment of an antibody can be determined by surface plasmon resonance (Biacore™3000™ surface plasmon resonance (SPR) system, Biacore™, INC, Piscataway N.J.) equipped with pre-immobilized streptavidin sensor chips (SA) or anti-mouse Fc or anti-human Fc using HBS-EP running buffer (0.01M HEPES, pH 7.4, 0.15 NaCl, 3 mM EDTA, 0.005% v/v Surfactant P20). Biotinylated or Fc fusion human CD123 can be diluted into HBS-EP buffer to a concentration of less than 0.5 µg/mL and injected across the individual chip channels using variable contact times, to achieve two ranges of antigen density, either 50-200 response units (RU) for detailed kinetic studies or 800-1,000 RU for screening assays. Regeneration studies have shown that 25 mM NaOH in 25% v/v ethanol effectively removes the bound Fab while keeping the activity of CD123 on the chip for over 200 injections. Typically, serial dilutions (spanning concentrations of 0.1-10× estimated K$_D$) of purified Fab samples are injected for 1 min at 100 µL/minute and dissociation times of up to 2 hours are allowed. The concentrations of the Fab proteins are determined by ELISA and/or SDS-PAGE electrophoresis using a Fab of known concentration (as determined by amino acid analysis) as a standard. Kinetic association rates (k$_{on}$) and dissociation rates (k$_{off}$) are obtained simultaneously by fitting the data globally to a 1:1 Langmuir binding model (Karlsson, R. Roos, H. Fagerstam, L. Petersson, B. (1994). Methods Enzymology 6. 99-110) using the BIAevaluation program. Equilibrium dissociation constant (K$_D$) values are calculated as k$_{off}$/k$_{on}$. This protocol is suitable for use in determining binding affinity of an antibody to any CD123, including human CD123, CD123 of another mammal (such as mouse CD123, rat CD123, or primate CD123), as well as different forms of CD123 (e.g., glycosylated CD123). Binding affinity of an antibody is generally measured at 25° C., but can also be measured at 37° C. The binding affinity (K$_D$) of the CD123 antibody as described herein to CD123 (such as human CD123 (e.g., (SEQ ID NO: 1) can be about 0.002 nM to about 6500 nM. In some embodiments, the binding affinity is about any of 6500 nm, 6000 nm, 5986 nm, 5567 nm, 5500 nm, 4500 nm, 4000 nm, 3500 nm, 3000 nm, 2500 nm, 2134 nm, 2000 nm, 1500 nm, 1000 nm, 750 nm, 500 nm, 400 nm, 300 nm, 250 nm, 200 nM, 193 nM, 100 nM, 90 nM, 50 nM, 45 nM, 40 nM, 35 nM, 30 nM, 25 nM, 20 nM, 19 nm, 18 nm, 17 nm, 16 nm, 15 nM, 10 nM, 8 nM, 7.5 nM, 7 nM, 6.5 nM, 6 nM, 5.5 nM, 5 nM, 4 nM, 3 nM, 2 nM, 1 nM, 0.5 nM, 0.3 nM, 0.1 nM, 0.01 nM, or 0.002 nM. In some embodiments, the binding affinity is less than about any of 6500 nm, 6000 nm, 5500 nm, 5000 nm, 4000 nm, 3000 nm, 2000 nm, 1000 nm, 900 nm, 800 nm, 250 nM, 200 nM, 100 nM, 50 nM, 30 nM, 20 nM, 10 nM, 7.5 nM, 7 nM, 6.5 nM, 6 nM, 5 nM, 4.5 nM, 4 nM, 3.5 nM, 3 nM, 2.5 nM, 2 nM, 1.5 nM, 1 nM, or 0.5 nM.

The CD123 antibodies as described herein may be made by any method known in the art. For the production of hybridoma cell lines, the route and schedule of immunization of the host animal are generally in keeping with established and conventional techniques for antibody stimulation and production, as further described herein. General techniques for production of human and mouse antibodies are known in the art and/or are described herein.

In some embodiments, a CD123 antibody can comprise a heavy chain variable region (VH) comprising three CDRs of a VH comprising the amino acid sequence of SEQ ID NOs: 6, 24, 32, 44, 51, or 64. In some aspects of the invention, an antibody comprises a light chain variable region (VL) comprising three CDRs of a VL comprising the amino acid sequence of SEQ ID NO: 17, 28, 39, 48, 57, or 71. In some aspects of the invention, an antibody comprises a VH comprising three CDRs of a VH comprising the amino acid sequence of SEQ ID NOs: 6, 24, 32, 44, 51, or 64, and a VL comprising three CDRs of a VL comprising the amino acid sequence of SEQ ID NO: 17, 28, 39, 48, 57, or 71. In other embodiments, a CD123 antibody may comprise a VH comprising the amino acid sequences of SEQ ID NOs: 7, 8, and 9 and a VL comprising the amino acid sequences of SEQ ID NOs: 18, 19, and 20. In other embodiments, a CD123 antibody may comprise a VH comprising the amino acid sequences of SEQ ID NOs: 7, 25, and 9 and a VL comprising the amino acid sequences of SEQ ID NOs: 18, 19, and 20. In other embodiments, a CD123 antibody may comprise a VH comprising the amino acid sequences of SEQ ID NOs: 33, 34, and 35 and a VL comprising the amino acid sequences of SEQ ID NOs: 40, 41, and 42. In other embodiments, a CD123 antibody may comprise a VH comprising the amino acid sequences of SEQ ID NOs: 33, 45, and 46 and a VL comprising the amino acid sequences of SEQ ID NOs: 40, 41, and 42. In other embodiments, a CD123 antibody may comprise a VH comprising the amino acid sequences of SEQ ID NOs: 52, 53, and 54 and a VL comprising the amino acid sequences of SEQ ID NOs: 58, 59, and 60. In other embodiments, a CD123 antibody may comprise a VH comprising the amino acid sequences of SEQ ID NOs: 65, 66, and 67 and a VL comprising the amino acid sequences of SEQ ID NOs: 72, 73, and 74.

Representative CD123 antibody heavy chain variable regions and light chain variable regions can comprise the amino acid sequences of SEQ ID NOs: 6, 24, 32, 44, 51, and 64 and SEQ ID NOs: 17, 28, 39, 48, 57, and 71, respectively. Representative CD123 antibody heavy chains and light amino chains can comprise the amino acid sequences of SEQ ID NOs: 15, 27, 37, 47, 55, and 69 and SEQ ID NOs: 23, 30, 43, 49, 62, and 76, respectively. Representative CD123 antibody sequences are shown in Table 2.0.

TABLE 2.0

Representative CD123 Antibody Sequences

| Antibody | Heavy Chain Sequences | | | | | Light Chain Sequences | | | | |
|---|---|---|---|---|---|---|---|---|---|---|
| | HC CDR1 | HC CDR2 | HC CDR3 | VH | HC | LC CDR1 | LC CDR2 | LC CDR3 | VL | LC |
| 18G3 | SEQ ID NO: 7 | SEQ ID NO: 8 | SEQ ID NO: 9 | SEQ ID NO: 6 | SEQ ID NO: 15 | SEQ ID NO: 18 | SEQ ID NO: 19 | SEQ ID NO: 20 | SEQ ID NO: 17 | SEQ ID NO: 23 |
| h18G3 | SEQ ID NO: 7 | SEQ ID NO: 25 | SEQ ID NO: 9 | SEQ ID NO: 24 | SEQ ID NO: 27 | SEQ ID NO: 18 | SEQ ID NO: 19 | SEQ ID NO: 20 | SEQ ID NO: 28 | SEQ ID NO: 30 |
| 16D6 | SEQ ID NO: 33 | SEQ ID NO: 34 | SEQ ID NO: 35 | SEQ ID NO: 32 | SEQ ID NO: 37 | SEQ ID NO: 40 | SEQ ID NO: 41 | SEQ ID NO: 42 | SEQ ID NO: 39 | SEQ ID NO: 43 |
| h16D6 | SEQ ID NO: 33 | SEQ ID NO: 45 | SEQ ID NO: 46 | SEQ ID NO: 44 | SEQ ID NO: 47 | SEQ ID NO: 40 | SEQ ID NO: 41 | SEQ ID NO: 42 | SEQ ID NO: 48 | SEQ ID NO: 49 |
| 3D1 | SEQ ID NO: 52 | SEQ ID NO: 53 | SEQ ID NO: 54 | SEQ ID NO: 51 | SEQ ID NO: 55 | SEQ ID NO: 58 | SEQ ID NO: 59 | SEQ ID NO: 60 | SEQ ID NO: 57 | SEQ ID NO: 62 |
| 20D7 | SEQ ID NO: 65 | SEQ ID NO: 66 | SEQ ID NO: 67 | SEQ ID NO: 64 | SEQ ID NO: 69 | SEQ ID NO: 72 | SEQ ID NO: 73 | SEQ ID NO: 74 | SEQ ID NO: 71 | SEQ ID NO: 76 |

Exemplary CD123 antibodies provided herein include 18G3, humanized 18G3 (h18G3), 16D6, humanized 16D6 (h16D6), 3D1, and 20D7 shown in Table 2.1. The sequences shown in Table 2.1 are amino acid sequences unless otherwise indicated.

TABLE 2.1

| SEQ ID NO: | DESCRIPTION | SEQUENCE |
|---|---|---|
| 5 | 18G3 VH nucleotide sequence | CAGGTGAAACTGAAGGAGTCAGGACCTGGCCTGGTGGCGCCCGCACAGAG TCTGTCCATTACCTGCACTGTCTCTGGATTCTCATTAACCAGTGGTGACATAA GTTGGATTCGCCAGCCACCAGGAAAGGGTCTGGAGTGGCTTGGAGTAATAT GGTCTGGCGGAGGCACAAATTATAATTCTCGTCTCATGTCCAGACTGAGCAT CACCAAGGACAACTCCAGGAGTCAAGTGTTCTTAAAAATGAACAGTCTGCA AACTGATGACACCGCCATATATTATTGTGTAAGAGATTGGGGTAACTTTTAC TTTGACTATTGGGGCCAAGGCACCACTCTCACAGTCTCCTCA |
| 6 | 18G3 VH with CDRs underlined | QVKLKESGPGLVAPAQSLSITCTVS<u>GFSLTSGDIS</u>WIRQPPGKGLEWLG<u>VIWSG GGTNYNSRLMS</u>RLSITKDNSRSQVFLKMNSLQTDDTAIYYCVRD<u>WGNFYFDY</u> WGQGTTLTVSS |
| 7 | 18G3 CDRH1 | GFSLTSGDIS |
| 8 | 18G3 CDRH2 | VIWSGGGTNYNSRLMS |
| 9 | 18G3 CDRH3 | DWGNFYFDY |
| 10 | 18G3 JH | WGQGTTLTVSS |
| 11 | CH1 | ASTKGPSVFPLAPSSKSTSGGTAALGCLVKDYFPEPVTVSWNSGALTSGVHTFP AVLQSSGLYSLSSVVTVPSSSLGTQTYICNVNHKPSNTKVDKKV |
| 12 | Hinge | EPKSCDRTHTCPPCP |
| 13 | CH2 | APELLGGPSVFLFPPKPKDTLMISRTPEVTCVVVDVSHEDPEVKFNWYVDGVEV HNAKTKPRELLQGSTYRVVSVLTVLHQDWLNGKEYKCKVSNKALPAPIEKTISKA K |
| 14 | CH3 | GQPREPQVYTLPPSREEMTKNQVSLTCLVKGFYPSDIAVEWESNGQPENNYKT TPPVLDSDGSFFLYSKLTVDKSRWQQGNVFSCSVMHEALHNHYTQKSLSLSPG |
| 15 | 18G3 HC | QVKLKESGPGLVAPAQSLSITCTVSGFSLTSGDISWIRQPPGKGLEWLGVIWSG GGTNYNSRLMSRLSITKDNSRSQVFLKMNSLQTDDTAIYYCVRDWGNFYFDY WGQGTTLTVSSASTKGPSVFPLAPSSKSTSGGTAALGCLVKDYFPEPVTVSWNS GALTSGVHTFPAVLQSSGLYSLSSVVTVPSSSLGTQTYICNVNHKPSNTKVDKKV EPKSCDRTHTCPPCPAPELLGGPSVFLFPPKPKDTLMISRTPEVTCVVVDVSHED PEVKFNWYVDGVEVHNAKTKPRELLQGSTYRVVSVLTVLHQDWLNGKEYKCK VSNKALPAPIEKTISKAKGQPREPQVYTLPPSREEMTKNQVSLTCLVKGFYPSDIA VEWESNGQPENNYKTTPPVLDSDGSFFLYSKLTVDKSRWQQGNVFSCSVMHE ALHNHYTQKSLSLSPG |

TABLE 2.1-continued

| SEQ ID NO: | DESCRIPTION | SEQUENCE |
|---|---|---|
| 16 | 18G3 VL nucleotide sequence | GACATTGTGATGTCACAGTCTCCATCCTCCCTGGCTGTGTCAGTAGGAGAGA AGGTCACTATGAGCTGCAAATCCAGTCAGAGTCTGCTCAGCAGTGGAACCC GAAAGAACTACTTGGCTTGGTACCAGCAGAAACCAGGGCAGTCTCCTAAAC TGCTGATCTACTGGGCATCCACTAGGCAATCTGGGGTCCCTGATCGCTTCAC AGGCGGTGGATCTGGGACAGATTTCACTCTCACCATCAGCAGTGTGCAGGC TGAGGACCTGGCAGTTTATTACTGCAGTCAATCTTATAATCTATACACATTCG GAGGGGGGACCAAGCTGGAAATAAAA |
| 17 | 18G3 VL with CDRs underlined | DIVMSQSPSSLAVSVGKVTMSC<u>KSSQSLLSSGTRKNYLA</u>WYQQKPGQSPKLLI Y<u>WASTRQS</u>GVPDRFTGGGSGTDFTLTISSVQAEDLAVYYC<u>SQSYNLYT</u>FGGGTK LEIK |
| 18 | 18G3 CDRL1 | KSSQSLLSSGTRKNYLA |
| 19 | 18G3 CDRL2 | WASTRQS |
| 20 | 18G3 CDRL3 | SQSYNLYT |
| 21 | 18G3 JK | FGGGTKLEIK |
| 22 | CL | (R)TVAAPSVFIFPPSDEQLKSGTASVVCLLNNFYPREAKVQWKVDNALQSGNS QESVTEQDSKDSTYSLSSTLTLSKADYEKHKVYACEVTHQGLSSPVTKSFNRGEC |
| 23 | 18G3 LC | DIVMSQSPSSLAVSVGEKVTMSCKSSQSLLSSGTRKNYLAWYQQKPGQSPKLLI YWASTRQSGVPDRFTGGGSGTDFTLTISSVQAEDLAVYYCSQSYNLYTFGGGTK LEIKRTVAAPSVFIFPPSDEQLKSGTASVVCLLNNFYPREAKVQWKVDNALQSG NSQESVTEQDSKDSTYSLSSTLTLSKADYEKHKVYACEVTHQGLSSPVTKSFNRG EC |
| 24 | h18G3 VH with CDRs underlined | EVQLVESGGGLVQPGGSLRLSCAASG<u>FSLTSGDIS</u>WVRQAPGKGLEWVA<u>VIWS GGGTNYGSRLMS</u>RFTISRDNAKNSLYLQMNSLRAEDTAVYYCAR<u>DWGNFYFD YW</u>GQGTLVTVSS |
| 25 | h18G3 CDRH2 | VIWSGGGTNYGSRLMS |
| 26 | h18G3 JH | WGQGTLVTVSS |
| 27 | h18G3 HC | EVQLVESGGGLVQPGGSLRLSCAASGFSLTSGDISWVRQAPGKGLEWVAVIWS GGGTNYGSRLMSRFTISRDNAKNSLYLQMNSLRAEDTAVYYCARDWGNFYFD YWGQGTLVTVSSASTKGPSVFPLAPSSKSTSGGTAALGCLVKDYFPEPVTVSWN SGALTSGVHTFPAVLQSSGLYSLSSVVTVPSSSLGTQTYICNVNHKPSNTKVDKK VEPKSCDRTHTCPPCPAPELLGGPSVFLFPPKPKDTLMISRTPEVTCVVVDVSHE DPEVKFNWYVDGVEVHNAKTKPRELLQGSTYRVVSVLTVLHQDWLNGKEYKC KVSNKALPAPIEKTISKAKGQPREPQVYTLPPSREEMTKNQVSLTCLVKGFYPSDI AVEWESNGQPENNYKTTPPVLDSDGSFFLYSKLTVDKSRWQQGNVFSCSVMH EALHNHYTQKSLSLSPG |
| 28 | h18G3 VL with CDRs underlined | DIQMTQSPSSLSASVGDRVTITC<u>KSSQSLLSSGTRKNYLA</u>WYQQKPGKAPKLLIY <u>WASTRQS</u>GVPSRFSGSGSGTDFTLTISSLQPEDFATYYC<u>SQSYNLYT</u>FGQGTKLEI K |
| 29 | h18G3 JK | FGQGTKLEIK |
| 30 | h18G3 LC | DIQMTQSPSSLSASVGDRVTITCKSSQSLLSSGTRKNYLAWYQQKPGKAPKLLIY WASTRQSGVPSRFSGSGSGTDFTLTISSLQPEDFATYYCSQSYNLYTFGQGTKLEI KRTVAAPSVFIFPPSDEQLKSGTASVVCLLNNFYPREAKVQWKVDNALQSGNS QESVTEQDSKDSTYSLSSTLTLSKADYEKHKVYACEVTHQGLSSPVTKSFNRGEC |
| 31 | 16D6 VH nucleotide sequence | CAGGTGCAGCTGAAGGAGTCAGGACCTGGCCTGGTGGCGCCCTCACAGAG CCTGTCCATAACCTGCACTGTCTCTGGGTTCTCATTAACCAACTTTGATATAA GTTGGATTCGCCAGCCACCAGGAAAGGGTCTGGAGTGGCTTGGAGTAATGT GGACTGGTGGAGGCACAAATTATAATTCAGCTTTCATGTCCAGACTGAGCAT CAGCAGGGACATCTCCAAAAGCCAAGTTTCCTTAAAAATGAGCAGTCTGCA AACTGATGACACAGCCATATATTACTGTGTAAGAGGGGATACTTACTTCTTT GCTATGGACTACTGGGGTCAAGGAACCTCCGTCACCGTCTCATCAG |
| 32 | 16D6 VH with CDRs underlined | QVQLKESGPGLVAPSQSLSITCTVS<u>GFSLTNFDIS</u>WIRQPPGKGLEWLGV<u>MWT GGGTNYNSAFMS</u>RLSISRDISKSQVSLKMSSLQTDDTAIYYCVR<u>GDTYFFAMDY</u> WGQGTSVTVSS |
| 33 | 16D6 CDRH1 | GFSLTNFDIS |
| 34 | 16D6 CDRH2 | VMWTGGGTNYNSAFMS |

TABLE 2.1-continued

| SEQ ID NO: | DESCRIPTION | SEQUENCE |
|---|---|---|
| 35 | 16D6 CDRH3 | GDTYFFAMDY |
| 36 | 16D6 JH | WGQGTSVTVSS |
| 37 | 16D6 HC | QVQLKESGPGLVAPSQSLSITCTVSGFSLTNFDISWIRQPPGKGLEWLGVMWT GGGTNYNSAFMSRLSISRDISKSQVSLKMSSLQTDDTAIYYCVRGDTYFFAMDY WGQGTSVTVSSASTKGPSVFPLAPSSKSTSGGTAALGCLVKDYFPEPVTVSWNS GALTSGVHTFPAVLQSSGLYSLSSVVTVPSSSLGTQTYICNVNHKPSNTKVDKKV EPKSCDRTHTCPPCPAPELLGGPSVFLFPPKPKDTLMISRTPEVTCVVVDVSHED PEVKFNWYVDGVEVHNAKTKPRELLQGSTYRVVSVLTVLHQDWLNGKEYKCK VSNKALPAPIEKTISKAKGQPREPQVYTLPPSREEMTKNQVSLTCLVKGFYPSDIA VEWESNGQPENNYKTTPPVLDSDGSFFLYSKLTVDKSRWQQGNVFSCSVMHE ALHNHYTQKSLSLSPG |
| 38 | 16D6 VL nucleotide sequence | GACATCCAGATGACCCAGTCTCCATCCTCCCTGTCTGCATCTGTAGGAGACA GAGTCACCATCACTTGCAAATCCAGTCAGAGTCTGCTCAGCAGTGGAACCCG AAAGAACTTCTTGTCTTGGTATCAGCAGAAACCAGGGAAAGCCCCTAAGCTC CTGATCTATTGGGCATCCACTAGGGGATCTGGGGTCCCATCAAGGTTCAGT GGCAGTGGATCTGGGACAGATTTCACTCTCACCATCAGCAGTCTGCAACCTG AAGATTTTGCAACTTACTACTGTAAACAATCTTATAATCTATACACGTTTGGC CAGGGGACCAAGCTGGAGATCAAA |
| 39 | 16D6 VL with CDRs underlined | DIVMSQSPSSLAVSAGEKVTMSCKSSQSLLSSGTRKNFLSWYQQKTGQSPKLLIY WASTRGSGVPDRFTGSGSGTDFTLTISSVQTEDLAVYYCKQSYNLYTFGGGTKL EIK |
| 40 | 16D6 CDRL1 | KSSQSLLSSGTRKNFLS |
| 41 | 16D6 CDRL2 | WASTRGS |
| 42 | 16D6 CDRL3 | KQSYNLYT |
| 43 | 16D6 LC | DIVMSQSPSSLAVSAGEKVTMSCKSSQSLLSSGTRKNFLSWYQQKTGQSPKLLIY WASTRGSGVPDRFTGSGSGTDFTLTISSVQTEDLAVYYCKQSYNLYTFGGGTKL EIKRTVAAPSVFIFPPSDEQLKSGTASVVCLLNNFYPREAKVQWKVDNALQSGN SQESVTEQDSKDSTYSLSSTLTLSKADYEKHKVYACEVTHQGLSSPVTKSFNRGE C |
| 44 | h16D6 VH with CDRs underlined | EVQLVESGGGLVQPGGSLRLSCAAS<u>GFSLTNFDIS</u>WVRQAPGKGLEWVA<u>VM WTGGGTNYQSAFMS</u>RFTISRDNAKNSLYLQMNSLRAEDTAVYYCAR<u>GDVYFF AMDY</u>WGQGTLVTVSS |
| 45 | h16D6 CDRH2 | VMWTGGGTNYQSAFMS |
| 46 | h16D6 CDRH3 | GDVYFFAMDY |
| 47 | h16D6 HC | EVQLVESGGGLVQPGGSLRLSCAASGFSLTNFDISWVRQAPGKGLEWVAVM WTGGGTNYQSAFMSRFTISRDNAKNSLYLQMNSLRAEDTAVYYCARGDVYFF AMDYWGQGTLVTVSSASTKGPSVFPLAPSSKSTSGGTAALGCLVKDYFPEPVTV SWNSGALTSGVHTFPAVLQSSGLYSLSSVVTVPSSSLGTQTYICNVNHKPSNTKV DKKVEPKSCDRTHTCPPCPAPELLGGPSVFLFPPKPKDTLMISRTPEVTCVVVDV SHEDPEVKFNWYVDGVEVHNAKTKPRELLQGSTYRVVSVLTVLHQDWLNGKE YKCKVSNKALPAPIEKTISKAKGQPREPQVYTLPPSREEMTKNQVSLTCLVKGFY PSDIAVEWESNGQPENNYKTTPPVLDSDGSFFLYSKLTVDKSRWQQGNVFSCS VMHEALHNHYTQKSLSLSPG |
| 48 | h16D6 VL with CDRs underlined | DIQMTQSPSSLSASVGDRVTITC<u>KSSQSLLSSGTRKNFLS</u>WYQQKPGKAPKLLIY <u>WASTRGS</u>GVPSRFSGSGSGTDFTLTISSLQPEDFATYYC<u>KQSYNLYT</u>FGQGTKLE IK |
| 49 | h16D6 LC | DIQMTQSPSSLSASVGDRVTITCKSSQSLLSSGTRKNFLSWYQQKPGKAPKLLIY WASTRGSGVPSRFSGSGSGTDFTLTISSLQPEDFATYYCKQSYNLYTFGQGTKLE IKRTVAAPSVFIFPPSDEQLKSGTASVVCLLNNFYPREAKVQWKVDNALQSGNS QESVTEQDSKDSTYSLSSTLTLSKADYEKHKVYACEVTHQGLSSPVTKSFNRGEC |
| 50 | 3D1 VH nucleotide sequence | GAGGTCCAGCTACAACAGTCTGGACCTGAACTGGTGAAGCCTGGGGCTTCA GTGAAGATGTCCTGTAAGGCTTCTGGATACACCTTCAGTGACTACTTCATGA AGTGGGTGAAACAGAGCCATGGAAAGAGACTTGAGTGGATTGGAGATATT AATCCTAACAATGGTGAAACTTTCTACAACCATCATTTCAAGGGCAAGGCCA CATTGACAATAGACAAATCCTCCAGTACAGCCTACATGCAGCTCAACAGCCT GACATCTGACGACTCTGCAGTCTATTACTGTGCAAGACCCCGGCGGGGGAA TGCTATGGACTTCTGGGGTCAAGGAACCTCAGTCACCGTCTCCTCA |

TABLE 2.1-continued

| SEQ ID NO: | DESCRIPTION | SEQUENCE |
|---|---|---|
| 51 | 3D1 VH with CDRs underlined | EVQLQQSGPELVKPGASVKMSCKASGYTFSDYFMKWVKQSHGKRLEWIGDIN PNNGETFYNHHFKGKATLTIDKSSSTAYMQLNSLTSDDSAVYYCARPRRGNAM DFWGQGTSVTVSS |
| 52 | 3D1 CDRH1 | GYTFSDYFMK |
| 53 | 3D1 CDRH2 | DINPNNGETFYNHHFKG |
| 54 | 3D1 CDRH3 | PRRGNAMDF |
| 55 | 3D1 HC | EVQLQQSGPELVKPGASVKMSCKASGYTFSDYFMKWVKQSHGKRLEWIGDIN PNNGETFYNHHFKGKATLTIDKSSSTAYMQLNSLTSDDSAVYYCARPRRGNAM DFWGQGTSVTVSSASTKGPSVFPLAPSSKSTSGGTAALGCLVKDYFPEPVTVSW NSGALTSGVHTFPAVLQSSGLYSLSSVVTVPSSSLGTQTYICNVNHKPSNTKVDK KVEPKSCDRTHTCPPCPAPELLGGPSVFLFPPKPKDTLMISRTPEVTCVVVDVSH EDPEVKFNWYVDGVEVHNAKTKPRELLQGSTYRVVSVLTVLHQDWLNGKEYK CKVSNKALPAPIEKTISKAKGQPREPQVYTLPPSREEMTKNQVSLTCLVKGFYPS DIAVEWESNGQPENNYKTTPPVLDSDGSFFLYSKLTVDKSRWQQGNVFSCSV MHEALHNHYTQKSLSLSPG |
| 56 | 3D1 VL nucleotide sequence | GACATTGTGATGACACAGTCTCCATCCTCCCTGGCTATGTCAGTAGGACAGA AGGTCACCATGAGCTGCAAGTCCAGTCAGAGCCTTTTAAATAGAGGCAATC AAAAGAACTATTTGGCCTGGTACCAGCAGAAACCAGGACAGTCTCCTAAATT TCTGGTATATTTTGCATCCACTAGGGAATCTGGGGTCCCTGATCGCTTCATA GGCAGTGGATCTGGGACAGATTTCACTCTTACCATCAGCAGTGTGCAGGCT GAAGACCTGGCAGATTATTTTGTCAGCAACATTATAGTATTCCGTACACGTT CGGAGGGGGGACCAAGCTGGAAATACAA |
| 57 | 3D1 VL with CDRs underlined | DIVMTQSPSSLAMSVGQKVTMSC<u>KSSQSLLNRGNQKNYLA</u>WYQQKPGQSPK FLVY<u>FASTRES</u>GVPDRFIGSGSGTDFTLTISSVQAEDLADYFC<u>QQHYSIPYT</u>FGGG TKLEIQ |
| 58 | 3D1 CDRL1 | KSSQSLLNRGNQKNYLA |
| 59 | 3D1 CDRL2 | FASTRES |
| 60 | 3D1 CDRL3 | QQHYSIPYT |
| 61 | 3D1 JK | FGGGTKLEIQ |
| 62 | 3D1 LC | DIVMTQSPSSLAMSVGQKVTMSCKSSQSLLNRGNQKNYLAWYQQKPGQSPK FLVYFASTRESGVPDRFIGSGSGTDFTLTISSVQAEDLADYFCQQHYSIPYTFGGG TKLEIQRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVTKSFN RGEC |
| 63 | 20D7 VH nucleotide sequence | GAAGTACAGCTGCAGCAGTCTGGGCCCGAGCTTCGGAGACCTGGGACCTCA GTCAAGCTGTCTTGTAAGGCTTCTGGCTACAGTATTACAGATTTCCTTATGTA CTGGGTAAAACATAGGCCAGAATACGGCCTGGAATGGATTGGATGGATTGA TCCTGAGGATGGTGAAACAAAATATGCTCAGAAGTTCCAAAGCAAGGCCCG ACTGACTGCAGATACGTCCTCCAAAACAGCCTACATGGAACTCAGCAGCCTG ACGTCTGAGGACACAGCAACCTATTTTTGTGCTAGATGGGGCTATATCACGG ATTATTTCTATGGCGGGTTTACTTACTGGGGCCGAGGCACTCTGGTCACTGT CTCTTCA |
| 64 | 20D7 VH with CDRs underlined | EVQLQQSGPELRRPGTSVKLSCKAS<u>GYSITDFLMY</u>WVKHRPEYGLEWIG<u>WIDP EDGETKYAQKFQS</u>KARLTADTSSKTAYMELSSLTSEDTATYFCAR<u>WGYITDYFYG GFTY</u>WGRGTLVTVSS |
| 65 | 20D7 CDRH1 | GYSITDFLMY |
| 66 | 20D7 CDRH2 | WIDPEDGETKYAQKFQS |
| 67 | 20D7 CDRH3 | WGYITDYFYGGFTY |
| 68 | 20D7 JH | WGRGTLVTVSS |

TABLE 2.1-continued

| SEQ ID NO: | DESCRIPTION | SEQUENCE |
|---|---|---|
| 69 | 20D7 HC | EVQLVESGGGLVQPGGSLRLSCAASGYSITDFLMYWVRQAPGKGLEWVAWID PEDGETKYAQKFQSKARFTISRDNAKNSLYLQMNSLRAEDTAVYYCARWGYIT DYFYGGFTYWGRGTLVTVSSASTKGPSVFPLAPSSKSTSGGTAALGCLVKDYFPE PVTVSWNSGALTSGVHTFPAVLQSSGLYSLSSVVTVPSSSLGTQTYICNVNHKPS NTKVDKKVEPKSCDRTHTCPPCPAPELLGGPSVFLFPPKPKDTLMISRTPEVTCV VVDVSHEDPEVKFNWYVDGVEVHNAKTKPRELLQGSTYRVVSVLTVLHQDWL NGKEYKCKVSNKALPAPIEKTISKAKGQPREPQVYTLPPSREEMTKNQVSLTCLV KGFYPSDIAVEWESNGQPENNYKTTPPVLDSDGSFFLYSKLTVDKSRWQQGNV FSCSVMHEALHNHYTQKSLSLSPG |
| 70 | 20D7 VL nucleotide sequence | GACATCCAGATGACCCAGTCTCCTCCAGTCCTGTCTGCATCTGTGGGAGACA GAGTCACTCTCAGCTGCAAAGCAAGTCAGAATATTAATAAGAACTTAGACTG GTATCAGCAAAAGCATGGAGAAGCTCCAAAACTCCTGATATATCATACAAAC ACTTTGCAAATGGGCATCCCATCAAGGTTCAGTGGCAGTGGATCTGGTACA GATTACGCACTCACCATCACCAGCCTGCAGCCTGAAGATGTTGCCACATATT ACTGCTATCAATATAACAGTGGGCCCACGTTTGGAGCTGGGACCAAGCTGG AACTGAGA |
| 71 | 20D7 VL with CDRs underlined | DIQMTQSPPVLSASVGDRVTLSC<u>KASQNINKNLD</u>WYQQKHGEAPKLLIY<u>HTNT LQM</u>GIPSRFSGSGSGTDYALTITSLQPEDVATYYC<u>YQYNSGPT</u>FGAGTKLELR |
| 72 | 20D7 CDRL1 | KASQNINKNLD |
| 73 | 20D7 CDRL2 | HTNTLQM |
| 74 | 20D7 CDRL3 | YQYNSGPT |
| 75 | 20D7 JL | FGAGTKLELR |
| 76 | 20D7 LC | DIQMTQSPPVLSASVGDRVTLSCKASQNINKNLDWYQQKHGEAPKLLIYHTNT LQMGIPSRFSGSGSGTDYALTITSLQPEDVATYYCYQYNSGPTFGAGTKLELRRT VAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC |

Substitution variants have at least one amino acid residue in the antibody molecule removed and a different residue inserted in its place. The sites of greatest interest for substitutional mutagenesis include the hypervariable regions, but framework alterations are also contemplated. Conservative substitutions are shown in Table 3 under the heading of "conservative substitutions." If such substitutions result in a change in biological activity, then more substantial changes, denominated "exemplary substitutions" in Table 3, or as further described below in reference to amino acid classes, may be introduced and the products screened.

TABLE 3

Amino Acid Substitutions

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |

TABLE 3-continued

Amino Acid Substitutions

| Original Residue | Conservative Substitutions | Exemplary Substitutions |
|---|---|---|
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a β-sheet or helical conformation, (b) the charge or hydrophobicity of the molecule at the target site, or (c) the bulk of the side chain. Naturally occurring residues are divided into groups based on common side-chain properties:

(1) Non-polar: Norleucine, Met, Ala, Val, Leu, lie;
(2) Polar without charge: Cys, Ser, Thr, Asn, Gin;
(3) Acidic (negatively charged): Asp, Glu;
(4) Basic (positively charged): Lys, Arg;
(5) Residues that influence chain orientation: Gly, Pro; and
(6) Aromatic: Trp, Tyr, Phe, His.

Non-conservative substitutions are made by exchanging a member of one of these classes for another class.

One type of substitution, for example, that may be made is to change one or more cysteines in the antibody, which may be chemically reactive, to another residue, such as, without limitation, alanine or serine. For example, there can be a substitution of a non-canonical cysteine. The substitution can be made in a CDR or framework region of a variable domain or in the constant region of an antibody. In some embodiments, the cysteine is canonical. Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

The present invention also provides a conjugate of the CD123 antibody as described herein, or of the antigen binding fragment thereof, wherein the antibody is conjugated to an agent (e.g., a cytotoxic agent) for targeted immunotherapy (e.g., antibody-drug conjugates, or ADCs) either directly or indirectly via a linker. For example, a cytotoxic agent can be linked or conjugated to the CD123 antibody thereof as described herein for targeted local delivery of the cytotoxic agent moiety to tumors (e.g., CD123 expressing tumor).

Methods for conjugating cytotoxic agent or other therapeutic agents to antibodies have been described in various publications. For example, chemical modification can be made in the antibodies either through lysine side chain amines or through cysteine sulfhydryl groups activated by reducing interchain disulfide bonds for the conjugation reaction to occur. See, e.g., Tanaka et al., FEBS Letters 579:2092-2096, 2005, and Gentle et al., Bioconjugate Chem. 15:658-663, 2004. Reactive cysteine residues engineered at specific sites of antibodies for specific drug conjugation with defined stoichiometry have also been described. See, e.g., Junutula et al., Nature Biotechnology, 26:925-932, 2008. Conjugation using an acyl donor glutamine-containing tag or an endogenous glutamine made reactive (i.e., the ability to form a covalent bond as an acyl donor) by polypeptide engineering in the presence of transglutaminase and an amine (e.g., a cytotoxic agent comprising or attached to a reactive amine) is also described in international applications WO2012/059882 and WO2015015448, which are hereby incorporated by reference in their entireties. Transglutaminases are protein-glutamine γ-glutamyltransferases (EC 2.3.2.13), which typically catalyze pH-dependent transamidation of glutamine residues with lysine residues. The transglutaminase used in the invention described herein can be obtained or made from a variety of sources, or engineered to catalyze transamidation of one or more endogenous glutamine residues with one or more lysine residues or amine donor agents containing one or more reactive amines. Methods for using transglutaminase to prepare ADCs are described in e.g. United States Patent Application Publication No. 20170043033, herein incorporated by reference in its entirety.

ADCs comprise an antibody component conjugated to a drug agent, typically through the use of a linker. In some embodiments, ADCs disclosed herein comprise an antibody site-specifically conjugated to an amine donor agent (e.g., a small molecule coupled to a linker with an amine donor unit) via an engineered glutamine-containing tag, an endogenous glutamine (i.e., native glutamines without engineering, such as glutamines in the variable domains, CDRs, etc.), and/or a reactive endogenous glutamine.

The endogenous glutamine can be made reactive (i.e., the ability to form a covalent bond as an acyl donor in the presence of an amine and a transglutaminase) by modifying one or more amino acid(s) (e.g., amino acid deletion, insertion, substitution, or mutation) in the antibody, by enzymatic deglycosylation, or by reacting with an engineered transglutaminase. Accordingly, in one aspect, provided is an antibody-drug conjugate (ADC) comprising the formula: antibody-(T-(X—Y—$Z_a)_b)_c$, wherein: T is 1) a glutamine-containing tag engineered at a specific site, 2) an endogenous glutamine, and/or 3) an endogenous glutamine made reactive by antibody engineering or an engineered transglutaminase; X is an amine donor unit; Y is a linker; and Z is an agent moiety; X—Y—Z is an amine donor agent site-specifically conjugated to the glutamine-containing tag, the endogenous glutamine, and/or the reactive endogenous glutamine; a is an integer from 1 to 6; b is an integer from 1 to 6; c is an integer from 1 to 20; and wherein the product (drug-antibody ratio) of a, b, and c is at least about 1. Both the glutamine-containing tag, the endogenous glutamine, and/or the reactive glutamine on the antibody, and the amine donor agent (X—Y—Z) described herein, are substrates for transglutaminase, and the linkage between the glutamine-containing tag and/or the endogenous/reactive glutamine, and the amine donor agent, is of the formula $CH_2$—$CH_2$—CO—NH—, wherein NH— is linked to a linker and an agent moiety.

In some embodiments, the CD123 antibody or the conjugate as described herein comprises an acyl donor glutamine-containing tag engineered at a specific site of the antibody (e.g., a carboxyl terminus, an amino terminus, or at another site in the CD123 antibody). In some embodiments, the tag comprises an amino acid glutamine (Q) or an amino acid sequence LQG, LLQGG (SEQ ID NO:77), LLQG (SEQ ID NO:78), LSLSQG (SEQ ID NO: 79), GGGLLQGG (SEQ ID NO: 80), GLLQG (SEQ ID NO: 81), LLQ, GSPLAQSHGG (SEQ ID NO: 82), GLLQGGG (SEQ ID NO: 83), GLLQGG (SEQ ID NO: 84), GLLQ (SEQ ID NO: 85), LLQLLQGA (SEQ ID NO: 86), LLQGA (SEQ ID NO: 87), LLQYQGA (SEQ ID NO: 88), LLQGSG (SEQ ID NO: 89), LLQYQG (SEQ ID NO: 90), LLQLLQG (SEQ ID NO: 91), SLLQG (SEQ ID NO: 92), LLQLQ (SEQ ID NO: 93), LLQLLQ (SEQ ID NO: 94), LLQGR (SEQ ID NO: 95), LLQGPP (SEQ ID NO: 96), LLQGPA (SEQ ID NO: 97), GGLLQGPP (SEQ ID NO: 98), GGLLQGA (SEQ ID NO: 99), LLQGPGK (SEQ ID NO: 100), LLQGPG (SEQ ID NO: 101), LLQGP (SEQ ID NO: 102), LLQP (SEQ ID NO: 103), LLQPGK (SEQ ID NO: 104), LLQAPGK (SEQ ID NO: 105), LLQGAPG (SEQ ID NO: 106), LLQGAP (SEQ ID NO: 107), and LLQLQG (SEQ ID NO: 108).

In some embodiments, the acyl donor glutamine-containing tag comprises, e.g., LLQG (SEQ ID NO: 78) which replaces amino acid residues E294-N297 in the antibody heavy chain.

Also provided is an isolated antibody comprising an acyl donor glutamine-containing tag and an amino acid modification at position 222, 340, or 370 of the antibody (EU numbering scheme) wherein the modification is an amino acid deletion, insertion, substitution, mutation, or any combination thereof. In some embodiments, the amino acid modification is a substitution from lysine to arginine (e.g., K222R, K340R, or K370R).

The agents that can be conjugated to the CD123 antibodies or the antigen binding fragments of the present invention include, but are not limited to, cytotoxic agents, immuno-modulating agents, imaging agents, therapeutic proteins, biopolymers, or oligonucleotides.

Examples of a cytotoxic agent include, but are not limited to, anthracycline, an auristatin, a dolastatin, a combretastatin, a duocarmycin, a pyrrolobenzodiazepine dimer, an indolino-benzodiazepine dimer, an enediyne, a geldanamycin, a maytansine, a puromycin, a taxane, a vinca alkaloid, a camptothecin, a tubulysin, a hemiasterlin, a spliceostatin, a pladienolide, and stereoisomers, isosteres, analogs, or derivatives thereof.

In some aspects, the drug/agent is a cyclopropylpyrroloindoline (CPI) dimer, CTI dimer, or CBI dimer. CPI dimers induce inter-strand DNA crosslinking and potent cytotoxicity. PCT International Publication No. WO2015/110935, which is incorporated herein by reference in its entirety, discloses CPI and CBI dimers that are useful in the CD123 ADCs of the present invention and provides methods of producing the CPI and CBI dimers. For example, agent (8S)-8-(chloromethyl)-6-[(3-{[(1S)-1-(chloromethyl)-5-hydroxy-8-methyl-1,6-dihydropyrrolo[3,2-e]indol-3(2H)-yl]carbonyl}bicyclo[1.1.1]pent-1-yl)carbonyl]-1-methyl-3,6,7,8-tetrahydropyrrolo[3,2-e]indol-4-yl dihydrogen phosphate (also known as "CPI-8314 dimer" has the structure:

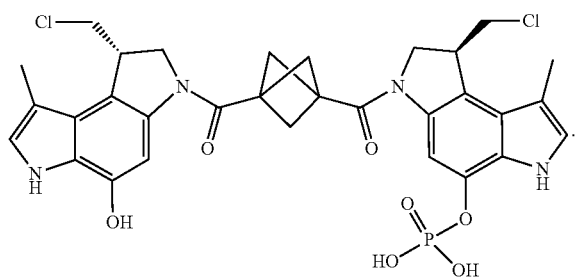 [SMILES: Cc1c[nH]c2c(O)cc3c(c12)[C@H](CCl)CN3C(=O)C12CC(C(=O)N3C[C@@H](CCl)c4c3cc(OP(=O)(O)O)c3[nH]cc(C)c43)(C1)C2]

having the formula C31H31Cl2N4O7P.

The anthracyclines are derived from bacteria *Strepomyces* and have been used to treat a wide range of cancers, such as leukemias, lymphomas, breast, uterine, ovarian, and lung cancers. Exemplary anthracyclines include, but are not limited to, daunorubicin, doxorubicin (i.e., adriamycin), epirubicin, idarubicin, valrubicin, and mitoxantrone.

Dolastatins and their peptidic analogs and derivatives, auristatins, are highly potent antimitotic agents that have been shown to have anticancer and antifungal activity. See, e.g., U.S. Pat. No. 5,663,149 and Pettit et al., *Antimicrob. Agents Chemother.* 42:2961-2965, 1998. Exemplary dolastatins and auristatins include, but are not limited to, dolastatin 10, auristatin E, auristatin EB (AEB), auristatin EFP (AEFP), MMAD (Monomethyl Auristatin D or monomethyl dolastatin 10), MMAF (Monomethyl Auristatin F or N-methylvaline-valine-dolaisoleuine-dolaproine-phenylalanine), MMAE (Monomethyl Auristatin E or N-methylvaline-valine-dolaisoleuine-dolaproine-norephedrine), 5-benzoylvaleric acid-AE ester (AEVB), and other novel auristatins (such as the ones described in U.S. Publication No. 2013/0129753). In some embodiments, the auristatin is 0101 (2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide) having the following structure:

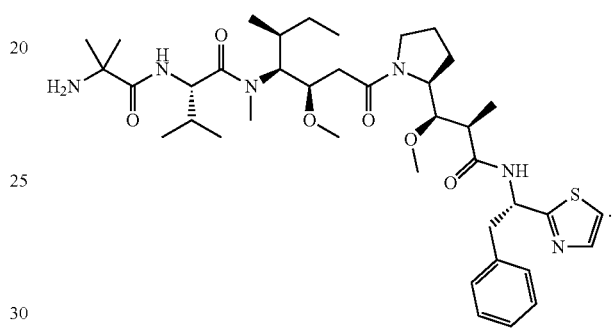

In some embodiments, the auristatin is 3377 (N,2-dimethylalanyl-N-{(1S,2R)-4-{(2S)-2-[(1R,2R)-3-{[(1S)-1-carboxyl-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide) having the following structure:

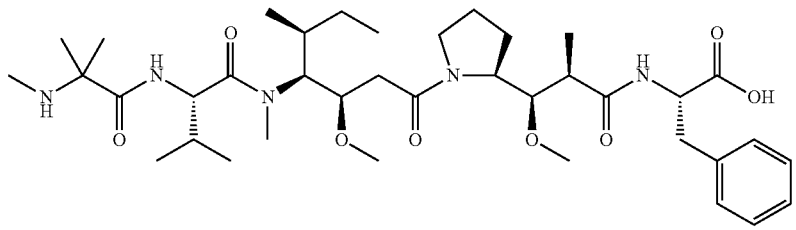 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)C(C)(C)NC)C(C)C]

In some embodiments, the auristatin is 0131-OMe (N,2-dimethylalanyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methyl L-valinamide) having the following structure:

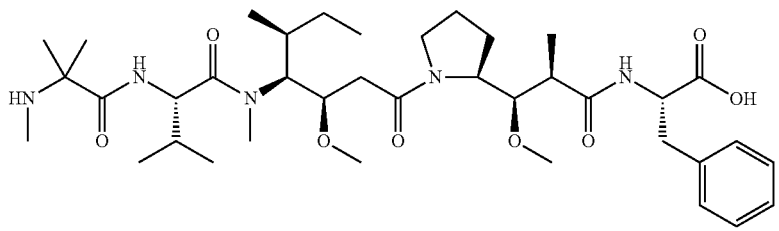 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)C(C)(C)NC)C(C)C]

In other embodiments, the auristatin is 0131 (2-methyl-L-proly-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide) having the following structure:

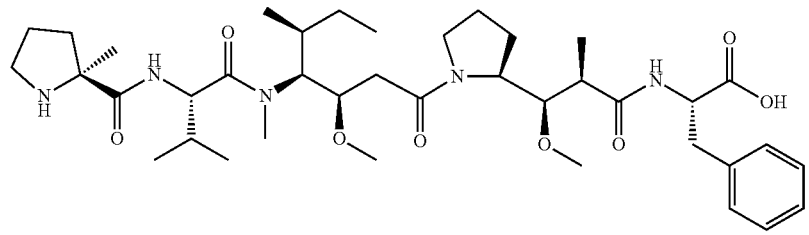 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@]1(C)CCCN1)C(C)C]

In other embodiments, the auristatin is 0121 (2-methyl-L-proly-N-[(3R,4S,5S)-1-{(2S)-2-[(1R,2R)-3-{[(2S)-1-methoxy-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide) having the following structure:

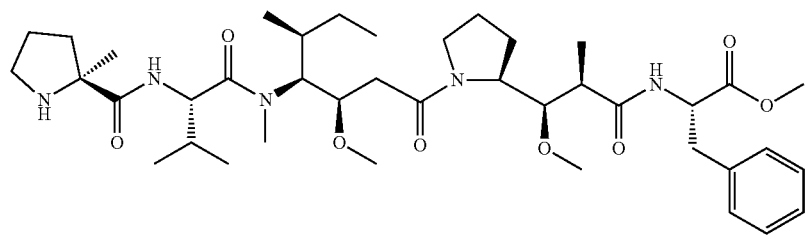 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@]1(C)CCCN1)C(C)C]

Camptothecin is a cytotoxic quinoline alkaloid which inhibits the enzyme topoisomerase I. Examples of camptothecin and its derivatives include, but are not limited to, topotecan and irinotecan, and their metabolites, such as SN-38.

Combretastatins are natural phenols with vascular disruption properties in tumors. Exemplary combretastatins and their derivatives include, but are not limited to, combretastatin A-4 (CA-4) and ombrabulin.

Duocarmycin and CC-1065 are DNA alkylating agents with cytotoxic potency. See Boger and Johnson, *PNAS* 92:3642-3649 (1995). Exemplary duocarmycin and CC-1065 include, but are not limited to, (+)-duocarmycin A and (+)-duocarmycin SA, (+)-CC-1065, and the compounds as disclosed in the international application PCT/IB2015/050280 including, but not limited to, N~2~-acetyl-L-lysyl-L-valyl-N~5~-carbamoyl-N-[4-({[(2-{[({(1S)-1-(chloromethyl)-3-[(5-{[(1S)-1-(chloromethyl)-5-(phosphonooxy)-1,2-dihydro-3H-benzo[e]indol-3-yl]carbonyl}thiophen-2-yl)carbonyl]-2,3-dihydro-1H-benzo[e]indol-5-yl}oxy)carbonyl](methyl)amino}ethyl)(methyl)carbamoyl]oxy}methyl)phenyl]-L-ornithinamide having the structure:

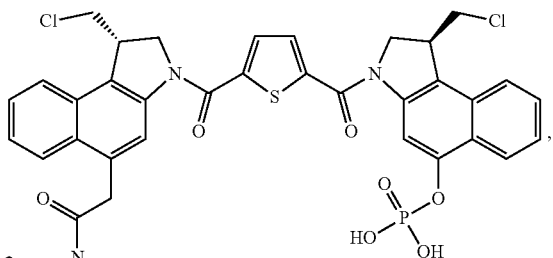
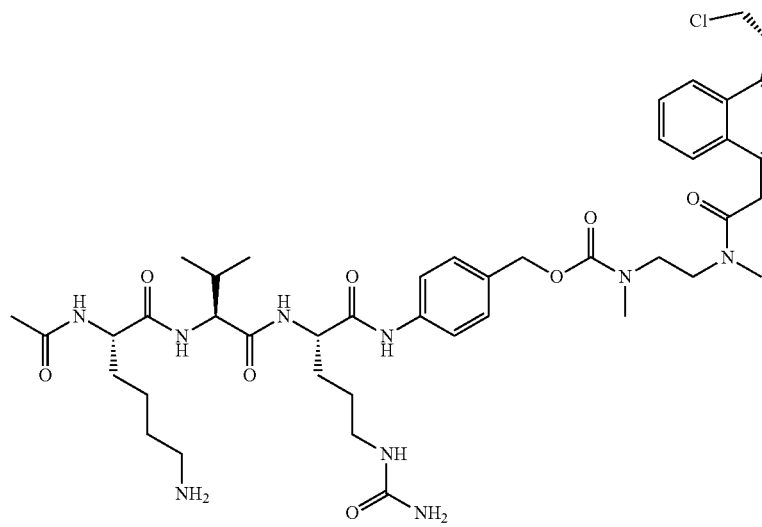

N~2~-acetyl-L-lysyl-L-valyl-N~5~-carbamoyl-N-[4-({[(2-{[({(8S)-8-(chloromethyl)-6-[(3-{[(1S)-1-(chloromethyl)-8-methyl-5-(phosphonooxy)-1,6-dihydropyrrolo[3,2-e]indol-3(2H)-yl]carbonyl}bicyclo[1.1.1]pent-1-yl)carbonyl]-1-methyl-3,6,7,8-tetrahydropyrrolo[3,2-e]indol-4-yl}oxy)carbonyl](methyl)amino}ethyl)(methyl)carbamoyl]oxy}methyl)phenyl]-L-ornithinamide having the structure:

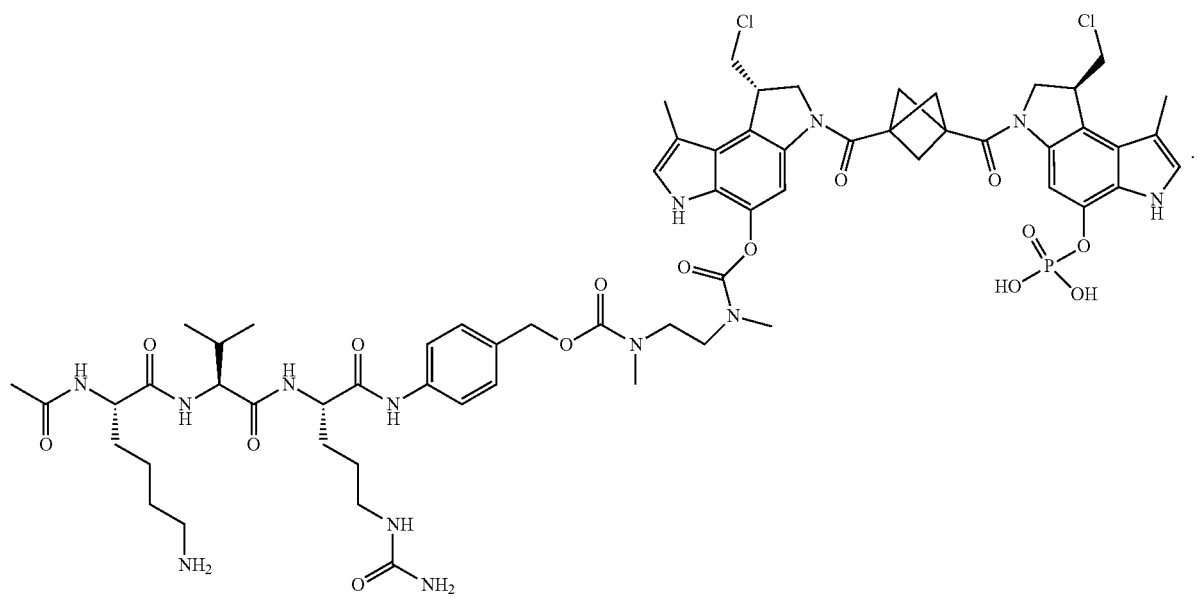 [SMILES: CC(=O)N[C@@H](CCCCN)C(=O)N[C@H](C(=O)N[C@@H](CCCNC(N)=O)C(=O)Nc1ccc(COC(=O)N(C)CCN(C)C(=O)Oc2cc3c(c4c(C)c[nH]c24)[C@H](CCl)CN3C(=O)C23CC(C(=O)N4C[C@@H](CCl)c5c4cc(OP(=O)(O)O)c4[nH]cc(C)c54)(C2)C3)cc1)C(C)C]

N~2~-acetyl-L-lysyl-L-valyl-N~5~-carbamoyl-N-[4-({[(2-{[({(8S)-8-(chloromethyl)-6-[(4-{[(1S)-1-(chloromethyl)-8-methyl-5-(phosphonooxy)-1,6-dihydropyrrolo[3,2-e]indol-3(2H)-yl]carbonyl}pentacyclo[4.2.0.0~2,5~.0~3,8~.0~4,7~]oct-1-yl)carbonyl]-1-methyl-3,6,7,8-tetrahydropyrrolo[3,2-e]indol-4-yl}oxy)carbonyl](methyl)amino}ethyl)(methyl)carbamoyl]oxy}methyl)phenyl]-L-ornithinamide having the structure:

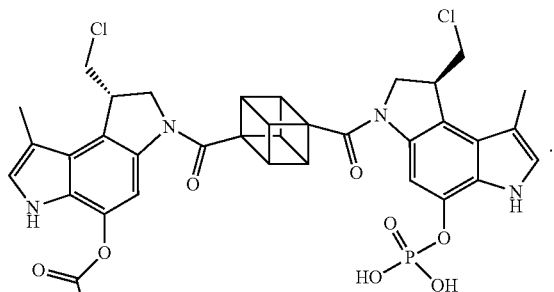
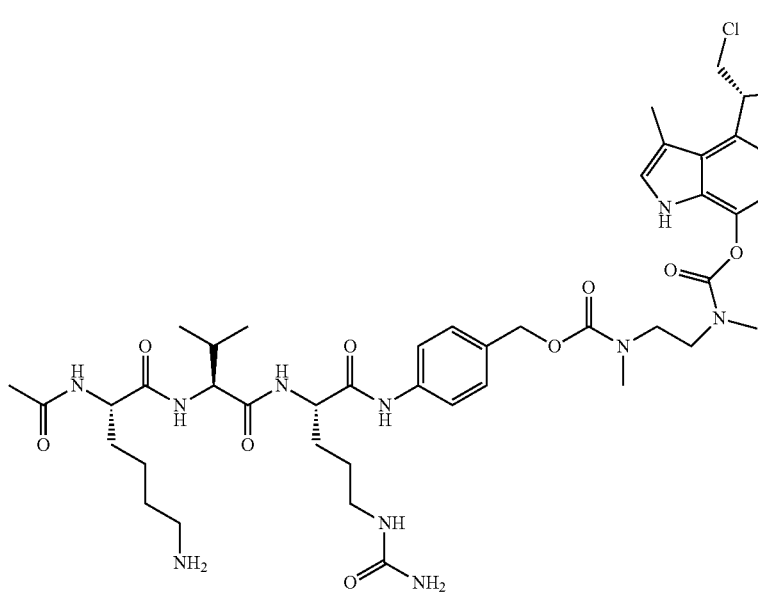

Enediynes are a class of anti-tumor bacterial products characterized by either nine- and ten-membered rings or the presence of a cyclic system of conjugated triple-double-triple bonds. Exemplary enediynes include, but are not limited to, calicheamicin, esperamicin, uncialamicin, dynemicin, and their derivatives.

Geldanamycins are benzoquinone ansamycin antibiotic that bind to Hsp90 (Heat Shock Protein 90) and have been used antitumor drugs. Exemplary geldanamycins include, but are not limited to, 17-AAG (17-N-Allylamino-17-Demethoxygeldanamycin) and 17-DMAG (17-Dimethyl-aminoethylamino-17-demethoxygeldanamycin).

Hemiasterlin and its analogues (e.g., HTI-286) bind to the tubulin, disrupt normal microtubule dynamics, and, at stoichiometric amounts, depolymerize microtubules.

Maytansines or their derivatives maytansinoids inhibit cell proliferation by inhibiting the microtubules formation during mitosis through inhibition of polymerization of tubulin. See Remillard et al., Science 189:1002-1005, 1975.

Exemplary maytansines and maytansinoids include, but are not limited to, mertansine (DM1) and its derivatives as well as ansamitocin.

Pyrrolobenzodiazepine dimers (PBDs) and indolino-benzodiazepine dimers (IGNs) are anti-tumor agents that contain one or more immine functional groups, or their equivalents, that bind to duplex DNA. PBD and IGN molecules are based on the natural product athramycin, and interact with DNA in a sequence-selective manner, with a preference for purine-guanine-purine sequences. Exemplary PBDs and their analogs include, but are not limited to, SJG-136.

Spliceostatins and pladienolides are anti-tumor compounds which inhibit splicing and interacts with spliceosome, SF3b. Examples of spliceostatins include, but are not limited to, spliceostatin A, FR901464, and (2S,3Z)-5-{[(2R,3R,5S,6S)-6-{(2E,4E)-5-[(3R,4R,5R,7S)-7-(2-hydrazinyl-2-oxoethyl)-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate having the structure of

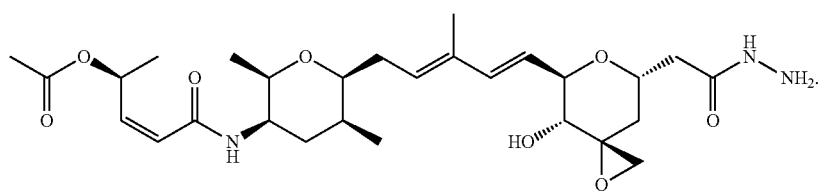 [SMILES: CC(=O)O[C@@H](C)/C=C\C(=O)N[C@@H]1C[C@H](C)[C@H](C/C=C(C)/C=C/[C@H]2O[C@H](CC(=O)NN)C[C@@]3(CO3)[C@@H]2O)O[C@@H]1C]

Examples of pladienolides include, but are not limited to, Pladienolide B, Pladienolide D, or E7107.

Taxanes are diterpenes that act as anti-tubulin agents or mitotic inhibitors.

Exemplary taxanes include, but are not limited to, paclitaxel (e.g., TAXOL®) and docetaxel (TAXOTERE®).

Tubulysins are natural products isolated from a strain of myxobacteria that has been shown to depolymerize microtubules and induce mitotic arrest. Exemplary tubulysins include, but are not limited to, tubulysin A, tubulysin B, and tubulysin D.

Vinca alkyloids are also anti-tubulin agents. Exemplary vinca alkyloids include, but are not limited to, vincristine, vinblastine, vindesine, and vinorelbine.

In some embodiments, the cytotoxic agent is selected from the group consisting of MMAD (Monomethyl Auristatin D), 0101 (2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide), 3377 (N,2-dimethylalanyl-N-{(1S,2R)-4-{(2S)-2-[(1R,2R)-3-{[(1S)-1-carboxyl-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide), 0131 (2-methyl-L-proly-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide), 0131-OMe (N,2-dimethylalanyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methylL-valinamide), 0121 (2-methyl-L-proly-N-[(3R,4S,5S)-1-{(2S)-2-[(1R,2R)-3-{[(2S)-1-methoxy-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide), and (2S,3Z)-5-{[(2R,3R,5S,6S)-6-{(2E,4E)-5-[(3R,4R,5R,7S)-7-(2-hydrazinyl-2-oxoethyl)-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate.

In some embodiments, the agent is an immunomodulating agent. Examples of an immunomodulating agent include, but are not limited to, gancyclovier, etanercept, tacrolimus, sirolimus, voclosporin, cyclosporine, rapamycin, cyclophosphamide, azathioprine, mycophenolgate mofetil, methotrextrate, glucocorticoid and its analogs, cytokines, stem cell growth factors, lymphotoxins, tumor necrosis factor (TNF), hematopoietic factors, interleukins (e.g., interleukin-1 (IL-1), IL-2, IL-3, IL-6, IL-10, IL-12, IL-18, and IL-21), colony stimulating factors (e.g., granulocyte-colony stimulating factor (G-CSF) and granulocyte macrophage-colony stimulating factor (GM-CSF)), interferons (e.g., interferons-α, -β and -γ), the stem cell growth factor designated "S 1 factor," erythropoietin and thrombopoietin, or a combination thereof.

In some embodiments, the agent moiety is an imaging agent (e.g., a fluorophore or a chelator), such as fluorescein, rhodamine, lanthanide phosphors, and their derivatives thereof, or a radioisotope bound to a chelator. Examples of fluorophores include, but are not limited to, fluorescein isothiocyanate (FITC) (e.g., 5-FITC), fluorescein amidite (FAM) (e.g., 5-FAM), eosin, carboxyfluorescein, erythrosine, Alexa Fluor® (e.g., Alexa 350, 405, 430, 488, 500, 514, 532, 546, 555, 568, 594, 610, 633, 647, 660, 680, 700, or 750), carboxytetramethylrhodamine (TAMRA) (e.g., 5-TAMRA), tetramethylrhodamine (TMR), and sulforhodamine (SR) (e.g., SR101). Examples of chelators include, but are not limited to, 1,4,7,10-tetraazacyclododecane-N,N', N'',N'''-tetraacetic acid (DOTA), 1,4,7-triazacyclononane-1,4,7-triacetic acid (NOTA), 1,4,7-triazacyclononane, 1-glutaric acid-4,7-acetic acid (deferoxamine), diethylenetriaminepentaacetic acid (DTPA), and 1,2-bis(o-aminophenoxy)ethane-N,N,N',N'-tetraacetic acid) (BAPTA).

Examples of fluorophores include, but are not limited to, fluorescein isothiocyanate (FITC) (e.g., 5-FITC), fluorescein amidite (FAM) (e.g., 5-FAM), eosin, carboxyfluorescein, erythrosine, Alexa Fluor® (e.g., Alexa 350, 405, 430, 488, 500, 514, 532, 546, 555, 568, 594, 610, 633, 647, 660, 680, 700, or 750), carboxytetramethylrhodamine (TAMRA) (e.g., 5-TAMRA), tetramethylrhodamine (TMR), and sulforhodamine (SR) (e.g., SR101).

In some embodiments, therapeutic or diagnostic radioisotopes or other labels (e.g., PET or SPECT labels) can be incorporated in the agent for conjugation to the CD123 antibodies or the antigen binding fragments as described herein. Examples of a radioisotope or other labels include, but are not limited to, $^{3}H$, $^{11}C$, $^{13}N$, $^{14}C$, $^{15}N$, $^{15}O$, $^{35}S$, $^{18}F$, $^{32}P$, $^{33}P$, $^{47}Sc$, $^{51}Cr$, $^{57}Co$, $^{58}Co$, $^{59}Fe$, $^{62}Cu$, $^{64}Cu$, $^{67}Cu$, $^{67}Ga$, $^{68}Ga$, $^{75}Se$, $^{76}Br$, $^{77}Br$, $^{86}Y$, $^{89}Zr$, $^{90}Y$, $^{94}Tc$, $^{95}Ru$, $^{97}Ru$, $^{99}Tc$, $^{103}Ru$, $^{105}Rh$, $^{105}Ru$, $^{107}Hg$, $^{109}Pd$, $^{111}Ag$, $^{111}In$, $^{113}In$, $^{121}Te$, $^{122}Te$, $^{123}I$, $^{124}I$, $^{125}I$, $^{125}Te$, $^{126}I$, $^{131}I$, $^{131}In$, $^{133}I$, $^{142}Pr$, $^{143}Pr$, $^{153}Pb$, $^{153}Sm$, $^{161}Tb$, $^{165}Tm$, $^{166}Dy$, $^{166}H$, $^{167}Tm$, $^{168}Tm$, $^{169}Yb$, $^{177}Lu$, $^{186}Re$, $^{188}Re$, $^{189}Re$, $^{197}Pt$, $^{198}Au$, $^{199}Au$, $^{201}Tl$, $^{203}Hg$, $^{211}At$, $^{212}Bi$, $^{212}Pb$, $^{213}Bi$, $^{223}Ra$, $^{224}Ac$, or $^{225}Ac$.

In some embodiments, the agent is a therapeutic protein including, but is not limited to, a toxin, a hormone, an enzyme, and a growth factor.

Examples of a toxin protein (or polypeptide) include, but are not limited to, dipththeria (e.g., diphtheria A chain), *Pseudomonas* exotoxin and endotoxin, ricin (e.g., ricin A chain), abrin (e.g., abrin A chain), modeccin (e.g., modeccin A chain), alpha-sarcin, *Aleurites fordii* proteins, dianthin proteins, ribonuclease (RNase), DNase I, Staphylococcal enterotoxin-A, pokeweed antiviral protein, gelonin, diphtherin toxin, *Phytolaca americana* proteins (PAPI, PAPII, and PAP-S), *Momordica charantia* inhibitor, curcin, crotin, *Sapaonaria officinalis* inhibitor, mitogellin, restrictocin, phenomycin, enomycin, tricothecenes, inhibitor cystine knot (ICK) peptides (e.g., ceratotoxins), and conotoxin (e.g., KIIIA or SmIIIa).

In some embodiments, the agent is a biocompatible polymer. The CD123 antibodies or the antigen binding fragments as described herein can be conjugated to the biocompatible polymer to increase serum half-life and bioactivity, and/or to extend in vivo half-lives. Examples of biocompatible polymers include water-soluble polymer, such as polyethylene glycol (PEG) or its derivatives thereof and zwitterion-containing biocompatible polymers (e.g., a phosphorylcholine containing polymer).

In some embodiments, the agent is an oligonucleotide, such as anti-sense oligonucleotides.

In another aspect, the invention provides a conjugate of the antibody as described herein, wherein the conjugate comprises the formula: antibody-(acyl donor glutamine-containing tag)-(linker)-(cytotoxic agent), wherein the acyl donor glutamine-containing tag is engineered at a specific site of the antibody (e.g., at a carboxyl terminus of the heavy or light chain, after residue T135 in the antibody heavy chain, or at an another site), wherein the tag is conjugated to a linker (e.g., a linker containing one or more reactive amines (e.g., primary amine $NH_2$)), and wherein the linker is conjugated to a cytotoxic agent (e.g., MMAD or other auristatins such as 0101, 0131, or 3377).

Examples of a linker containing one or more reactive amines include, but are not limited to, Ac-Lys-Gly (acetyl-lysine-glycine), aminocaproic acid, Ac-Lys-β-Ala (acetyl-lysine-β-alanine), amino-PEG2 (polyethylene glycol)-C2, amino-PEG3-C2, amino-PEG6-C2 (or amino PEG6-propionyl), Ac-Lys-Val-Cit-PABC (acetyl-lysine-valine-citrulline-p-aminobenzyloxycarbonyl), amino-PEG6-C2-Val-Cit-PABC, aminocaproyl-Val-Cit-PABC, [(3R,5R)-1-{3-[2-(2-aminoethoxy)ethoxy]propanoyl}piperidine-3,5-diyl]bis- Val-Cit-PABC, [(3S,5S)-1-{3-[2-(2-aminoethoxy)ethoxy]propanoyl}piperidine-3,5-diyl]bis-Val-Cit-PABC, putrescine, or Ac-Lys-putrescine.

In some embodiments, the (linker)-(cytotoxic agent) is $N^2$-acetyl-L-lysyl-L-valyl-$N^5$-carbamoyl-N-[4-({[(2-{[({(8S)-8-(chloromethyl)-6-[(3-{[(1S)-1-(chloromethyl)-8-methyl-5-(phosphonooxy)-1,6-dihydropyrrolo[3,2-e]indol-3(2H)-yl]carbonyl}bicyclo[1.1.1]p ent-1-yl)carbonyl]-1-methyl-3,6,7,8-tetrahydropyrrolo[3,2-e]indol-4-yl}oxy)carbonyl](methyl)amino}ethyl)(methyl)carbamoyl]oxy}methyl)phenyl]-L-ornithinamide, molecular formula C63H82Cl2N13O15P having the structure:

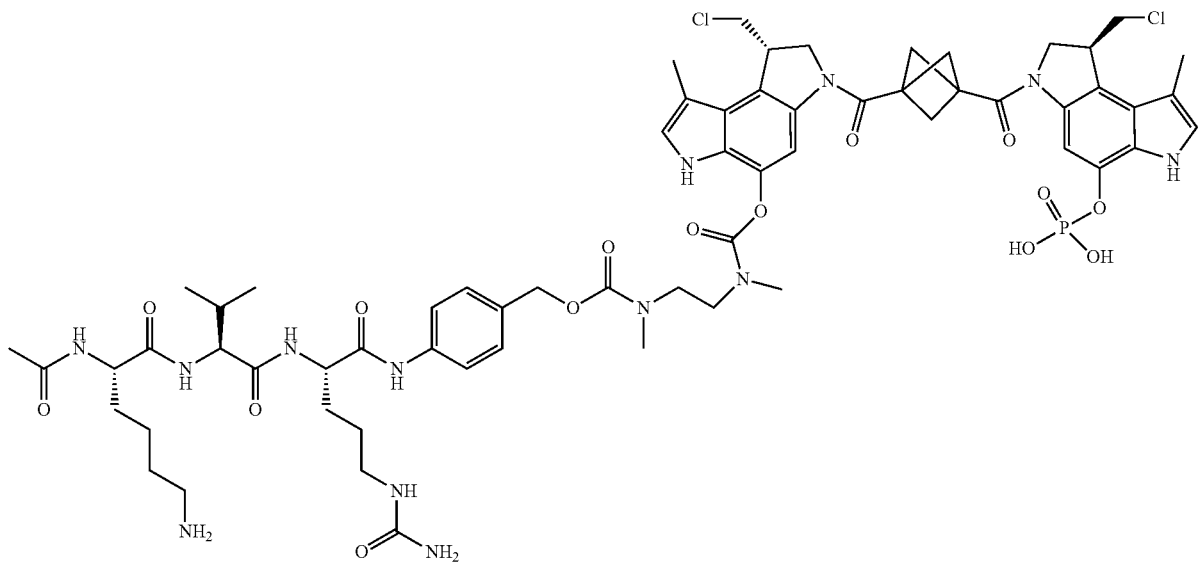 [SMILES: CC(=O)N[C@@H](CCCCN)C(=O)N[C@H](C(=O)N[C@@H](CCCNC(N)=O)C(=O)Nc1ccc(COC(=O)N(C)CCN(C)C(=O)Oc2cc3c(c4c(C)c[nH]c24)[C@H](CCl)CN3C(=O)C23CC(C(=O)N4C[C@@H](CCl)c5c4cc(OP(=O)(O)O)c4[nH]cc(C)c54)(C2)C3)cc1)C(C)C]

In some embodiments, the (linker)-(cytotoxic agent) is the trifluoroacetic acid salt form of C63H82Cl2N13O15P having the following structure:

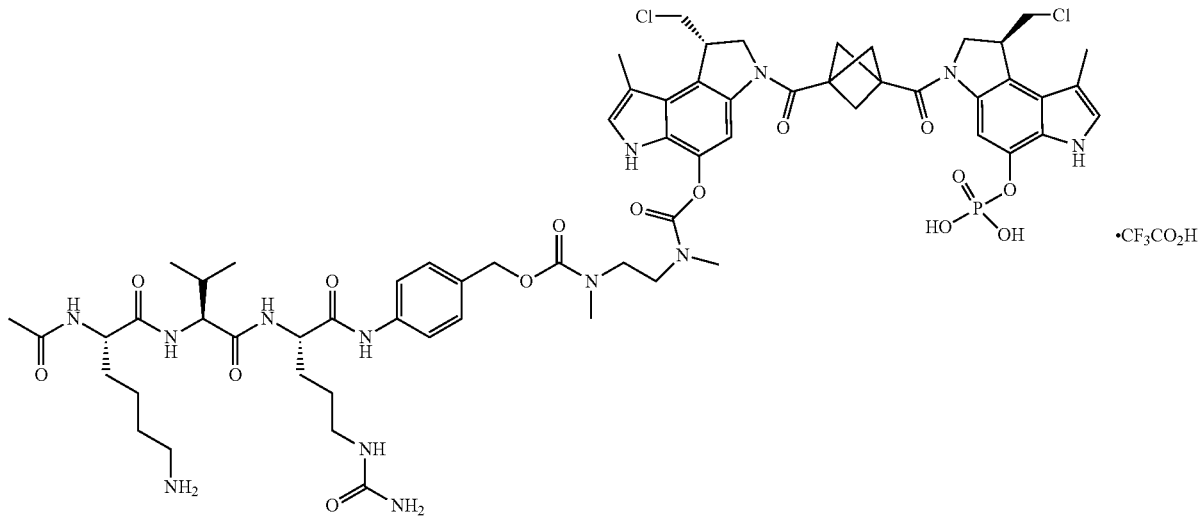 [SMILES: CC(=O)N[C@@H](CCCCN)C(=O)N[C@H](C(=O)N[C@@H](CCCNC(N)=O)C(=O)Nc1ccc(COC(=O)N(C)CCN(C)C(=O)Oc2cc3c(c4c(C)c[nH]c24)[C@H](CCl)CN3C(=O)C23CC(C(=O)N4C[C@@H](CCl)c5c4cc(OP(=O)(O)O)c4[nH]cc(C)c54)(C2)C3)cc1)C(C)C ; "·CF3CO2H"]

The formula for the trifluoroacetic acid salt form above is C63H82Cl2N13O15P.C2HF3O2.

In some embodiments, the ADC is 1) antibody-LLQG (SEQ ID NO: 78)-Ac-Lys-Val-Cit-PABC-CPI-8314. In some embodiments, the acyl donor glutamine-containing tag comprising, e.g., LLQG (SEQ ID NO: 78) which replaces amino acid residues E294-N297 in the antibody heavy chain. In some embodiments, the ADC comprises an amino acid modification at position K222 (in the hinge). In some embodiments, the modification is K222R. Examples of the antibody include, but are not limited to, h18G3, 18G3, h18G3, 16D6, h16D6, 3D1, and 20D7.

In some embodiments, the invention encompasses compositions, including pharmaceutical compositions, comprising antibodies or ADCs described herein or made by the methods and having the characteristics described herein. As used herein, compositions comprise one or more antibodies or ADCs that bind to CD123. These compositions may further comprise suitable excipients, such as pharmaceutically acceptable excipients including buffers, which are well known in the art.

Methods of Using the CD123 Antibodies and the ADCs Thereof

The antibodies and the ADCs of the present invention are useful in various applications including, but are not limited to, therapeutic treatment methods and diagnostic treatment methods.

In one aspect, the invention provides a method for treating a condition associated with CD123 expression in a subject. In some embodiments, the method of treating a condition associated with CD123 expression in a subject comprises administering to the subject in need thereof an effective amount of a composition (e.g., pharmaceutical composition) comprising the CD123 antibodies or the CD123 ADCs as described herein. The conditions associated with CD123 expression include, but are not limited to, abnormal CD123 expression, altered or aberrant CD123 expression, malignant cells expressing CD123, and a proliferative disorder (e.g., cancer) or autoimmune disorder.

Accordingly, in some embodiments, provided is a method of treating a cancer in a subject comprising administering to the subject in need thereof an effective amount of a composition comprising the CD123 antibodies or the CD123 ADCs as described herein. As used herein, cancer can be, for example without limitation, multiple myeloma, malignant plasma cell neoplasm, Hodgkin's lymphoma, nodular lymphocyte predominant Hodgkin's lymphoma, Kahler's disease and Myelomatosis, plasma cell leukemia, plasmacytoma, B-cell prolymphocytic leukemia, hairy cell leukemia (HCL), B-cell non-Hodgkin's lymphoma (NHL), acute myeloid leukemia (AML), chronic lymphocytic leukemia (CLL), acute lymphocytic leukemia (ALL, B-ALL), chronic myeloid leukemia (CML), follicular lymphoma, Burkitt's lymphoma, marginal zone lymphoma, mantle cell lymphoma, large cell lymphoma, precursor B-lymphoblastic lymphoma, Blastic Plasmacytoid Dendritic Cell Neoplasm (BPDCN), myeloid leukemia, Waldenstrom's macroglobulienemia, diffuse large B cell lymphoma, follicular lymphoma, marginal zone lymphoma, mucosa-associated lymphatic tissue lymphoma, small cell lymphocytic lymphoma, mantle cell lymphoma, Burkitt lymphoma, primary mediastinal (thymic) large B-cell lymphoma, lymphoplasmactyic lymphoma, Waldenstrom macroglobulinemia, nodal marginal zone B cell lymphoma, splenic marginal zone lymphoma, intravascular large B-cell lymphoma, primary effusion lymphoma, lymphomatoid granulomatosis, T cell/histiocyte-rich large B-cell lymphoma, primary central nervous system lymphoma, primary cutaneous diffuse large B-cell lymphoma (leg type), EBV positive diffuse large B-cell lymphoma of the elderly, diffuse large B-cell lymphoma associated with inflammation, intravascular large B-cell lymphoma, ALK-positive large B-cell lymphoma, plasmablastic lymphoma, large B-cell lymphoma arising in HHV8-associated multicentric Castleman disease, B-cell lymphoma unclassified with features intermediate between diffuse large B-cell lymphoma and Burkitt lymphoma, B-cell lymphoma unclassified with features intermediate between diffuse large B-cell lymphoma and classical Hodgkin lymphoma, and other B-cell related lymphoma. In some embodiments, the cancer is AML, B-ALL, BPDCN, NHL, or HCL.

In some embodiments, provided is a method of inhibiting tumor growth or progression in a subject who has malignant cells expressing CD123, comprising administering to the subject in need thereof an effective amount of a composition comprising the CD123 antibodies or the CD123 ADCs as described herein. In other embodiments, provided is a method of inhibiting metastasis cells expressing CD123 in a subject, comprising administering to the subject in need thereof an effective amount of a composition comprising the CD123 antibodies or the CD123 ADCs as described herein. In other embodiments, provided is a method of inducing tumor regression in malignant cells in a subject, comprising administering to the subject in need thereof an effective amount of a composition comprising the CD123 antibodies or the CD123 ADCs as described herein.

In some embodiments, provided is a method of treating an autoimmune disorder in a subject comprising administering to the subject in need thereof an effective amount of a composition comprising the CD123 antibodies or the CD123 ADCs as described herein.

As used herein, autoimmune disorders include, but are not limited to, systemic lupus erythematosus, rheumatoid arthritis, diabetes (Type I), multiple sclerosis, Addison's disease, celiac disease, dermatomyositis, Graves' disease, hashimoto's thyroiditis, hashimoto's encephalopathy, Myasthenia gravis, pernicious anemia, reactive arthritis, Sjogren syndrome, acute disseminated encephalomyelitis, agammaglobulinemia, amyotrophic lateral sclerosis, ankylosing spondylitis, antiphospholipid syndrome, antisynthetase syndrome, atopic allergy, atopic dermatitis, autoimmune enteropathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendorcrine syndrome, autoimmune progesterone dermatitis, autoimmune thrombocytopenic purpura, autoimmune urticarial, autoimmune uveitis, Bechet's disease, Castleman's disease, cold agglutinin disease, Crohn's disease, dermatomyositis, eosinophilic fasciitis, gastrointestinal pemphigoid, Goodpasture's syndrome, Guillain-Barré syndrome, hidradenitis suppurativa, idiopathic thrombocytopenic purpura, narcolepsy, pemphigus vulgaris, pernicious anaemia, polymyositis, primary billary cirrhosis, relapsing polychrondritis, rheumatic fever, temporal arteritis, transverse myelitis, ulcerative colitis, undifferentiated connective tissue disease, vasculitis, and Wegener's granulomatosis.

In another aspect, the invention provides an effective amount of a composition (e.g., pharmaceutical composition) comprising the CD123 antibodies or the CD123 ADCs as described herein for treating a condition (e.g., cancer or autoimmune disorder) associated with CD123 expression in a subject in need thereof. In some embodiments, provided is an effective amount of a composition (e.g., pharmaceutical composition) comprising the CD123 antibodies or the CD123 ADCs as described herein for inhibiting tumor growth or progression in a subject who has malignant cells expressing CD123. In some embodiments, provided is an effective amount of a composition (e.g., pharmaceutical composition) comprising the CD123 antibodies or the CD123 ADCs as described herein for inhibiting metastasis of malignant cells expressing CD123 in a subject in need thereof. In some embodiments, provided is an effective amount of a composition (e.g., pharmaceutical composition) comprising the CD123 antibodies or the CD123 ADCs as described herein for inducing tumor regression in a subject who has malignant cells expressing CD123.

In another aspect, the invention provides the CD123 antibodies or the CD123 ADCs as described herein for use in treating a condition (e.g., cancer or autoimmune disorder) associated with CD123 expression in a subject in need thereof. In some embodiments, provided is the CD123 antibodies or the CD123 ADCs as described herein for inhibiting tumor growth or progression in a subject who has malignant cells expressing CD123. In some embodiments, provided is the CD123 antibodies or the CD123 ADCs as described herein for inhibiting metastasis of malignant cells expressing CD123 in a subject in need thereof. In some embodiments, provided is the CD123 antibodies or the CD123 ADCs as described herein for inducing tumor regression in a subject who has malignant cells expressing CD123.

In another aspect, the invention provides a use of the CD123 antibodies or the CD123 ADCs as described herein in the manufacture of a medicament for treating a condition (e.g., cancer or autoimmune disorder) associated with CD123 expression. In some embodiments, provided is a use of the CD123 antibodies or the CD123 ADCs as described herein in the manufacture of a medicament for inhibiting tumor growth or progression. In some embodiments, provided is a use of the CD123 antibodies or the CD123 ADCs as described herein in the manufacture of a medicament for inhibiting metastasis of malignant cells expressing CD123. In some embodiments, provided is a use of the CD123 antibodies or the CD123 ADCs as described herein in the manufacture of a medicament for inducing tumor regression.

In another aspect, provided is a method of detecting, diagnosing, and/or monitoring a condition associated with CD123 expression. For example, the CD123 antibodies as described herein can be labeled with a detectable moiety such as an imaging agent and an enzyme-substrate label. The antibodies as described herein can also be used for in vivo diagnostic assays, such as in vivo imaging (e.g., PET or SPECT), or a staining reagent.

In some embodiments, the methods described herein further comprise a step of treating a subject with an additional form of therapy. In some embodiments, the additional form of therapy is an additional anti-cancer therapy including, but not limited to, chemotherapy, radiation, surgery, hormone therapy, and/or additional immunotherapy.

In some embodiments, the additional form of therapy comprises administering one or more therapeutic agent in addition to the CD123 antibodies or the CD123 ADCs as described herein. The one or more therapeutic agent can be e.g., but not limited to, a second antibody (e.g., an anti-VEGF (Vascular Endothelial Growth Factor) antibody (e.g., AVASTIN®), an anti-HER2 antibody (e.g., HERCEPTIN®), an anti-CD25 antibody, an anti-CD33 antibody, an anti-CD20 antibody (e.g., RITUXAN®), an anti-mucin-like glycoprotein antibody, an anti-TNF antibody, an anti-PD-1 or PD-L1 antibody, and/or an epidermal growth factor receptor (EGFR) antibody (e.g., ERBITUX®)), an angiogenesis inhibitor, a cytotoxic agent (e.g., anthracyclines (e.g., daunorubicin, doxorubicin, epirubicin, idarubicin, valrubicin, and mitoxantrone), taxane (e.g., paclitaxel and docetaxel), dolastatin, duocarmycin, enediyne, geldanamycin, maytansine, puromycin, vinca alkaloid (e.g., vincristine), a topoisomerase inhibitor (e.g., etoposide), tubulysin, a pyrimidine analog (e.g., fluorouracil), platinum-containing agents (e.g., cisplatin, carboplatin, and oxaliplatin), alkylating agents (e.g., melphalan, cyclophosphamide, or carmustine) and hemiasterlin), immunomodulating agent (e.g., prednisone), an anti-inflammatory agent (e.g., dexamethasone), an aromatase inhibitor (e.g., anastrozole, exemestane, letrozole, vorozole, formestane, or testolactone), a proteasome inhibitor (e.g., bortezomib such as VELCADE® ([(1R)-3-methyl-1-[[(2S)-1-oxo-3-phenyl-2-[(pyrazinylcarbonyl)amino]propyl]amino]butyl] boronic acid), and other agents such as tamoxifen.

For example, in some embodiments, provided is a method of treating AML comprising administering to a subject need thereof an effective amount of a composition comprising the CD123 antibodies or the CD123 ADCs as described herein and one other therapeutic agent such as a chemotherapeutic agent or thalidomide or its derivative thereof (e.g., lenalidomide). In some embodiments, the one other therapeutic agent is selecting from the group consisting of bortezomib (e.g., VELCADE®), melphalan, prednisone, doxorubicin, lenalidomide, thalidomide, prednisone, carmustine, etoposide, cisplatin, cyclophosphamide, and vincristine. In some embodiments, the other therapeutic agent is bortezomib (e.g., VELCADE®), melphalan, or prednisone. In some embodiments, the subject is relapsing or refractory to previous AML therapy.

The CD123 antibody or the CD123 ADCs can be administered to an individual via any suitable route. It should be understood by persons skilled in the art that the examples described herein are not intended to be limiting but to be illustrative of the techniques available. Accordingly, in some embodiments, the CD123 antibody or the CD123 ADC is administered to an individual in accord with known methods, such as intravenous administration, e.g., as a bolus or by continuous infusion over a period of time, by intramuscular, intraperitoneal, intracerebrospinal, intracranial, transdermal, subcutaneous, intra-articular, sublingually, intrasynovial, via insufflation, intrathecal, oral, inhalation or topical routes. Administration can be systemic, e.g., intravenous administration, or localized. Commercially available nebulizers for liquid formulations, including jet nebulizers and ultrasonic nebulizers are useful for administration. Liquid formulations can be directly nebulized and lyophilized powder can be nebulized after reconstitution. Alternatively, the CD123 antibody or the CD123 ADC can be aerosolized using a fluorocarbon formulation and a metered dose inhaler, or inhaled as a lyophilized and milled powder.

In one embodiment, the CD123 antibody or the CD123 ADC is administered via site-specific or targeted local delivery techniques. Examples of site-specific or targeted local delivery techniques include various implantable depot sources of the Trop antibody or the CD123 ADC or local delivery catheters, such as infusion catheters, indwelling catheters, or needle catheters, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Various formulations of the CD123 antibody or the CD123 ADC may be used for administration. In some embodiments, the CD123 antibody or the CD123 ADC may be administered neat. In some embodiments, of the CD123 antibody (or the CD123 ADC) and a pharmaceutically acceptable excipient may be in various formulations. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington, The Science and Practice of Pharmacy 21st Ed. Mack Publishing, 2005.

In some embodiments, these agents are formulated for administration by injection (e.g., intraperitoneally, intravenously, subcutaneously, intramuscularly, etc.). Accordingly, these agents can be combined with pharmaceutically acceptable vehicles such as saline, Ringer's solution, dextrose solution, and the like. The particular dosage regimen, i.e., dose, timing and repetition, will depend on the particular individual and that individual's medical history.

CD123 antibodies or the CD123 ADCs as described herein can be administered using any suitable method, including by injection (e.g., intraperitoneally, intravenously, subcutaneously, intramuscularly, etc.). The CD123 antibody or the CD123 ADC can also be administered via inhalation, as described herein. Generally, for administration of a CD123 antibody and a CD123 ADC, an initial candidate dosage can be about 2 mg/kg. For the purpose of the present invention, a typical daily dosage might range from about any of 3 µg/kg to 30 µg/kg to 300 µg/kg to 3 mg/kg, to 30 mg/kg, to 100 mg/kg or more, depending on the factors mentioned above. For example, dosage of about 1 mg/kg, about 2.5 mg/kg, about 5 mg/kg, about 10 mg/kg, and about 25 mg/kg may be used. For repeated administrations over several days or longer, depending on the condition, the treatment is sustained until a desired suppression of symptoms occurs or until sufficient therapeutic levels are achieved, for example, to inhibit or delay tumor growth/progression or metatstasis of cancer cells. One exemplary dosing regimen comprises administering an initial dose of about 2 mg/kg, followed by a weekly maintenance dose of about 1 mg/kg of the CD123 antibody or CD123 ADC, or followed by a maintenance dose of about 1 mg/kg every other week. Another exemplary dosing regimen comprises administering an initial dose of about 0.21, about 0.5, or about 0.8 mg/kg every week or every three weeks. Other exemplary dosing regimen comprises administering increasing doses (e.g., initial dose of 1 mg/kg and gradual increase to one or more higher doses every week or longer time period). Other dosage regimens may also be useful, depending on the pattern of pharmacokinetic decay that the practitioner wishes to achieve. For example, in some embodiments, dosing from one to four times a week is contemplated. In other embodiments dosing once a month or once every other month or every three months is contemplated. The progress of this therapy is easily monitored by conventional techniques and assays. The dosing regimen (including the CD123 antibody or the CD123 ADC used) can vary over time.

For the purpose of the present invention, the appropriate dosage of a CD123 antibody or a CD123 ADC will depend on the CD123 antibody or the CD123 ADC (or compositions thereof) employed, the type and severity of symptoms to be treated, whether the agent is administered for therapeutic purposes, previous therapy, the subject's clinical history and response to the agent, the subject's clearance rate for the administered agent, and the discretion of the attending physician. Typically the clinician will administer a CD123 antibody or a CD123 ADC until a dosage is reached that achieves the desired result. Dose and/or frequency can vary over course of treatment. Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of symptoms, e.g., tumor growth inhibition or delay, etc. Alternatively, sustained continuous release formulations of CD123 antibodies or CD123 ADCs may be appropriate. Various formulations and devices for achieving sustained release are known in the art.

In one embodiment, dosages for a CD123 antibody or a CD123 ADC may be determined empirically in individuals who have been given one or more administration(s) of the CD123 antibody or its CD123 ADC. Individuals are given incremental dosages of a CD123 antibody or a CD123 antagonist. To assess efficacy, an indicator of the disease can be followed.

Administration of a CD123 antibody or an CD123 ADC in accordance with the method in the present invention can be continuous or intermittent, depending, for example, upon the recipient's physiological condition, whether the purpose of the administration is therapeutic or prophylactic, and other factors known to skilled practitioners. The administration of a CD123 antibody or a CD123 ADC may be essentially continuous over a preselected period of time or may be in a series of spaced doses.

In some embodiments, more than one CD123 antibody or CD123 ADC may be present. At least one, at least two, at least three, at least four, at least five different or more CD123 antibody or CD123 ADC can be present. Generally, those CD123 antibodies or CD123 ADCs may have complementary activities that do not adversely affect each other. For example, one or more of the following CD123 antibody may be used: a first CD123 antibody directed to one epitope on CD123 and a second CD123 antibody directed to a different epitope on CD123.

Therapeutic formulations of the CD123 antibody or the CD123 ADC used in accordance with the present invention are prepared for storage by mixing an antibody having the desired degree of purity with optional pharmaceutically acceptable carriers, excipients or stabilizers (Remington, The Science and Practice of Pharmacy 21st Ed. Mack Publishing, 2005), in the form of lyophilized formulations or aqueous solutions. Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Liposomes containing the CD123 antibody or the CD123 ADC are prepared by methods known in the art, such as described in Epstein, et al., Proc. Natl. Acad. Sci. USA 82:3688, 1985; Hwang, et al., Proc. Natl Acad. Sci. USA 77:4030, 1980; and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington, The Science and Practice of Pharmacy 21st Ed. Mack Publishing, 2005.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or 'poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The formulations to be used for in vivo administration must be sterile. This is readily accomplished by, for example, filtration through sterile filtration membranes. Therapeutic CD123 antibody or CD123 ADC compositions are generally placed into a container having a sterile access port, for example, an intravenous solution bag or vial having a stopper pierceable by a hypodermic injection needle.

The compositions according to the present invention may be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 µm, particularly 0.1 and 0.5 µm, and have a pH in the range of 5.5 to 8.0.

The emulsion compositions can be those prepared by mixing a CD123 antibody or a CD123 ADC with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Compositions

The compositions used in the methods of the invention comprise an effective amount of a CD123 antibody or a CD123 ADC as described herein. Examples of such compositions, as well as how to formulate, are also described in an earlier section and below. In some embodiments, the composition comprises one or more CD123 antibodies or CD123 ADCs. For example, CD123 antibody recognizes human CD123. In some embodiments, the CD123 antibody is a human antibody, a humanized antibody, or a chimeric antibody. In some embodiments, the CD123 antibody comprises a constant region that is capable of triggering a desired immune response, such as antibody-mediated lysis or ADCC. In other embodiments, the CD123 antibody comprises a constant region that does not trigger an unwanted or undesirable immune response, such as antibody-mediated lysis or ADCC. In other embodiments, the CD123 antibody comprises one or more CDR(s) of the antibody (such as one, two, three, four, five, or, in some embodiments, all six CDRs).

It is understood that the compositions can comprise more than one CD123 antibody or CD123 ADC (e.g., a mixture of CD123 antibodies that recognize different epitopes of CD123). Other exemplary compositions comprise more than one CD123 antibody or CD123 ADC that recognize the same epitope(s), or different species of CD123 antibodies or CD123 ADC that bind to different epitopes of CD123 (e.g., human CD123).

In some embodiments, the CD123 antibody may be administered in combination with the administration of one or more additional therapeutic agents. These include, but are not limited to, the administration of a chemotherapeutic agent, a vaccine, a CAR-T cell-based therapy, radiotherapy, a cytokine therapy, a vaccine, a CD123 bispecific antibody, an inhibitor of other immunosuppressive pathways, an inhibitors of angiogenesis, a T cell activator, an inhibitor of a metabolic pathway, an mTOR inhibitor, an inhibitor of an adenosine pathway, a tyrosine kinase inhibitor including but not limited to inlyta, ALK inhibitors and sunitinib, a BRAF inhibitor, an epigenetic modifier, an IDO1 inhibitor, an inhibitor or depleter of Treg cells and/or of myeloid-derived suppressor cells, a JAK inhibitor, a STAT inhibitor, a cyclin-dependent kinase inhibitor, a biotherapeutic agent (including but not limited to antibodies to VEGF, VEGFR, EGFR, Her2/neu, other growth factor receptors, CD20, CD40, CD-40L, CTLA-4, OX-40, 4-1BB, CD123, PD-L1, TIGIT, and ICOS), an immunogenic agent (for example, attenuated cancerous cells, tumor antigens, antigen presenting cells such as dendritic cells pulsed with tumor derived antigen or nucleic acids, immune stimulating cytokines (for example, IL-2, IFNα2, GM-CSF), and cells transfected with genes encoding immune stimulating cytokines such as but not limited to GM-CSF). Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin gamma1I and calicheamicin phi1I, see, e.g., Agnew, Chem. Intl. Ed. Engl., 33:183-186 (1994); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, and deoxydoxorubicin), pegylated liposomal doxorubicin, epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; razoxane; rhizoxin; sizofuran; spirogermanium; tenuazonic acid; triaziquone; 2,2′,2″-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel and doxetaxel; chlorambucil; gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above. Also included are anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY117018, onapristone, and toremifene (Fareston); aromatase inhibitors that inhibit the enzyme aromatase, which regulates estrogen production in the adrenal glands, such as, for example, 4(5)-imidazoles, aminoglutethimide, megestrol acetate, exemestane, formestane, fadrozole, vorozole, letrozole, and anastrozole; and anti-androgens such as flutamide, nilutamide, bicalutamide, leuprolide, and goserelin; and pharmaceutically acceptable salts, acids or derivatives of any of the above.

In some embodiments, a CD123 antibody is used in conjunction with one or more other therapeutic agents targeting an immune checkpoint modulator, such as, for example without limitation, an agent targeting CD123, PD-1, PD-L1, CTLA-4, LAG-3, B7-H3, B7-H4, B7-DC (PD-L2), B7-H5, B7-H6, B7-H8, B7-H2, B7-1, B7-2, ICOS, ICOS-L, TIGIT, CD2, CD47, CD80, CD86, CD48, CD58, CD226, CD155, CD112, LAIR1, 2B4, BTLA, CD160, TIM1, TIM-3, TIM4, VISTA (PD-H1), OX40, OX40L, GITR, GITRL, CD70, CD27, 4-1BB, 4-BBL, DR3, TL1A, CD40, CD40L, CD30, CD30L, LIGHT, HVEM, SLAM (SLAMF1, CD150), SLAMF2 (CD48), SLAMF3 (CD229), SLAMF4 (2B4, CD244), SLAMF5 (CD84), SLAMF6

(NTB-A), SLAMCF7 (CS1), SLAMF8 (BLAME), SLAMF9 (CD2F), CD28, CEACAM1 (CD66a), CEACAM3, CEACAM4, CEACAM5, CEACAM6, CEACAM7, CEACAM8, CEACAM1-3AS CEACAM3C2, CEACAM1-15, PSG1-11, CEACAM1-4C1, CEACAM1-4S, CEACAM1-4L, IDO, TDO, CCR2, CD39-CD73-adenosine pathway (A2AR), BTKs, TIKs, CXCR2, CCR4, CCR8, CCR5, VEGF pathway, CSF-1, or an innate immune response modulator. In some embodiments, a CD123 antibody is used in conjunction with, for example, an anti-PD-L1 antagonist antibody such as, for example, BMS-936559 (MDX-1105; a CD123 antibody such as for example, nivolumab, pembrolizumab, and pidilizumab; an anti-CTLA-4 antagonist antibody such as for example ipilimumab; an anti-LAG-3 antagonist antibody such as BMS-986016 and IMP701; an anti-TIM-3 antagonist antibody; an anti-B7-H3 antagonist antibody such as for example MGA271; an-anti-VISTA antagonist antibody; an anti-TIGIT antagonist antibody; an anti-CD28 antagonist antibody; an anti-CD80 antibody; an anti-CD86 antibody; an-anti-B7-H4 antagonist antibody; an anti-ICOS agonist antibody; an anti-CD28 agonist antibody; an innate immune response modulator (e.g., TLRs, KIR, NKG2A), and an IDO inhibitor. In some embodiments, a CD123 antibody is used in conjunction with a 4-1BB (CD137) agonist such as, for example, PF-05082566 or BMS-663513. In some embodiments, a CD123 antibody is used in conjunction with an OX40 agonist such as, for example, an anti-OX-40 agonist antibody. In some embodiments, a CD123 antibody is used in conjunction with a GITR agonist such as, for example, an-anti-GITR agonist antibody such as, for example without limitation, TRX518. In some embodiments, a CD123 antibody is used in conjunction with an IDO inhibitor. In some embodiments, a CD123 antibody is used in conjunction with a cytokine therapy such as, for example without limitation, IL-15, CSF-1, MCSF-1, etc.

In some embodiments, a CD123 antibody is used in conjunction with one or more other therapeutic antibodies, such as, for example without limitation, an antibody targeting CD19, CD22, CD40, CD52, or CCR4.

In some embodiments, the CD123 antibody therapy may precede or follow the other agent treatment by intervals ranging from minutes to weeks. In embodiments where the other agents and/or a proteins or polynucleotides are administered separately, one would generally ensure that a significant period of time did not expire between each delivery, such that the agent and the composition of the present invention would still be able to exert an advantageously combined effect on the subject. In such instances, it is contemplated that one may administer both modalities within about 12-24 h of each other and, more preferably, within about 6-12 h of each other. In some situations, it may be desirable to extend the time period for administration significantly, however, where several days (2, 3, 4, 5, 6 or 7) to several weeks (1, 2, 3, 4, 5, 6, 7 or 8) lapse between the respective administrations.

In some embodiments, a CD123 antibody composition comprises a second agent selected from crizotinib, palbociclib, gemcitabine, cyclophosphamide, fluorouracil, FOLFOX, folinic acid, oxaliplatin, axitinib, sunitinib malate, tofacitinib, bevacizumab, rituximab, and traztuzumab.

In some embodiments, a CD123 antibody composition is combined with a treatment regimen further comprising a traditional therapy selected from the group consisting of: surgery, radiation therapy, chemotherapy, targeted therapy, immunotherapy, hormonal therapy, angiogenesis inhibition and palliative care.

The composition used in the present invention can further comprise pharmaceutically acceptable carriers, excipients, or stabilizers (Remington: The Science and practice of Pharmacy 21st Ed., 2005, Lippincott Williams and Wilkins, Ed. K. E. Hoover), in the form of lyophilized formulations or aqueous solutions. Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

Polynucleotides, Vectors, and Host Cells

The invention also provides isolated polynucleotides encoding the antibodies of the invention, and vectors and host cells comprising the polynucleotide. In another aspect, the invention provides compositions (such as a pharmaceutical compositions) comprising any of the polynucleotides of the invention. In some embodiments, the composition comprises an expression vector comprising a polynucleotide encoding any of the antibodies described herein. In another aspect, the invention provides a method of making any of the polynucleotides described herein.

Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an antibody or a portion thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants preferably exhibit at least about 70% identity, more preferably, at least about 80% identity, yet more preferably, at least about 90% identity, and most preferably, at least about 95% identity to a polynucleotide sequence that encodes a native antibody or a portion thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J., 1990, Unified Approach to Alignment and Phylogenes pp. 626-645 Methods in Enzymology vol. 183, Academic Press, Inc., San Diego, Calif.; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, Calif.; Wilbur, W. J. and Lipman, D. J., 1983, Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/ 0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The invention also provides host cells comprising any of the polynucleotides described herein. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as *E. coli* or *B. subtillis*) and yeast (such as *S. cerevisae, S. pombe*; or *K. lactis*). Preferably, the host cells express the cDNAs at a level of about 5 fold higher, more preferably, 10 fold higher, even more preferably, 20 fold higher than that of the corresponding endogenous antibody or protein of interest, if present, in the host cells. Screening the host cells for a specific binding to CD123 is effected by an immunoassay or FACS. A cell overexpressing the antibody or protein of interest can be identified.

Kits

The invention also provides kits for use in the instant methods. Kits of the invention include one or more containers comprising the CD123 antibody or the CD123 ADC as described herein and instructions for use in accordance with any of the methods of the invention described herein. Generally, these instructions comprise a description of administration of the CD123 antibody or the CD123 ADC for the above described therapeutic treatments.

The instructions relating to the use of the CD123 antibodies or the CD123 ADCs as described herein generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is a CD123 antibody. The container may further comprise a second pharmaceutically active agent.

Kits may optionally provide additional components such as buffers and interpretive information. Normally, the kit comprises a container and a label or package insert(s) on or associated with the container.

Biological Deposit

Representative materials of the present invention were deposited in the American Type Culture Collection (ATCC) on Jun. 29, 2017. Vector having ATCC Accession No. PTA-124283 is a polynucleotide encoding a humanized CD123 antibody heavy chain sequence, and vector having ATCC Accession No. PTA-124284 is a polynucleotide encoding a humanized CD123 antibody light chain sequence. The deposits were made under the provisions of the Budapest Treaty on the International Recognition of the Deposit of Microorganisms for the Purpose of Patent Procedure and Regulations thereunder (Budapest Treaty). This assures maintenance of a viable culture of the deposit for 30 years from the date of deposit. The deposit will be made available by ATCC under the terms of the Budapest Treaty, and subject to an agreement between Pfizer Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. Section 122 and the Commissioner's rules pursuant thereto (including 37 C.F.R. Section 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

EXAMPLES

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

Example 1: In Vitro Cytotoxicity of CD123 Antibody-Drug Conjugates

This Example illustrates the cytotoxicity of various CD123 ADCs.

In this study, cytotoxicity of various CD123 ADCs was tested using a 2D in vitro cytotoxicity assay in the following AML cell lines: MOLM13, MV411, JVM3, Granata519, OCI-AML3, NB4, and HL60. Table 4 indicates the expression level of CD123 for each of the respective cells used.

TABLE 4

Expression level of CD123 in various AML cell lines.

| | Cell Line | | | | | | |
|---|---|---|---|---|---|---|---|
| | MOLM13 | MV411 | JVM3 | Granta519 | OCI-AML3 | NB4 | HL60 |
| CD123 Expression Level | +++ | +++ | ++ | ++ | + | + | − |

The first group of ADCs tested were CD123 ADC conjugated to CPI with an AcLysValCitPABC linker. These ADCs were: 18G3-CPI, 16D6-CPI, 3D1-CPI, and 20D7-CPI, each of which have a Drug:Antibody Ratio (DAR) of ~2. The preparation of CD123 ADCs is described in detail in Example 5, infra. A control IgG (IgG which does not bind to CD123) with CPI agent with a DAR of ~2 ("Neg.8.8") was used as a negative control.

For the 2D in vitro cytotoxicity assay, AML cells were incubated with ADC or control at the following doses: 100 ng/ml, 25 ng/ml, 6.25 ng/ml, 1.56 ng/ml, 0.39 ng/ml, 0.09 ng/ml, 0.024 ng/ml, 0.006 ng/ml, 0.002 ng/ml and 0.0004 ng/ml. for 96 hours. Cell viability was measured with CelltiterGlo (Promega, Madison, Wis.), and luminescence was determined using a Victor plate reader (Perkin Elmer, Waltham, Mass.). 50% inhibition value (IC50) calculations were generated using XLfit (IDBS, Boston, Mass.) 4 parameter curve fit. The results are summarized in Table 5.

TABLE 5

IC50 values of CD123-CPI ADC in AML cells.

| | IC50 (ng/mL) in AML cells | | | | | | |
|---|---|---|---|---|---|---|---|
| ADC | MOLM13 | MV411 | JVM3 | Granta519 | OCI-AML3 | NB4 | HL60 |
| 18G3-CPI | 0.25 ± 0.04 | 0.41 ± 0.07 | 0.69 ± 0.22 | 0.38 ± 0.01 | 2.65 ± 0.12 | 63.92 ± 36.08 | >84.4 ± 33.30 |
| 16D6-CPI | 0.22 ± 0.05 | 0.4 ± 0.15 | 0.59 ± 0.24 | — | — | — | >105.34 ± 94.66 |
| 3D1-CPI | 0.33 ± 0.06 | — | — | — | — | — | >104.68 ± 95.32 |
| 20D7-CPI | 0.32 ± 0.14 | — | — | — | — | — | — |
| Neg.8.8-CPI | >88.43 ± 18.66 | >90.82 ± 8.64 | >77 ± 14.3 | >87.85 ± 12.14 | >100 ± 0 | >100 ± 0 | >113.43 ± 19.09 |

The results show that CD123-CPIs are cytotoxic to cells that express CD123, and they are more cytotoxic than a nonspecific CP1 (Neg8.8-CPI). For example, in MOLM13 cells, the IC50 of CD123 ADCs 18G3-CPI, 16D6-CPI, and 3D1-CPI are 0.25±0.04 ng/mL, 0.22±0.05 ng/mL, 0.33±0.06 ng/mL, and 0.32±0.14 ng/mL, respectively. In contrast, the IC50 of Neg.8.8-CPI was >88.43±18.66 (Table 5, last row). Neg.8.8-CPI with a DAR of ~2 was substantially less active at the highest doses tested (Table 5, last row). IC50 values of the indicated CD123 ADCs correlate well with the level of CD123 expression on cells (Tables 4 and 5). For example, IC50 of 18G3-CPI in MV411 cells which express high levels of CD123, is 0.41±0.07. In contrast, IC50 of 18G3-CPI in NB4 cells which express low levels of CD123, is 63.92±36.08, and IC50 of 18G3-CPI in HL60 cells which do not express CD123, is >84.4±33.30.

CD123-18G3 ADC was conjugated to a different agent, either iPr-calicheamicin or CTI (glucuronide) has a similar cytotoxic effect. Cytotoxicity assay results for 18G3 conjugated to iPr-calicheamicin ("iPr") are summarized in Table 6. Cytotoxicity assay results for 18G3 conjugated to CTI (glucuronide) are summarized in Table 7.

TABLE 6

IC50 values of CD123-iPr ADC in AML cells.

| | IC50 (ng/mL) in AML cells | |
| --- | --- | --- |
| Cell line | MOLM13 | MV4-11 |
| CD123 Expression Level | +++ | +++ |
| 18G 3-iPr | 0.05075 ± 0.01 | 0.125 ± 0.06 |
| Neg 8.8-iPr | 96.23 | >100 |

The cytotoxicities of CD123-18G3-CPI and CD123-16D6-CPI are still maintained in the presence of IL-3 (Table 8).

TABLE 8

| | IL-3 | IC50 (ng/mL) in AML cells | | |
| --- | --- | --- | --- | --- |
| Cell line | (ng/ml) | Neg.8.8-CPI | CD123-18G3-CPI | CD123-16D6-CPI |
| MOLM13 | 0 | 44.24 ± 0.0 | 0.14 ± 0.0 | 0.23 ± 0.0 |
| MOLM13 | 0.3 | 42.93 ± 0.0 | 0.12 ± 0.0 | 0.23 ± 0.0 |
| MOLM13 | 1 | 28.38 ± 0.0 | 0.14 ± 0.0 | 0.19 ± 0.0 |
| MV4-11 | 0 | >200 | 1.07 ± 0.0 | 1.25 ± 0.0 |
| MV4-11 | 0.3 | >200 | 1.05 ± 0.0 | 1.13 ± 0.0 |
| MV4-11 | 1 | >200 | 0.21 ± 0.0 | 1.13 ± 0.0 |

TABLE 7

IC50 values of CD123-CTI ADC in AML cells.

| | IC50 (ng/mL) in AML cells | | | | | | |
| --- | --- | --- | --- | --- | --- | --- | --- |
| Cell line | MOLM13 | MV411 | Granta519 | JVM3 | OCI-AML3 | NB4 | HL60 |
| CD123 Expression Level | +++ | +++ | ++ | ++ | + | + | − |
| 18G3-CTI | 0.33 ± 0.05 | 0.51 ± 0.06 | 0.26 ± 0.04 | 1.3 ± 0.36 | 2.58 ± 0.6 | 38.60 ± 9.18 | >100 ± 0 |
| Neg.8.8-CTI | >100 ± 0 | 84.96 ± 15.04 | >100 ± 0 | >100 ± 0 | >100 ± 0 | >100 ± 0 | >100 ± 0 |

These data demonstrate that CD123-ADCs with a DAR of ~2 are active and induce cell death in CD123-expressing cancer cell lines, but inactive in cells that do not express CD123. This demonstrates the potency and specificity of these ADCs.

Example 2: Interleukin-3 (IL-3) Signaling Pathway and Cytotoxicity of CD123 Antibodies and ADCs This Example illustrates the ability of CD123 antibodies to block IL-3 signaling, and cytotoxicity of CD123 ADCs.

This study was conducted to determine if any of the CD123 antibody clones competitively bind to IL-3 binding sites in CD123/IL-3Rα-expressing TF-1 cells. CD123/IL-3Rα-expressing TF-1 cells were co-incubated with 20 ng/ml of IL-3 and the following CD123 antibodies: 3D1, 18G3, and 16D6 with doses at 100 ng/ml, 25 ng/ml, 6.25 ng/ml, 1.56 ng/ml, 0.39 ng/ml, 0.09 ng/ml, 0.024 ng/ml, 0.006 ng/ml, 0.002 ng/ml and 0.0004 ng/ml. CD123 antibody 7G3 was used as a benchmark antibody that has been shown to block IL-3 signaling pathway and Neg 8.8 antibody was used as a negative control. For the CTG assay measuring cell survival, cells were treated for four days at 37° C. After the treatment period, the cells were collected and protein prepared. STAT5, phosphorylated STAT5, and actin levels were analyzed using Western blot analysis. Western blot results are shown in FIG. 1.

The presence of downstream signaling protein phosphorylated STAT5 ("Phospho-Stat5") indicates activation of the IL-3 signaling pathway. Treatment of the TF-1 cells with IL-3 alone, or IL-3 plus Neg.8.8 control antibody ("8.8") activated IL-3 signaling, as shown by the presence of Phospho-Stat5 (FIG. 1). Treatment with CD123 antibody 7G3 blocks the IL-3 signaling. CD123 antibody 3D1 also blocked this pathway. In contrast, CD123 antibodies 18G3 and 16D6 did not block IL-3-mediated STAT5 phosphorylation.

Example 3: In Vivo Efficacy of CD123-ADCs

This Example illustrates the efficacy of CD123 ADCs in vivo.

Anti-tumor activity of CD123 ADCs was tested in vivo using Acute Myeloid Leukemia (AML) cell line xenograft models. For each model described below the first dose was given on Day 0. The tumors were measured at least once a week and their volume was calculated with the formula: tumor volume (mm$^3$)=0.5×(tumor width$^2$)(tumor length). The mean tumor volumes (±S.E.M.) for each treatment group were calculated having 10 animals to be included. All animal experiments were conducted in a facility accredited by the Association for Assessment of Laboratory Animal Care under Institutional Animal Care and Use Committee guidelines and appropriate animal research approval. CD123 ADCs demonstrated a high efficacy in cell lines with assorted gene mutations or overexpressed genes and/or proteins in a dose-dependent manner.

A. H.1 MOLM13 AML Xenografts

The anti-tumor activity of CD123 ADCs was examined in NOD/SCID immunodeficient mice on the in vivo growth of human tumors. For subcutaneous (sc) AML models, 5×10$^6$ MOLM13 cells were implanted subcutaneously in the flank of female mice. When the tumors reached an average volume of 200 mm$^3$, animals were staged to ensure uniformity of the tumor size among various treatment groups. The MOLM13 AML sc xenograft model was dosed intravenously four times every four days (Q4d×4) with PBS vehicle, CD123-CPI (18G3, 16D6, or 3D1) at 0.3 mg/kg or 1 mg/kg, or control Neg-8.8-CPI at 0.3 mg/kg or 1 mg/kg. The data are summarized in Table 9.

TABLE 9

MOLM-13 AML xenografts, mean tumor volume (mm³ +/− SEM) Q4dx4

| | PBS | CD123-CPI | | | | | | Neg 8.8-CPI | |
| | | 18G3-CPI | | 16D6-CPI | | 3D1-CPI | | | |
| DOSE (mg/kg) | 0 | 0.3 | 1 | 0.3 | 1 | 0.3 | 1 | 0.3 | 1 |
|---|---|---|---|---|---|---|---|---|---|
| Day 0 | 248 ± 10 | 251 ± 7 | 250 ± 13 | 241 ± 17 | 248 ± 6 | 249 ± 5 | 247 ± 12 | 252 ± 14 | 246 ± 14 |
| Day 2 | 660 ± 38 | 407 ± 25 | 386 ± 35 | 391 ± 43 | 319 ± 24 | 337 ± 18 | 405 ± 43 | 553 ± 49 | 448 ± 52 |
| Day 5 | 1313 ± 51 | 322 ± 27 | 239 ± 36 | 293 ± 37 | 173 ± 19 | 261 ± 15 | 261 ± 30 | 651 ± 60 | 388 ± 43 |
| Day 9 | 2802 ± 90 | 123 ± 14 | 95 ± 8 | 136 ± 17 | 64 ± 7 | 127 ± 7 | 96 ± 13 | 486 ± 64 | 193 ± 38 |
| Day 12 | — | 16 ± 11 | 0 ± 0 | 28 ± 14 | 0 ± 0 | 20 ± 11 | 0 ± 0 | 374 ± 72 | 83 ± 15 |
| Day 17 | — | 0 ± 0 | 0 ± 0 | 0 ± 0 | 0 ± 0 | 0 ± 0 | 0 ± 0 | 169 ± 67 | 0 ± 0 |
| Day 20 | — | 0 ± 0 | 0 ± 0 | 0 ± 0 | 0 ± 0 | 0 ± 0 | 0 ± 0 | 354 ± 115 | 0 ± 0 |
| Day 25 | — | 0 ± 0 | 0 ± 0 | 0 ± 0 | 0 ± 0 | 0 ± 0 | 0 ± 0 | 1148 ± 307 | 0 ± 0 |
| Day 27 | — | 0 ± 0 | 0 ± 0 | 0 ± 0 | 0 ± 0 | 0 ± 0 | 0 ± 0 | 1010 ± 324 | 0 ± 0 |
| Day 33 | — | 0 ± 0 | 0 ± 0 | 0 ± 0 | 0 ± 0 | 0 ± 0 | 0 ± 0 | 2015 ± 487 | 0 ± 0 |
| Day 40 | — | 0 ± 0 | 0 ± 0 | 0 ± 0 | 0 ± 0 | 0 ± 0 | 0 ± 0 | 2703 ± 590 | 0 ± 0 |
| Day 48 | — | 0 ± 0 | 0 ± 0 | 0 ± 0 | 0 ± 0 | 0 ± 0 | 0 ± 0 | — | 0 ± 0 |
| Day 54 | — | 0 ± 0 | 0 ± 0 | 0 ± 0 | 0 ± 0 | 0 ± 0 | 0 ± 0 | — | 0 ± 0 |
| Day 54 | — | 0 ± 0 | 0 ± 0 | 0 ± 0 | 0 ± 0 | 0 ± 0 | 0 ± 0 | — | 0 ± 0 |
| Day 60 | — | 0 ± 0 | 0 ± 0 | 0 ± 0 | 0 ± 0 | 0 ± 0 | 0 ± 0 | — | 0 ± 0 |

CD123-CPI inhibited tumor significantly compared to Neg.8.8-CPI (Table 9). At a dose of 0.3 mg/kg, all three CD123 ADCs: 18G3-CPI, 16D6-CPI and 3D1-CPI were cytotoxic. By day 17, ten out of ten animals in each group show tumor regression. All of these mice stayed tumor free at least until day 60 which is when the study ended. At a dose of 1 mg/kg of CD123 ADC, tumor regression occurred earlier, by day 12.

These data demonstrate that CD123-CPI inhibit growth of MOLM13 AML xenograft tumors.

To test the efficacy of CD123-ADC at lower doses, an in vivo efficacy study was performed using the same MOLM13 model. Animals were treated as described above. As shown below in Table 10, CD123-CPIs at 0.1 mg/kg, very effectively inhibit tumor growth in all mice, and in dose-dependent manner (Table 10, center columns "18G3-CPI" and "16D6-CPI"). In contrast, tumors in Neg. 8.8-CPI-treated mice continued to grow (Table 10, right column "Neg 8.8-CPI").

TABLE 10

MOLM-13 AML xenografts, mean tumor volume (mm³ +/− SEM) Q4dx4

| | PBS | CD123 -CPI | | | | | | Neg 8.8- CPI Control | | |
| | | 18G3-CPI | | | 16D6-CPI | | | | | |
| dose → (mg/kg) | 0 | 0.03 | 0.1 | 0.3 | 0.03 | 0.1 | 0.3 | 0.03 | 0.1 | 0.3 |
|---|---|---|---|---|---|---|---|---|---|---|
| Day 0 | 177 ± 10 | 187 ± 14 | 183 ± 15 | 181 ± 11 | 184 ± 13 | 181 ± 12 | 182 ± 9 | 181 ± 15 | 183 ± 14 | 188 ± 24 |
| Day 4 | 551 ± 47 | 199 ± 21 | 147 ± 21 | 112 ± 14 | 226 ± 22 | 178 ± 20 | 87 ± 9 | 494 ± 43 | 324 ± 56 | 209 ± 50 |
| Day 9 | 1614 ± 125 | 120 ± 19 | 40 ± 13 | 4 ± 4 | 169 ± 27 | 51 ± 13 | 0 ± 0 | 1530 ± 123 | 1060 ± 159 | 157 ± 38 |
| Day 11 | 2216 ± 149 | 110 ± 29 | 13 ± 10 | 0 ± 0 | 217 ± 52 | 10 ± 10 | 0 ± 0 | 2075 ± 79 | 1253 ± 170 | 78 ± 25 |
| Day 14 | — | 112 ± 45 | 0 ± 0 | 0 ± 0 | 371 ± 94 | 0 ± 0 | 0 ± 0 | — | 2217 ± 219 | 77 ± 31 |
| Day 16 | — | 106 ± 49 | 0 ± 0 | 0 ± 0 | 411 ± 104 | 0 ± 0 | 0 ± 0 | — | 1749 ± 280 | 38 ± 23 |
| Day 22 | — | 385 ± 143 | 0 ± 0 | 0 ± 0 | 1319 ± 275 | 0 ± 0 | 0 ± 0 | — | — | 147 ± 67 |
| Day 25 | — | 859 ± 308 | 0 ± 0 | 0 ± 0 | 1470 ± 344 | 0 ± 0 | 0 ± 0 | — | — | 356 ± 136 |
| Day 29 | — | 720 ± 273 | 0 ± 0 | 0 ± 0 | 1948 ± 653 | 0 ± 0 | 0 ± 0 | — | — | 865 ± 298 |
| Day 31 | — | 805 ± 349 | 0 ± 0 | 0 ± 0 | — | 0 ± 0 | 0 ± 0 | — | — | 577 ± 251 |
| Day 37 | — | 927 ± 653 | 0 ± 0 | 0 ± 0 | — | 0 ± 0 | 0 ± 0 | — | — | 1154 ± 352 |
| Day 42 | — | 747 ± 747 | 0 ± 0 | 0 ± 0 | — | 0 ± 0 | 0 ± 0 | — | — | 2363 ± 158 |
| Day 47 | — | — | 0 ± 0 | 0 ± 0 | — | 0 ± 0 | 0 ± 0 | — | — | — |
| Day 53 | — | — | 0 ± 0 | 0 ± 0 | — | 0 ± 0 | 0 ± 0 | — | — | — |
| Day 57 | — | — | 0 ± 0 | 0 ± 0 | — | 0 ± 0 | 0 ± 0 | — | — | — |
| Day 65 | — | — | 0 ± 0 | 0 ± 0 | — | 0 ± 0 | 0 ± 0 | — | — | — |

To test the efficacy of CD123-18G3-CTI, an in vivo efficacy study was performed using the same MOLM13 model. Animals were treated as described above. As shown in Table 11, treatment with CD123-18G3-CTI inhibited tumor growth in mice in dose-dependent manner. In contrast, tumors in Neg. 8.8-CTI treated mice continued to grow.

data are summarized in Table 12. CD123-18G3-H16-CPI compared to Neg 8.8-CPI and PBS vehicle.

The 0.6 mg/kg dose of CD123-CPI was the most potent ADC tested in this study, and by day 65, ten out of ten

TABLE 11

MOLM-13 AML xenografts, mean tumor volume (mm³ +/− SEM)
Q4dx4

|  | Neg.8.8-CTI | | CD123-18G3-CTI (Glucuronide) | | | CD123-18G3-CTI (Galactoside) | | | |
| --- | --- | --- | --- | --- | --- | --- | --- | --- | --- |
| DOSE (mg/kg) | 0.1 (Glu) | 0.3 (Gal) | 0.01 | 0.03 | 0.1 | 0.01 | 0.03 | 0.1 | 0.3 |
| Day −1 | 207 ± 12 | 213 ± 12 | 205 ± 11 | 211 ± 9 | 213 ± 11 | 208 ± 8 | 202 ± 7 | 209 ± 14 | 213 ± 15 |
| Day 5 | 698 ± 46 | 805 ± 67 | 702 ± 41 | 640 ± 48 | 358 ± 32 | 808 ± 88 | 688 ± 46 | 391 ± 30 | 320 ± 34 |
| Day 8 | 1264 ± 80 | 1304 ± 106 | 1215 ± 71 | 834 ± 77 | 307 ± 27 | 1500 ± 113 | 1191 ± 85 | 354 ± 33 | 248 ± 31 |
| Day 12 | 2551 ± 117 | 2062 ± 142 | 2338 ± 118 | 1196 ± 133 | 147 ± 17 | — | 2165 ± 160 | 278 ± 27 | 127 ± 17 |
| Day 15 | — | — | — | 1214 ± 128 | 61 ± 6 | — | — | 175 ± 21 | 59 ± 14 |
| Day 19 | — | — | — | 1583 ± 192 | 38 ± 12 | — | — | 142 ± 28 | 13 ± 8 |
| Day 22 | — | — | — | — | 0 ± 0 | — | — | 115 ± 36 | 18 ± 12 |
| Day 26 | — | — | — | — | 0 ± 0 | — | — | 194 ± 58 | 0 ± 0 |
| Day 29 | — | — | — | — | 0 ± 0 | — | — | 266 ± 93 | 0 ± 0 |
| Day 36 | — | — | — | — | 0 ± 0 | — | — | 635 ± 194 | 0 ± 0 |
| Day 39 | — | — | — | — | 0 ± 0 | — | — | 906 ± 254 | 0 ± 0 |
| Day 42 | — | — | — | — | 0 ± 0 | — | — | — | 0 ± 0 |
| Day 49 | — | — | — | — | 0 ± 0 | — | — | — | 0 ± 0 |
| Day 54 | — | — | — | — | 0 ± 0 | — | — | — | 0 ± 0 |
| Day 60 | — | — | — | — | 0 ± 0 | — | — | — | 0 ± 0 |

B. H.2 MV4-11 AML Xenografts

The effect of CD123 ADCs on growth of human tumors was assessed using immunodeficient mice. For subcutaneous (sc) AML models, 5×10⁶ MV4-11 cells were implanted subcutaneously in the flank of female NOD-SCID mice. When the tumors reached an average volume of 200 mm³, animals were staged to ensure uniformity of the tumor size among various treatment groups. The MV4-11 AML sc xenograft animals were dosed intravenously four times every four days (Q4dx4) with PBS vehicle, CD123-CPI, or 8.8-CPI at the following doses: 0.1, 0.3 and 0.6 mg/kg. The animals still on study remained tumor-free. Even at 0.3 mg/kg dose, nine out of ten mice show tumor regression around day 25 and stay tumor-free until the study ended at day 65. The data demonstrates that CD123-CPI inhibits growth of MV4-11 xenograft tumors.

TABLE 12

MV4-11 AML xenografts, mean tumor volume (mm3 +/− SEM)
q4dx4

|  | PBS | CD123-18G3-H16-CPI | | | Neg 8.8-H16-CPI | | |
| --- | --- | --- | --- | --- | --- | --- | --- |
| DOSE (mg/kg) | 0 | 0.1 | 0.3 | 0.6 | 0.1 | 0.3 | 0.6 |
| Day 0 | 235 ± 14 | 236 ± 17 | 232 ± 13 | 232 ± 15 | 236 ± 9 | 233 ± 11 | 228 ± 12 |
| Day 3 | 373 ± 19 | 225 ± 19 | 183 ± 11 | 174 ± 16 | 310 ± 20 | 289 ± 13 | 204 ± 16 |
| Day 8 | 579 ± 62 | 142 ± 15 | 114 ± 9 | 101 ± 7 | 509 ± 41 | 230 ± 39 | 118 ± 11 |
| Day 11 | 961 ± 112 | 161 ± 24 | 98 ± 9 | 79 ± 7 | 767 ± 72 | 289 ± 55 | 107 ± 16 |
| Day 15 | 1876 ± 200 | 189 ± 63 | 70 ± 18 | 57 ± 12 | 1428 ± 157 | 395 ± 77 | 60 ± 20 |
| Day 18 | 1781 ± 467 | 226 ± 84 | 60 ± 17 | 57 ± 12 | 1773 ± 136 | 615 ± 123 | 77 ± 23 |
| Day 21 | — | 392 ± 144 | 96 ± 23 | 67 ± 14 | 2560 ± 220 | 954 ± 186 | 112 ± 32 |
| Day 25 | — | 729 ± 271 | 111 ± 56 | 49 ± 20 | — | 1632 ± 230 | 168 ± 87 |
| Day 28 | — | 626 ± 337 | 125 ± 101 | 67 ± 30 | — | 1684 ± 688 | 301 ± 150 |
| Day 32 | — | 215 ± 197 | 208 ± 183 | 113 ± 79 | — | 1645 ± 677 | 431 ± 197 |
| Day 36 | — | 385 ± 367 | 40 ± 16 | 198 ± 177 | — | 1541 | 494 ± 129 |
| Day 39 | — | 0 ± 0 | 21 ± 11 | 265 ± 249 | — | 1901 | 603 ± 153 |
| Day 44 | — | 15 ± 15 | 29 ± 12 | 31 ± 15 | — | — | 1346 ± 348 |
| Day 51 | — | 0 ± 0 | 20 ± 10 | 32 ± 18 | — | — | 711 ± 411 |
| Day 58 | — | 40 ± 23 | 20 ± 10 | 27 ± 13 | — | — | 1450 ± 818 |
| Day 65 | — | 0 ± 0 | 9 ± 6 | 19 ± 10 | — | — |  |
| Day 73 | — | 0 ± 0 | 0 ± 0 | 0 ± 0 | — | — |  |

To test the efficacy of CD123-CTI, an in vivo efficacy study was performed using the same MV4-11 model. Animals were treated as described above. As shown in Table 13, CD123-CTI also inhibits tumor growth in mice in dose-dependent manner while the tumors in Neg. 8.8-CTI treated mice continue to grow.

TABLE 13

MV4-11 AML xenografts, mean tumor volume (mm$^3$ +/− SEM) Q4dx4

| | Neg.8.8-CTI | | CD123-18G3-CTI (Glucuronide) | | | CD123-18G3-CTI (Galactoside) | | |
|---|---|---|---|---|---|---|---|---|
| DOSE (mg/kg) | 0.3 (Glu) | 0.3 (Gal) | 0.03 | 0.1 | 0.3 | 0.03 | 0.1 | 0.3 |
| Day −1 | 229 ± 14 | 232 ± 10 | 235 ± 21 | 232 ± 11 | 235 ± 14 | 233 ± 11 | 232 ± 14 | 229 ± 13 |
| Day 4 | 307 ± 18 | 301 ± 18 | 299 ± 28 | 221 ± 15 | 189 ± 9 | 270 ± 23 | 260 ± 14 | 216 ± 18 |
| Day 7 | 361 ± 37 | 408 ± 49 | 468 ± 37 | 193 ± 10 | 122 ± 9 | 333 ± 19 | 214 ± 23 | 163 ± 12 |
| Day 12 | 458 ± 58 | 759 ± 74 | 804 ± 85 | 215 ± 30 | 96 ± 12 | 625 ± 52 | 325 ± 52 | 121 ± 25 |
| Day 15 | 513 ± 57 | 868 ± 78 | 1165 ± 128 | 214 ± 35 | 83 ± 14 | 873 ± 86 | 425 ± 68 | 114 ± 25 |
| Day 18 | 640 ± 85 | 1367 ± 179 | 1551 ± 107 | 229 ± 43 | 75 ± 11 | 1348 ± 104 | 519 ± 88 | 96 ± 19 |
| Day 21 | 867 ± 108 | 1970 ± 227 | 2263 ± 90 | 311 ± 60 | 94 ± 19 | 2140 ± 162 | 716 ± 124 | 86 ± 20 |
| Day 25 | 1264 ± 179 | — | — | 391 ± 85 | 50 ± 14 | — | 900 ± 170 | 70 ± 16 |
| Day 28 | 1497 ± 159 | — | — | 484 ± 99 | 73 ± 16 | — | 1192 ± 251 | 64 ± 16 |
| Day 32 | — | — | — | 627 ± 121 | 107 ± 19 | — | — | 82 ± 21 |
| Day 35 | — | — | — | 771 ± 144 | 89 ± 17 | — | — | 92 ± 21 |
| Day 40 | — | — | — | 1056 ± 205 | 65 ± 16 | — | — | 74 ± 24 |
| Day 43 | — | — | — | — | 46 ± 11 | — | — | 113 ± 44 |
| Day 47 | — | — | — | — | 58 ± 10 | — | — | 135 ± 72 |
| Day 50 | — | — | — | — | 67 ± 12 | — | — | 198 ± 107 |
| Day 54 | — | — | — | — | 49 ± 9 | — | — | 339 ± 210 |
| Day 61 | — | — | — | — | 61 ± 8 | — | — | 337 ± 273 |
| Day 70 | — | — | — | — | 41 ± 7 | — | — | — |
| Day 78 | — | — | — | — | 23 ± 7 | — | — | — |
| Day 84 | — | — | — | — | 35 ± 8 | — | — | — |
| Day 92 | — | — | — | — | 16 ± 6 | — | — | — |
| Day 99 | — | — | — | — | 11 ± 5 | — | — | — |

These results demonstrate that CD123 ADCs are highly efficacious in treating tumors.

Example 4: In Vivo Efficacy of CD123-ADCs

This Example illustrates the efficacy of CD123 ADCs in vivo using AML patient-derived disseminated xenografts (AML PDX).

The potency of CD123-CPI was examined in immunodeficient mice on the in vivo growth in a disseminated model established with patient bone marrow cells obtained in accordance with appropriate consent procedures. Table 14 provides a summary of the patient samples used in this study.

TABLE 14

| Model | Risk | Subtype | Abnormality | Cytogenetics |
|---|---|---|---|---|
| PDX2407 | Poor, Relapsed | M2 | FLT3-ITD | 46, XY |
| PDX0407 | Intermediate | M2 | NPM-1 FLT3-ITD | 46, XY |
| CTG 2226 | Poor, Refractory | M4 | FLT3-ITD Cytogenetics | 46, XY, add(6)(p21), del(8)(p21), add(12)(q24.1)[13]/46, XY, del(1)(q32), del(7)(q22q32), der(6; 12)(q10; p10), add(22)(q?11.2), +mar[3]/45, XY, t(1; 2)(p?22; q11.2), −21[1]/46, XY[3] |
| CTG 2229 | Poor, Refractory | M1 | Cytogenetics | 46, XY, del(2)(p13p?23), t(4; 13)(q31; q34), add(4)(q?25), del(6)(q13q25), t(9; 22)(q34; q11.2), del(10)(q24), add(16)(q24)[20] |
| CTG 2235 | Intermediate, De Novo | AML-MLD | Cytogenetics | 46, XY, del(20)(q11.2q13.1)[20] |
| CTG 2238 | Poor De Novo | Not selected | FLT3-ITD | Not available |
| CTG2240 | Intermediate, De Novo | AML-MLD | Cytogenetics | 46, XY, t(9; 11)(p22; q23), add(10)(q?24)[5]/46, XY[5] |
| 50170 | Poor, Relapsed | M1 | FLT3-ITD | 46, XY |

TABLE 14-continued

| Model | Risk | Subtype | Abnormality | Cytogenetics |
|---|---|---|---|---|
| 50102 | Favorable | Ambiguous | Not Detected | Not Detected |

For the studies, 1.0×10⁶ patient bone marrow cells were injected intravenously into the lateral tail vein of irradiated NSG mice. The study was staged and randomized based on engraftment of human CD45+/CD123+/CD33+ cells (12-55% in peripheral blood as measured by flow cytometric staining). The AML PDX mice were dosed intravenously 2 times every seven days (Q7dx2) with PBS vehicle or 18G3-CPI. About 3-5 days after the second/last dose, peripheral blood and bone marrow were harvested from sacrificed mice. Tumor cells remaining in bone marrow and blood of sacrificed animals were analyzed by flow cytometry. Results are summarized in the graph in FIG. 2 and Table 15. In Table 15, numbers represent the percentage of remaining tumor cells in the peripheral blood and bone marrow.

Figure 2:
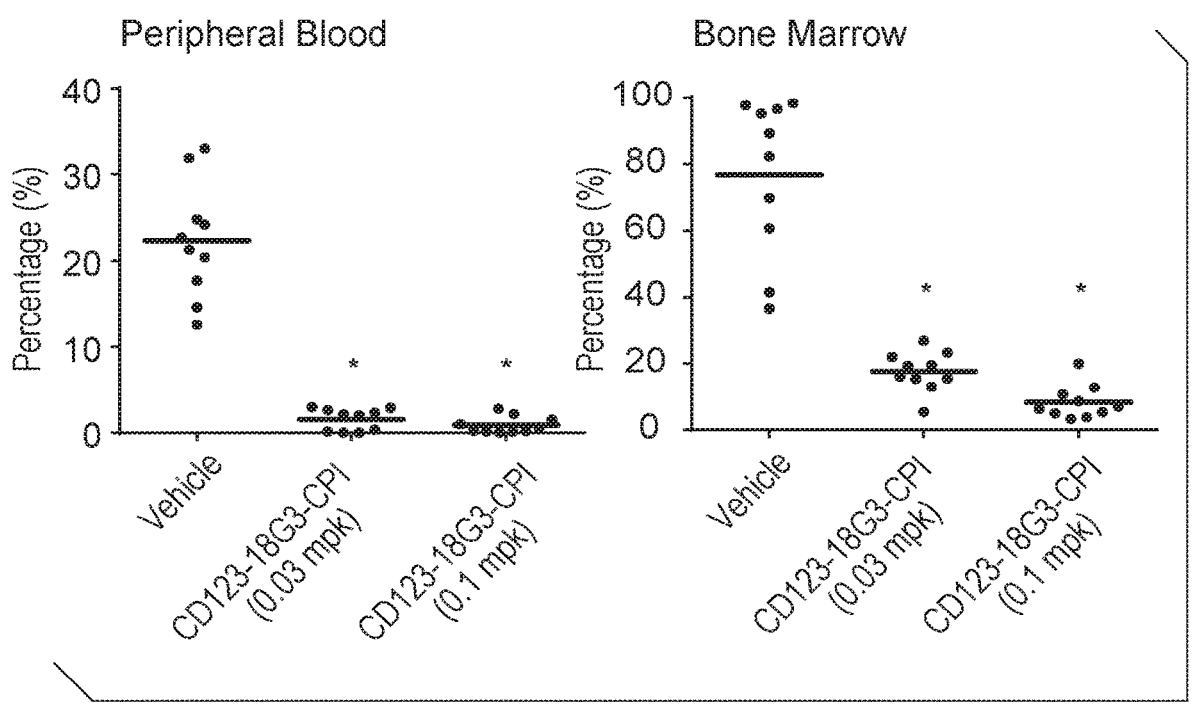
FIG. 2 depicts a representative flow cytometry analysis showing percentage of tumor cells remaining in peripheral blood (left graph) and bone marrow (right graph) in an animal model after treatment with either vehicle or CD123-ADC (CD123-18G3-CPI).

Each study has about 6 to 10 mice per group. The data demonstrate CD123 ADC is efficacious in reducing tumor cell numbers in both peripheral blood and bone marrow in a dose-dependent manner (FIG. 2 and Table 15).

TABLE 15

| Model | Dose CD123-CPI mg/kg | Peripheral Blood % Treated/ % Vehicle (% ± SEM) | Bone Marrow % Treated/ % Vehicle (% ± SEM) |
|---|---|---|---|
| PDX2407 | 0.1 | 0.56 ± 0.1/ 88 ± 1.1 | 3.04 ± 0.7/ 90 ± 2 |
|  | 0.5 | 0.3 ± 0.05/ 88 ± 1.1 | 0.14 ± 0.03/ 90 ± 2 |
| PDX0407 | 0.03 | 1.1 ± 0.2/ 29 ± 4.8 | 1.3 ± 0.4/ 30 ± 14 |
|  | 0.1 | 0.16 ± 0.04/ 29 ± 4.8 | 0.8 ± 0.3/ 30 ± 14 |
| CTG 2226 | 0.03 | 1.5 ± 0.4/ 21 ± 2 | 18 ± 1.9/ 77 ± 7.4 |
|  | 0.1 | 0.9 ± 0.3/ 22 ± 2 | 8 ± 1.6/ 77 ± 7.4 |
| CTG 2229 | 0.03 | 54 ± 9/ 65 ± 3.2 | 83 ± 6.9/ 84 ± 6 |
|  | 0.1 | 16 ± 2.5/ 65 ± 3.2 | 50 ± 9.7/ 84 ± 6 |
| CTG 2235 | 0.03 | 1.8 ± 0.6/ 31 ± 6 | 73 ± 6.1/ 83 ± 4.5 |
|  | 0.1 | 0.7 ± 0.23/ 31 ± 6 | 59 ± 6.3/ 83 ± 4.5 |
| CTG 2238 | 0.03 | 5.8 ± 0.7/ 32 ± 2 | 45 ± 9.7/ 95 ± 0.6 |
|  | 0.1 | 1.7 ± 0.5/ 32 ± 2 | 12 ± 1.6/ 95 ± 0.6 |
| CTG2240 | 0.03 | 1 ± 0.4/ 52 ± 2.9 | 60 ± 12/ 99 ± 0.1 |
|  | 0.1 | 0.2 ± 0.07/ 52 ± 2.9 | 16 ± 6.7/ 99 ± 0.1 |
| PDX 50170 | 0.03 | 0.4 ± 0.1/ 14 ± 1.4 | 24 ± 7.3/ 46 ± 9.6 |
| PDX 50120 | 0.03 | 53 ± 0.8/ 58 ± 0.8 | 83 ± 1.9/ 77 ± 2.6 |
|  | 0.1 | 40 ± 4.2/ 58 ± 0.8 | 83 ± 4.7/ 77 ± 2.6 |
|  | 0.3 | 31 ± 2.4/ 58 ± 0.8 | 78 ± 1.9/ 77 ± 2.6 |

Figure 3:
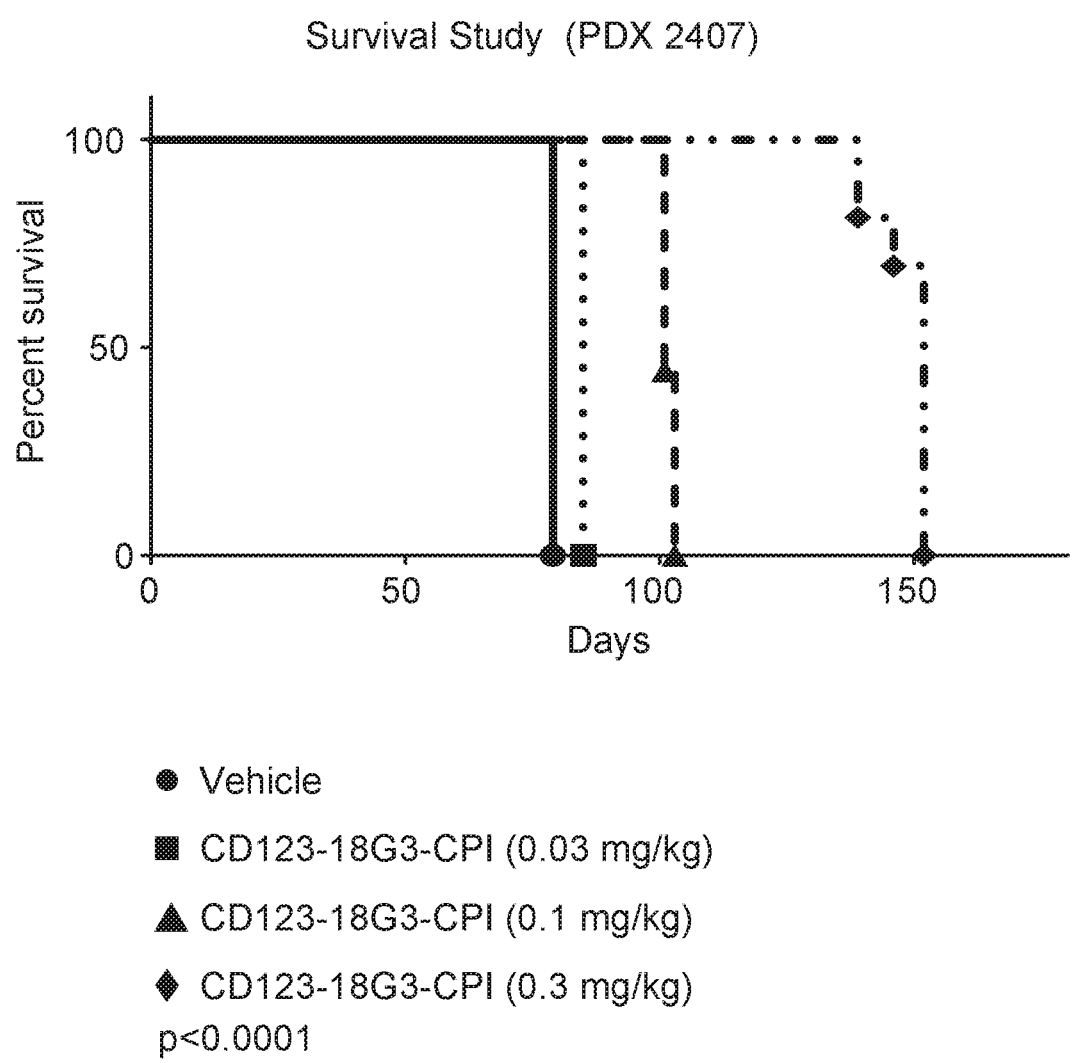
FIG. 3 depicts a graph summarizing survival length (in days) of animals treated with either vehicle or CD123 ADC at the indicated doses.

To determine whether CD123-18G3-CPI can increase overall survival of tumor bearing mice, a survival study was performed using PDX2407 when the peripheral blood shows a high engraftment, i.e., ~32% on average. The mice were dosed intravenously 2 times every seven days (Q7dx2) with PBS vehicle or CD123-CPI, and monitored daily. When a mouse showed clinical signs, such as lethargy and weight loss (following Association for Assessment of Laboratory Animal Care under Institutional Animal Care and Use Committee guidelines) the mouse was euthanized, Results are summarized in the graph in FIG. 3. Treatment with CD123-18G3-CPI extends overall survival of tumor bearing animals in a dose-dependent manner. Specifically, treatment with CD123-18G3-CPI at a dose of 0.1 mg/kg extended survival by about 25%, and treatment with CD123-18G3-CPI at a dose of 0.3 mg/kg approximately doubled the length of survival (FIG. 3).

These results demonstrate that treatment with a CD123-ADC induces regression and inhibits progression of AML, and extends survival.

Example 5: Preparation of CD123 Antibody Drug Conjugate (ADC)

This Example illustrates the conjugation and preparation of h18G3-AcLysValCitPABC-DMAE-CO_CPI-000638314, a CD123 ADC, also referred to herein as "18G3-CPI" or "CD123-18G3-CPI". 18G3-CPI is an ADC comprised of CD123 humanized mAb 18G3 (see Tables 2.0 and 2.1, supra, "h18G3"), AcLysValCitPABC linker and cyclopropylpyrroloindoline (CPI) agent. K222R, E295L, Q295L, Y296Q, N297G mutations were introduced in the upper hinge and Fc to enable site-specific conjugation of the CPI agent catalyzed by transglutaminase. The light chain and heavy chain amino acid sequences of CD123-18G3-H16-N60G-K222R humanized IgG1 antibody (referred to herein as "h18G3") are as follows:

```
Light chain:
                                       (SEQ ID NO: 30)
DIQMTQSPSSLSASVGDRVTITCKSSQSLLSSGTRKNYLAWYQQKPGKA

PKWYWASTRQSGVPSRFSGSGSGTDFTLTISSLQPEDFATYYCSQSYNL

YTFGQGTKLEIKRTVAAPSVFIFPPSDEQLKSGTASVVCLLNNFYPREA

KVQWKVDNALQSGNSQESVTEQDSKDSTYSLSSTLTLSKADYEKHKVYA

CEVTHQGLSSPVTKSFNRGEC

Heavy chain:
                                       (SEQ ID NO: 27)
EVQLVESGGGLVQPGGSLRLSCAASGFSLTSGDISWVRQAPGKGLEWVA

VIWSGGGTNYGSRLMSRFTISRDNAKNSLYLQMNSLRAEDTAVYYCARD

WGNFYFDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQ

TYICNVNHKPSNTKVDKKVEPKSCDRTHTCPPCPAPELLGGPSVFLFPP

KPKDTLMISRTPEVTCVVVDVSHEDPEVKFNWYVDGVEVHNAKTKPREL

LQGSTYRVVSVLTVLHQDWLNGKEYKCKVSNKALPAPIEKTISKAKGQP

REPQVYTLPPSREEMTKNQVSLTCLVKGFYPSDIAVEWESNGQPENNYK

TTPPVLDSDGSFFLYSKLTVDKSRWQQGNVFSCSVMHEALHNHYTQKSL

SLSPG
```

The H16 site-specific mutation sequence is in bold italics above and includes five H16 site-specific transglutaminase mutations K222R (in the hinge), E294L, Q295L, Y296Q, and N297G. The LLQG sequence is the recognition tag for transglutaminase and the linker-agent is conjugated at Q296. G in CDR-H2 (underlined) is a N60G mutation.

The linker-agent, AcLysValCitPABC-DMAE-CO_CPI, is conjugated site-specifically at amino acid Q296. The AcLysValCitPABC-DMAE-CO_CPI-000638314 linker-agent structure is shown below.

Example 6: Methods of Conjugating Antibody to AcLysValCitPABC-DMAE-CO_CPI-000638314 Using Transglutaminase This Example illustrates conjugation of antibody to the linker-agent AcLysValCitPABC-DMAE-CO_CPI-000638314, also referred to herein as AcLysPABC-CPI-8314.

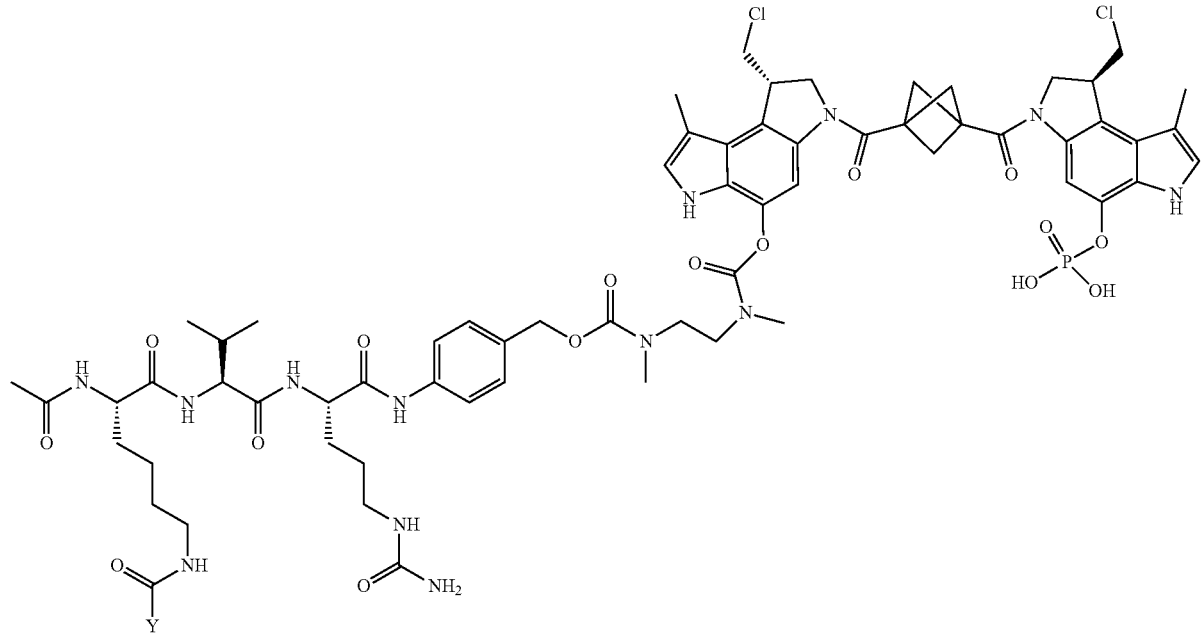

h18G3 was conjugated to AcLysValCitPABC-DMAE-CO_CPI-000638314 linker-agent via the use of bacterial transglutaminase (Sigma, 45 U/mg protein). In particular, the antibody was exchanged into buffer containing 100 mM KPO4, 200 mM NaCl, pH 7. The linker-agent was added in a 10-fold molar excess to the antibody in the presence of 7.5% (v/v) of dimethyl sulfoxide (DMSO). The enzymatic reaction was initiated by addition of 1 U of bacterial transglutaminase per mg of antibody and incubated at 25° C. overnight with continuous mixing.

The reaction mixture was incubated with 15% isopropyl alcohol for 30 min at room temperature. It was then diluted into 4 volume of 1M KPO4 buffer and purified via hydrophobic interaction chromatography (HIC) using Butyl-Sepharose HP column (GE Lifesciences). The method utilized 1M KPO4, 50 mM Tris, pH 7 for binding and the ADC was eluted with 50 mM Tris, pH 7 over 10 CV. The HIC purified compound was dialyzed into a final buffer of 20 mM Histidine, 85 mg/mL Sucrose, pH 5.8. The ADC was further characterized via SEC for purity and reverse phase chromatography to calculate drug-antibody ratio. The protein concentration was determined via UV spectrophotometer.

The lead antibody has very good expression of up to 700 mg/L as assessed in CHO pools, 88% yield recovery, and 99% purity following three steps of purification. 18G3 performed very well in conjugations as assessed by achieving DAR 1.9-2.0 and 55-60% conjugation yield post purification. The resulting ADC, CD123-18G3-H16-N60G-K222R-hG1-(Q)AcLysValCitPABC-DMAE-CO_CPI, exhibited good thermal stability and molecular integrity.

Conjugation of CPI linker-cytotoxic agent. Conjugation of AcLysPABC-CPI-8314 (structure shown above in Example 5) to the H16 site of an antibody was optimized by varying a variety of different parameters, such as molarity and salt composition, pH, enzyme concentration, time and temperature (Table 16). Briefly, the antibody was buffer exchanged into appropriate buffer and pH at each of the conditions shown in Table 16. A 10-fold molar excess of AcLysPABC-CPI-8314 linker-agent was added to the antibody and 5-10% dimethyl sulfoxide was added to solubilize the linker-agent in reaction mixture. After addition of bacterial transglutaminase (0.5-5 U/mg of antibody), the reaction mixture was continuously mixed for a stipulated time and temperature. The unreacted linker-agent and transglutaminase enzyme was removed either via size exclusion chromatography and/or hydrophobic interaction chromatography. Drug-antibody ratio was calculated via LCMS or RP-HPLC.

Conjugation efficiency as measured by antibody-drug ration (DAR) for the various conditions is shown in Table 16. For example, when the antibody was exchanged into buffer containing 30 mM KPO4, 150 mM NaCl at pH 7, a DAR of 1.6 was achieved.

Antibodies targeting CD33, CD123, Her2, PRLR, CD22, and other antigens, including antigens have been conjugated to the linker-agent AcLysValCitPABC-DMAE-CO_CPI-000638314 using these optimized conditions.

TABLE 16

| Buffer ionic strength | NaCl concentration, mM | pH | TG Units/mg Ab | Drug-Antibody Ration(DAR) |
|---|---|---|---|---|
| 20 mM NaAc | 75 | 5.8 | 1 | 0.3 |
| 30 mM KPO4 | 150 | 6.5 | 1 | 1.3 |
| 30 mM KPO4 | 150 | 7.0 | 0.5 | 1.6 |
| 30 mM KPO4 | 150 | 7.0 | 2 | 1.6 |
| 30 mM KPO4 | 150 | 7.0 | 5 | 1.4 |
| 30 mM KPO4 | 150 | 7.5 | 1 | 1.5 |
| 30 mM KPO4 | 150 | 8.0 | 1 | 0.6 |
| 25 mM Tris | 150 | 8.0 | 1 | 0.6 |

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

We claim:

1. An isolated antibody which specifically binds to CD123, wherein the antibody is selected from the group consisting of:
   (a) an antibody comprising: a heavy chain variable region (VH) comprising the amino acid sequence of SEQ ID NO: 6, and a light chain variable region (VL) comprising the amino acid sequence of SEQ ID NO: 17;
   (b) an antibody comprising: a heavy chain variable region (VH) comprising the amino acid sequence of SEQ ID NO: 24, and a light chain variable region (VL) comprising the amino acid sequence of SEQ ID NO: 28;
   (c) an antibody comprising: a heavy chain variable region (VH) comprising the amino acid sequence of SEQ ID NO: 32, and a light chain variable region (VL) comprising the amino acid sequence of SEQ ID NO: 39;
   (d) an antibody comprising: a heavy chain variable region (VH) comprising the amino acid sequence of SEQ ID NO: 44, and a light chain variable region (VL) comprising the amino acid sequence of SEQ ID NO: 48;
   (e) an antibody comprising: a heavy chain variable region (VH) comprising the amino acid sequence of SEQ ID NO: 51, and a light chain variable region (VL) comprising the amino acid sequence of SEQ ID NO: 57; and
   (f) an antibody comprising: a heavy chain variable region (VH) comprising the amino acid sequence of SEQ ID NO: 64, and a light chain variable region (VL) comprising the amino acid sequence of SEQ ID NO: 71.

2. An isolated antibody which specifically binds to CD123, wherein the antibody is selected from the group consisting of:
   (a) an antibody comprising:
      a heavy chain variable region (VH) comprising three complementarity determining regions (CDRs) CDR1, CDR2, and CDR3, wherein:
         (i) the VH CDR1 comprises the amino acid sequence of SEQ ID NO: 7;
         (ii) the VH CDR2 comprises the amino acid sequence of SEQ ID NO: 8; and
         (iii) the VH CDR3 comprises the amino acid sequence of SEQ ID NO: 9; and
      a light chain variable region (VL) comprising three complementarity determining regions CDR1, CDR2, and CDR3, wherein:
         (i) the VL CDR1 comprising the amino acid sequence of SEQ ID NO: 18;
         (ii) the VL CDR2 comprising the amino acid sequence of SEQ ID NO: 19; and
         (iii) the VL CDR3 comprising the amino acid sequence of SEQ ID NO: 20;

(b) an antibody comprising:
   a heavy chain variable region (VH) comprising three complementarity determining regions CDR1, CDR2, and CDR3, wherein:
      (i) the VH CDR1 comprises the amino acid sequence of SEQ ID NO: 7;
      (ii) the VH CDR2 comprises the amino acid sequence of SEQ ID NO: 25; and
      (iii) the VH CDR3 comprises the amino acid sequence of SEQ ID NO: 9; and
   a light chain variable region (VL) comprising three complementarity determining regions CDR1, CDR2, and CDR3, wherein:
      (i) the VL CDR1 comprising the amino acid sequence of SEQ ID NO: 18;
      (ii) the VL CDR2 comprising the amino acid sequence of SEQ ID NO: 19; and
      (iii) the VL CDR3 comprising the amino acid sequence of SEQ ID NO: 20;
(c) an antibody comprising:
   a heavy chain variable region (VH) comprising three complementarity determining regions CDR1, CDR2, and CDR3, wherein:
      (i) the VH CDR1 comprises the amino acid sequence of SEQ ID NO: 33;
      (ii) the VH CDR2 comprises the amino acid sequence of SEQ ID NO: 34; and
      (iii) the VH CDR3 comprises the amino acid sequence of SEQ ID NO: 35; and
   a light chain variable region (VL) comprising three complementarity determining regions CDR1, CDR2, and CDR3, wherein:
      (i) the VL CDR1 comprising the amino acid sequence of SEQ ID NO: 40;
      (ii) the VL CDR2 comprising the amino acid sequence of SEQ ID NO: 41; and
      (iii) the VL CDR3 comprising the amino acid sequence of SEQ ID NO: 42;
(d) an antibody comprising:
   a heavy chain variable region (VH) comprising three complementarity determining regions CDR1, CDR2, and CDR3, wherein:
      (i) the VH CDR1 comprises the amino acid sequence of SEQ ID NO: 33;
      (ii) the VH CDR2 comprises the amino acid sequence of SEQ ID NO: 45; and
      (iii) the VH CDR3 comprises the amino acid sequence of SEQ ID NO: 46; and
   a light chain variable region (VL) comprising three complementarity determining regions CDR1, CDR2, and CDR3, wherein:
      (i) the VL CDR1 comprising the amino acid sequence of SEQ ID NO: 40;
      (ii) the VL CDR2 comprising the amino acid sequence of SEQ ID NO: 41; and
      (iii) the VL CDR3 comprising the amino acid sequence of SEQ ID NO: 42;
(e) an antibody comprising:
   a heavy chain variable region (VH) comprising three complementarity determining regions CDR1, CDR2, and CDR3, wherein:
      (i) the VH CDR1 comprises the amino acid sequence of SEQ ID NO: 52;
      (ii) the VH CDR2 comprises the amino acid sequence of SEQ ID NO: 53; and
      (iii) the VH CDR3 comprises the amino acid sequence of SEQ ID NO: 54; and
   a light chain variable region (VL) comprising three complementarity determining regions CDR1, CDR2, and CDR3, wherein:
      (i) the VL CDR1 comprising the amino acid sequence of SEQ ID NO: 58;
      (ii) the VL CDR2 comprising the amino acid sequence of SEQ ID NO: 59; and
      (iii) the VL CDR3 comprising the amino acid sequence of SEQ ID NO: 60;
(f) an antibody comprising:
   a heavy chain variable region (VH) comprising three complementarity determining regions CDR1, CDR2, and CDR3, wherein:
      (i) the VH CDR1 comprises the amino acid sequence of SEQ ID NO: 65;
      (ii) the VH CDR2 comprises the amino acid sequence of SEQ ID NO: 66; and
      (iii) the VH CDR3 comprises the amino acid sequence of SEQ ID NO: 67; and
   a light chain variable region (VL) comprising three complementarity determining regions CDR1, CDR2, and CDR3, wherein:
      (i) the VL CDR1 comprising the amino acid sequence of SEQ ID NO: 72;
      (ii) the VL CDR2 comprising the amino acid sequence of SEQ ID NO: 73; and
      (iii) the VL CDR3 comprising the amino acid sequence of SEQ ID NO: 74.

3. An isolated antibody which specifically binds to CD123,
   wherein the VH of the antibody comprises:
      (i) a VH CDR1 comprising the amino acid sequence of SEQ ID NO: 7,
      (ii) a VH CDR2 comprising the amino acid sequence of SEQ ID NO: 25, and
      (iii) a VH CDR3 comprising the amino acid sequence of SEQ ID NO: 9; and
   wherein the VL of the antibody comprises:
      (i) a VL CDR1 comprising the amino acid sequence of SEQ ID NO: 18,
      (ii) a VL CDR2 comprising the amino acid sequence of SEQ ID NO: 19, and
      (iii) a VL CDR3 comprising the amino acid sequence of SEQ ID NO: 20.

4. An isolated antibody which specifically binds to CD123, wherein the antibody comprises a light chain comprising the amino acid sequence of SEQ ID NO: 30 and a heavy chain comprising the amino acid sequence of SEQ ID NO: 27.

5. An isolated antibody which specifically binds to CD123, wherein the antibody comprises a heavy chain variable region produced by the expression vector with ATCC Accession No. PTA-124283, and a light chain variable region produced by the expression vector with ATCC Accession No. PTA-124284.

6. The antibody of claim 1, wherein the antibody comprises an acyl donor glutamine-containing tag engineered at a specific site,
   wherein the acyl donor glutamine-containing tag is selected from the group consisting of Q, LQG, LLQGG (SEQ ID NO:77), LLQG (SEQ ID NO:78), LSLSQG (SEQ ID NO: 79), GGGLLQGG (SEQ ID NO: 80), GLLQG (SEQ ID NO: 81), LLQ, GSPLAQSHGG (SEQ ID NO: 82), GLLQGGG (SEQ ID NO: 83), GLLQGG (SEQ ID NO: 84), GLLQ (SEQ ID NO: 85), LLQLLQGA (SEQ ID NO: 86), LLQGA (SEQ ID NO: 87), LLQYQGA (SEQ ID NO: 88), LLQGSG (SEQ ID NO: 89), LLQYQG (SEQ ID NO: 90), LLQLLQG (SEQ ID NO: 91), SLLQG (SEQ ID NO: 92), LLQLQ (SEQ ID NO: 93), LLQLLQ (SEQ ID NO: 94), LLQGR (SEQ ID NO: 95), LLQGPP (SEQ ID NO: 96), LLQGPA (SEQ ID NO: 97), GGLLQGPP (SEQ ID NO: 98), GGLLQGA (SEQ ID NO: 99), LLQGPGK (SEQ ID NO: 100), LLQGPG (SEQ ID NO: 101), LLQGP (SEQ ID NO: 102), LLQP (SEQ ID NO: 103), LLQPGK (SEQ ID NO: 104), LLQAPGK (SEQ ID NO: 105), LLQGAPG (SEQ ID NO: 106), LLQGAP (SEQ ID NO: 107), and LLQLQG (SEQ ID NO: 108),
wherein the specific site is selected from the group consisting of:
the carboxyl terminus of the antibody light chain;
the amino terminus of the antibody light chain;
the carboxyl terminus of the antibody heavy chain;
the amino terminus of the antibody heavy chain; and
one or more amino acid residue(s) selected from S60-R61, R108, T135, S160, S168, S190-S192, P189-S192, G200-S202, K222-T225, K222-T223, T223, L251-S254, M252-I253, E294-N297, E293-N297, N297, and G385 as relating to SEQ ID NO: 27, and
wherein the acyl-donor glutamine-containing tag is inserted in the antibody specific site or replaces at least one endogenous amino acid in the antibody specific site.

7. The antibody of claim 6, wherein the antibody further comprises an amino acid modification at position 222, 340, or 370.

8. The antibody of claim 7, wherein the amino acid modification is a substitution from lysine to arginine.

9. The antibody of claim 1, wherein the antibody further comprises a linker, wherein the linker is selected from the group consisting of Ac-Lys-Gly (acetyl-lysine-glycine), aminocaproic acid, Ac-Lys-β-Ala (acetyl-lysine-β-alanine), amino-PEG2 (polyethylene glycol)-C2, amino-PEG3-C2, amino-PEG6-C2, Ac-Lys-Val-Cit-PABC (acetyl-lysine-valine-citrulline-p-aminobenzyloxycarbonyl), amino-PEG6-C2-Val-Cit-PABC, aminocaproyl-Val-Cit-PABC, [(3R,5R)-1-{3-[2-(2-aminoethoxy)ethoxy]propanoyl}piperidine-3,5-diyl]bis-Val-Cit-PABC, [(3 S,5 S)-1-{3-[2-(2-aminoethoxy)ethoxy]propanoyl}piperidine-3,5-diyl]bis-Val-Cit-PABC, putrescine, and Ac-Lys-putrescine.

10. An antibody-agent conjugate of the antibody of claim 9, comprising an agent selected from the group consisting of a cytotoxic agent, an immunomodulating agent, an imaging agent, a therapeutic protein, a biopolymer, and an oligonucleotide,
wherein the linker conjugates the antibody and the agent.

11. The antibody-agent conjugate of claim 10, wherein the cytotoxic agent is selected from the group consisting of an anthracycline, an auristatin, a camptothecin, a combretastatin, a CBI dimer, a cyclopropylpyrroloindoline (CPI) dimer, a CTI dimer, a dolastatin, a duocarmycin, an enediyne, a geldanamycin, an indolino-benzodiazepine dimer, a maytansine, a puromycin, a pyrrolobenzodiazepine dimer, a taxane, a vinca alkaloid, a tubulysin, a hemiasterlin, a spliceostatin, and a pladienolide.

12. The antibody-agent conjugate of claim 10, wherein the conjugate comprises the formula: antibody-(acyl donor glutamine-containing tag)-(linker)-(cytotoxic agent), wherein the acyl donor glutamine-containing tag comprises amino acid residues L294 through G297 (LLQG) in SEQ ID NO:27.

13. A pharmaceutical composition comprising a therapeutically effective amount of the antibody of claim 1 or the antibody-agent conjugate of claim 10 and a pharmaceutically acceptable carrier.

14. An isolated polynucleotide comprising a nucleotide sequence encoding the antibody of claim 1.

15. A vector comprising the polynucleotide of claim 14.

16. An isolated host cell that recombinantly produces the antibody of claim 1.

17. A method of treating a condition associated with cells expressing CD123 in a subject, the method comprising administering to a subject in need thereof an effective amount of the pharmaceutical composition of claim 13.

18. A method of inhibiting tumor growth or progression in a subject who has malignant cells expressing CD123, the method comprising administering to the subject in need thereof an effective amount of the pharmaceutical composition of claim 13 to the subject.

19. A method of inhibiting metastasis of malignant cells expressing CD123 in a subject, the method comprising administering to the subject in need thereof an effective amount of the pharmaceutical composition of claim 13 to the subject.

20. A method of inducing tumor regression in a subject who has malignant cells expressing CD123, the method comprising administering to the subject in need thereof an effective amount of the pharmaceutical composition of claim 13 to the subject.

21. A method for conjugating the antibody of claim 1 to AcLysValCitPABC-DMAE-CO_CPI-000638314 (AcLysPABC-CPI-8314), the method comprising:
preparing a composition comprising the antibody of claim 1 and AcLysPABC-CPI-8314 in a buffer comprising 30 to 100 mM KPO4 and 150 to 200 mM NaCl;
adding bacterial transglutaminase to the composition; and
incubating the composition to allow conjugation of the antibody to the AcLysPABC-CPI-8314.

22. An antibody-drug conjugate comprising:
an antibody which specifically binds to CD123 and comprises a heavy chain comprising SEQ ID NO: 27 and a light chain comprising SEQ ID NO: 30;
an acetyl-lysine-valine-citrulline-p-aminobenzyloxycarbonyl (Ac-Lys-Val-Cit-PABC) linker, and
an agent selected from the group consisting of a cytotoxic agent, an immunomodulating agent, an imaging agent, a therapeutic protein, a biopolymer, and an oligonucleotide,
wherein the linker conjugates the antibody and the agent.

23. An antibody-drug conjugate comprising:
an antibody which specifically binds to CD123 and comprises a heavy chain comprising SEQ ID NO: 27 and a light chain comprising SEQ ID NO: 30;
an acetyl-lysine-valine-citrulline-p-aminobenzyloxycarbonyl (Ac-Lys-Val-Cit-PABC) linker, and
a cyclopropylpyrroloindoline (CPI) dimer,
wherein the linker conjugates the antibody and the CPI dimer.

24. The antibody-agent conjugate of claim 10, wherein the cytotoxic agent is a stereoisomer, isostere, analog, or derivative of an anthracycline, an auristatin, a camptothecin, a combretastatin, a CBI dimer, a cyclopropylpyrroloindoline (CPI) dimer, a CTI dimer, a dolastatin, a duocarmycin, an enediyne, a geldanamycin, an indolino-benzodiazepine dimer, a maytansine, a puromycin, a pyrrolobenzodiazepine dimer, a taxane, a vinca alkaloid, a tubulysin, a hemiasterlin, a spliceostatin, or a pladienolide.

25. The antibody of claim 1, wherein the antibody comprises an acyl donor glutamine-containing tag engineered at a specific site,
   wherein the acyl donor glutamine-containing tag is selected from the group consisting of Q, LQG, LLQGG (SEQ ID NO:77), LLQG (SEQ ID NO:78), LSLSQG (SEQ ID NO: 79), GGGLLQGG (SEQ ID NO: 80), GLLQG (SEQ ID NO: 81), LLQ, GSPLAQSHGG (SEQ ID NO: 82), GLLQGGG (SEQ ID NO: 83), GLLQGG (SEQ ID NO: 84), GLLQ (SEQ ID NO: 85), LLQLLQGA (SEQ ID NO: 86), LLQGA (SEQ ID NO: 87), LLQYQGA (SEQ ID NO: 88), LLQGSG (SEQ ID NO: 89), LLQYQG (SEQ ID NO: 90), LLQLLQG (SEQ ID NO: 91), SLLQG (SEQ ID NO: 92), LLQLQ (SEQ ID NO: 93), LLQLLQ (SEQ ID NO: 94), LLQGR (SEQ ID NO: 95), LLQGPP (SEQ ID NO: 96), LLQGPA (SEQ ID NO: 97), GGLLQGPP (SEQ ID NO: 98), GGLLQGA (SEQ ID NO: 99), LLQGPGK (SEQ ID NO: 100), LLQGPG (SEQ ID NO: 101), LLQGP (SEQ ID NO: 102), LLQP (SEQ ID NO: 103), LLQPGK (SEQ ID NO: 104), LLQAPGK (SEQ ID NO: 105), LLQGAPG (SEQ ID NO: 106), LLQGAP (SEQ ID NO: 107), and LLQLQG (SEQ ID NO: 108),
   wherein the specific site is amino acid E294-N297 as relating to SEQ ID NO: 27, and
   wherein the acyl-donor glutamine-containing tag is inserted in the antibody specific site or replaces at least one endogenous amino acid in the antibody specific site.

26. The antibody of claim 1, wherein the antibody comprises an acyl donor glutamine-containing tag engineered at a specific site,
   wherein the acyl donor glutamine-containing tag is selected from the group consisting of Q, LQG, and LLQG (SEQ ID NO:78),
   wherein the specific site is amino acid E294-N297 as relating to SEQ ID NO: 27, and
   wherein the acyl-donor glutamine-containing tag is inserted in the antibody specific site or replaces at least one endogenous amino acid in the antibody specific site.

* * * * *

SEQUENCE LISTING

<160> NUMBER OF SEQ ID NOS: 108

<210> SEQ ID NO 1
<211> LENGTH: 380
<212> TYPE: PRT
<213> ORGANISM: Homo sapiens

<400> SEQUENCE: 1

```
Met Glu Thr Asp Thr Leu Leu Leu Trp Val Leu Leu Leu Trp Val Pro
1               5                   10                  15

Gly Ser Thr Gly Thr Lys Glu Asp Pro Asn Pro Ile Thr Asn Leu
                20                  25                  30

Arg Met Lys Ala Lys Ala Gln Gln Leu Thr Trp Asp Leu Asn Arg Asn
            35                  40                  45

Val Thr Asp Ile Glu Cys Val Lys Asp Ala Asp Tyr Ser Met Pro Ala
        50                  55                  60

Val Asn Asn Ser Tyr Cys Gln Phe Gly Ala Ile Ser Leu Cys Glu Val
65                  70                  75                  80

Thr Asn Tyr Thr Val Arg Val Ala Asn Pro Pro Phe Ser Thr Trp Ile
                85                  90                  95

Leu Phe Pro Glu Asn Ser Gly Lys Pro Trp Ala Gly Ala Glu Asn Leu
            100                 105                 110

Thr Cys Trp Ile His Asp Val Asp Phe Leu Ser Cys Ser Trp Ala Val
        115                 120                 125

Gly Pro Gly Ala Pro Ala Asp Val Gln Tyr Asp Leu Tyr Leu Asn Val
    130                 135                 140

Ala Asn Arg Arg Gln Gln Tyr Glu Cys Leu His Tyr Lys Thr Asp Ala
145                 150                 155                 160

Gln Gly Thr Arg Ile Gly Cys Arg Phe Asp Asp Ile Ser Arg Leu Ser
                165                 170                 175

Ser Gly Ser Gln Ser Ser His Ile Leu Val Arg Gly Arg Ser Ala Ala
            180                 185                 190

Phe Gly Ile Pro Cys Thr Asp Lys Phe Val Val Phe Ser Gln Ile Glu
        195                 200                 205

Ile Leu Thr Pro Pro Asn Met Thr Ala Lys Cys Asn Lys Thr His Ser
    210                 215                 220
```

```
Phe Met His Trp Lys Met Arg Ser His Phe Asn Arg Lys Phe Arg Tyr
225                 230                 235                 240

Glu Leu Gln Ile Gln Lys Arg Met Gln Pro Val Ile Thr Glu Gln Val
            245                 250                 255

Arg Asp Arg Thr Ser Phe Gln Leu Leu Asn Pro Gly Thr Tyr Thr Val
        260                 265                 270

Gln Ile Arg Ala Arg Glu Arg Val Tyr Glu Phe Leu Ser Ala Trp Ser
    275                 280                 285

Thr Pro Gln Arg Phe Glu Cys Asp Gln Glu Gly Ala Asn Thr Arg
290                 295                 300

Ala Trp Arg Thr Ser Leu Leu Ile Ala Leu Gly Thr Leu Leu Ala Leu
305                 310                 315                 320

Val Cys Val Phe Val Ile Cys Arg Arg Tyr Leu Val Met Gln Arg Leu
            325                 330                 335

Phe Pro Arg Ile Pro His Met Lys Asp Pro Ile Gly Asp Ser Phe Gln
        340                 345                 350

Asn Asp Lys Leu Val Val Trp Glu Ala Gly Lys Ala Gly Leu Glu Glu
    355                 360                 365

Cys Leu Val Thr Glu Val Gln Val Val Gln Lys Thr
370                 375                 380

<210> SEQ ID NO 2
<211> LENGTH: 336
<212> TYPE: PRT
<213> ORGANISM: Homo sapiens

<400> SEQUENCE: 2

Met Glu Thr Asp Thr Leu Leu Leu Trp Val Leu Leu Leu Trp Val Pro
1               5                   10                  15

Gly Ser Thr Gly Thr Lys Glu Asp Pro Asn Pro Ile Thr Asn Leu
            20                  25                  30

Arg Met Lys Ala Lys Ala Gln Gln Leu Thr Trp Asp Leu Asn Arg Asn
        35                  40                  45

Val Thr Asp Ile Glu Cys Val Lys Asp Ala Asp Tyr Ser Met Pro Ala
    50                  55                  60

Val Asn Asn Ser Tyr Cys Gln Phe Gly Ala Ile Ser Leu Cys Glu Val
65                  70                  75                  80

Thr Asn Tyr Thr Val Arg Val Ala Asn Pro Pro Phe Ser Thr Trp Ile
                85                  90                  95

Leu Phe Pro Glu Asn Ser Gly Lys Pro Trp Ala Gly Ala Glu Asn Leu
            100                 105                 110

Thr Cys Trp Ile His Asp Val Asp Phe Leu Ser Cys Ser Trp Ala Val
        115                 120                 125

Gly Pro Gly Ala Pro Ala Asp Val Gln Tyr Asp Leu Tyr Leu Asn Val
    130                 135                 140

Ala Asn Arg Arg Gln Gln Tyr Glu Cys Leu His Tyr Lys Thr Asp Ala
145                 150                 155                 160

Gln Gly Thr Arg Ile Gly Cys Arg Phe Asp Asp Ile Ser Arg Leu Ser
                165                 170                 175

Ser Gly Ser Gln Ser Ser His Ile Leu Val Arg Gly Arg Ser Ala Ala
            180                 185                 190

Phe Gly Ile Pro Cys Thr Asp Lys Phe Val Val Phe Ser Gln Ile Glu
        195                 200                 205

Ile Leu Thr Pro Pro Asn Met Thr Ala Lys Cys Asn Lys Thr His Ser
    210                 215                 220
```

```
Phe Met His Trp Lys Met Arg Ser His Phe Asn Arg Lys Phe Arg Tyr
225                 230                 235                 240

Glu Leu Gln Ile Gln Lys Arg Met Gln Pro Val Ile Thr Glu Gln Val
            245                 250                 255

Arg Asp Arg Thr Ser Phe Gln Leu Leu Asn Pro Gly Thr Tyr Thr Val
        260                 265                 270

Gln Ile Arg Ala Arg Glu Arg Val Tyr Glu Phe Leu Ser Ala Trp Ser
    275                 280                 285

Thr Pro Gln Arg Phe Glu Cys Asp Gln Glu Glu Gly Ala Asn Thr Arg
290                 295                 300

Ala Trp Arg Gly Gly Pro Pro Asp Tyr Lys Asp Asp Asp Lys Gly
305                 310                 315                 320

Gly Gly Leu Asn Asp Ile Phe Glu Ala Gln Lys Ile Glu Trp His Glu
            325                 330                 335

<210> SEQ ID NO 3
<211> LENGTH: 301
<212> TYPE: PRT
<213> ORGANISM: Homo sapiens

<400> SEQUENCE: 3

Met Glu Thr Asp Thr Leu Leu Leu Trp Val Leu Leu Leu Trp Val Pro
1               5                   10                  15

Gly Ser Thr Gly Thr Lys Glu Gly Lys Pro Trp Ala Gly Ala Glu Asn
            20                  25                  30

Leu Thr Cys Trp Ile His Asp Val Asp Phe Leu Ser Cys Ser Trp Ala
        35                  40                  45

Val Gly Pro Gly Ala Pro Ala Asp Val Gln Tyr Asp Leu Tyr Leu Asn
    50                  55                  60

Val Ala Asn Arg Arg Gln Gln Tyr Glu Cys Leu His Tyr Lys Thr Asp
65                  70                  75                  80

Ala Gln Gly Thr Arg Ile Gly Cys Arg Phe Asp Asp Ile Ser Arg Leu
                85                  90                  95

Ser Ser Gly Ser Gln Ser Ser His Ile Leu Val Arg Gly Arg Ser Ala
            100                 105                 110

Ala Phe Gly Ile Pro Cys Thr Asp Lys Phe Val Val Phe Ser Gln Ile
        115                 120                 125

Glu Ile Leu Thr Pro Pro Asn Met Thr Ala Lys Cys Asn Lys Thr His
    130                 135                 140

Ser Phe Met His Trp Lys Met Arg Ser His Phe Asn Arg Lys Phe Arg
145                 150                 155                 160

Tyr Glu Leu Gln Ile Gln Lys Arg Met Gln Pro Val Ile Thr Glu Gln
                165                 170                 175

Val Arg Asp Arg Thr Ser Phe Gln Leu Leu Asn Pro Gly Thr Tyr Thr
            180                 185                 190

Val Gln Ile Arg Ala Arg Glu Arg Val Tyr Glu Phe Leu Ser Ala Trp
        195                 200                 205

Ser Thr Pro Gln Arg Phe Glu Cys Asp Gln Glu Glu Gly Ala Asn Thr
    210                 215                 220

Arg Ala Trp Arg Thr Ser Leu Leu Ile Ala Leu Gly Thr Leu Leu Ala
225                 230                 235                 240

Leu Val Cys Val Phe Val Ile Cys Arg Arg Tyr Leu Val Met Gln Arg
                245                 250                 255

Leu Phe Pro Arg Ile Pro His Met Lys Asp Pro Ile Gly Asp Ser Phe
```

```
        260                 265                 270
Gln Asn Asp Lys Leu Val Val Trp Glu Ala Gly Lys Ala Gly Leu Glu
            275                 280                 285
Glu Cys Leu Val Thr Glu Val Gln Val Gln Lys Thr
        290                 295                 300

<210> SEQ ID NO 4
<211> LENGTH: 337
<212> TYPE: PRT
<213> ORGANISM: Macaca fascicularis

<400> SEQUENCE: 4

Met Glu Thr Asp Thr Leu Leu Leu Trp Val Leu Leu Leu Trp Val Pro
1               5                   10                  15
Gly Ser Thr Gly Gln Thr Lys Glu Asp Pro Asn Ala Pro Ile Arg Asn
            20                  25                  30
Leu Arg Met Lys Glu Lys Ala Gln Gln Leu Met Trp Asp Leu Asn Arg
        35                  40                  45
Asn Val Thr Asp Val Glu Cys Ile Lys Gly Thr Asp Tyr Ser Met Pro
    50                  55                  60
Ala Met Asn Asn Ser Tyr Cys Gln Phe Gly Ala Ile Ser Leu Cys Glu
65                  70                  75                  80
Val Thr Asn Tyr Thr Val Arg Val Ala Ser Pro Pro Phe Ser Thr Trp
                85                  90                  95
Ile Leu Phe Pro Glu Asn Ser Gly Thr Pro Arg Ala Gly Ala Glu Asn
            100                 105                 110
Leu Thr Cys Trp Val His Asp Val Asp Phe Leu Ser Cys Ser Trp Val
        115                 120                 125
Val Gly Pro Ala Ala Pro Ala Asp Val Gln Tyr Asp Leu Tyr Leu Asn
    130                 135                 140
Asn Pro Asn Ser His Glu Gln Tyr Arg Cys Leu His Tyr Lys Thr Asp
145                 150                 155                 160
Ala Arg Gly Thr Gln Ile Gly Cys Arg Phe Asp Asp Ile Ala Arg Leu
                165                 170                 175
Ser Arg Gly Ser Gln Ser Ser His Ile Leu Val Arg Gly Arg Ser Ala
            180                 185                 190
Ala Val Ser Ile Pro Cys Thr Asp Lys Phe Val Phe Ser Gln Ile
    195                 200                 205
Glu Arg Leu Thr Pro Pro Asn Met Thr Gly Glu Cys Asn Glu Thr His
210                 215                 220
Ser Phe Met His Trp Lys Met Lys Ser His Phe Asn Arg Lys Phe Arg
225                 230                 235                 240
Tyr Glu Leu Arg Ile Gln Lys Arg Met Gln Pro Val Arg Thr Glu Gln
                245                 250                 255
Val Arg Asp Thr Thr Ser Phe Gln Leu Pro Asn Pro Gly Thr Tyr Thr
            260                 265                 270
Val Gln Ile Arg Ala Arg Glu Thr Val Tyr Glu Phe Leu Ser Ala Trp
        275                 280                 285
Ser Thr Pro Gln Arg Phe Glu Cys Asp Gln Glu Glu Gly Ala Ser Ser
    290                 295                 300
Arg Ala Trp Arg Gly Pro Pro Asp Tyr Lys Asp Asp Asp Lys
305                 310                 315                 320
Gly Gly Gly Leu Asn Asp Ile Phe Glu Ala Gln Lys Ile Glu Trp His
                325                 330                 335
```

Glu

<210> SEQ ID NO 5
<211> LENGTH: 351
<212> TYPE: DNA
<213> ORGANISM: Mus musculus

<400> SEQUENCE: 5

```
caggtgaaac tgaaggagtc aggacctggc ctggtggcgc ccgcacagag tctgtccatt      60
acctgcactg tctctggatt ctcattaacc agtggtgaca taagttggat tcgccagcca     120
ccaggaaagg gtctggagtg gcttggagta atatggtctg gcggaggcac aaattataat     180
tctcgtctca tgtccagact gagcatcacc aaggacaact ccaggagtca agtgttctta     240
aaaatgaaca gtctgcaaac tgatgacacc gccatatatt attgtgtaag agattggggt     300 aactttttact ttgactattg gggccaaggc accactctca cagtctcctc a             351
```

<210> SEQ ID NO 6
<211> LENGTH: 117
<212> TYPE: PRT
<213> ORGANISM: Mus musculus

<400> SEQUENCE: 6

```
Gln Val Lys Leu Lys Glu Ser Gly Pro Gly Leu Val Ala Pro Ala Gln
1               5                   10                  15

Ser Leu Ser Ile Thr Cys Thr Val Ser Gly Phe Ser Leu Thr Ser Gly
            20                  25                  30

Asp Ile Ser Trp Ile Arg Gln Pro Pro Gly Lys Gly Leu Glu Trp Leu
        35                  40                  45

Gly Val Ile Trp Ser Gly Gly Gly Thr Asn Tyr Asn Ser Arg Leu Met
    50                  55                  60

Ser Arg Leu Ser Ile Thr Lys Asp Asn Ser Arg Ser Gln Val Phe Leu
65                  70                  75                  80

Lys Met Asn Ser Leu Gln Thr Asp Asp Thr Ala Ile Tyr Tyr Cys Val
                85                  90                  95

Arg Asp Trp Gly Asn Phe Tyr Phe Asp Tyr Trp Gly Gln Gly Thr Thr
            100                 105                 110

Leu Thr Val Ser Ser
        115
```

<210> SEQ ID NO 7
<211> LENGTH: 10
<212> TYPE: PRT
<213> ORGANISM: Mus musculus

<400> SEQUENCE: 7

```
Gly Phe Ser Leu Thr Ser Gly Asp Ile Ser
1               5                   10
```

<210> SEQ ID NO 8
<211> LENGTH: 16
<212> TYPE: PRT
<213> ORGANISM: Mus musculus

<400> SEQUENCE: 8

```
Val Ile Trp Ser Gly Gly Gly Thr Asn Tyr Asn Ser Arg Leu Met Ser
1               5                   10                  15
```

<210> SEQ ID NO 9
<211> LENGTH: 9

-continued

```
<212> TYPE: PRT
<213> ORGANISM: Mus musculus

<400> SEQUENCE: 9

Asp Trp Gly Asn Phe Tyr Phe Asp Tyr
1               5

<210> SEQ ID NO 10
<211> LENGTH: 11
<212> TYPE: PRT
<213> ORGANISM: Mus musculus

<400> SEQUENCE: 10

Trp Gly Gln Gly Thr Thr Leu Thr Val Ser Ser
1               5                   10

<210> SEQ ID NO 11
<211> LENGTH: 98
<212> TYPE: PRT
<213> ORGANISM: Homo sapiens

<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 12
<211> LENGTH: 15
<212> TYPE: PRT
<213> ORGANISM: Homo sapiens

<400> SEQUENCE: 12

Glu Pro Lys Ser Cys Asp Arg Thr His Thr Cys Pro Pro Cys Pro
1               5                   10                  15

<210> SEQ ID NO 13
<211> LENGTH: 110
<212> TYPE: PRT
<213> ORGANISM: Homo sapiens

<400> SEQUENCE: 13

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Leu
        50                  55                  60

Leu Gln Gly Ser Thr Tyr Arg Val Val Ser Val Leu Thr Val Leu His
```

```
                65                  70                  75                  80
Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 14
<211> LENGTH: 106
<212> TYPE: PRT
<213> ORGANISM: Homo sapiens

<400> SEQUENCE: 14

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 15
<211> LENGTH: 446
<212> TYPE: PRT
<213> ORGANISM: Artificial Sequence
<220> FEATURE:
<223> OTHER INFORMATION: SYNTHETIC CONSTRUCT

<400> SEQUENCE: 15

Gln Val Lys Leu Lys Glu Ser Gly Pro Gly Leu Val Ala Pro Ala Gln
1               5                   10                  15

Ser Leu Ser Ile Thr Cys Thr Val Ser Gly Phe Ser Leu Thr Ser Gly
            20                  25                  30

Asp Ile Ser Trp Ile Arg Gln Pro Pro Gly Lys Gly Leu Glu Trp Leu
        35                  40                  45

Gly Val Ile Trp Ser Gly Gly Thr Asn Tyr Asn Ser Arg Leu Met
    50                  55                  60

Ser Arg Leu Ser Ile Thr Lys Asp Asn Ser Arg Ser Gln Val Phe Leu
65                  70                  75                  80

Lys Met Asn Ser Leu Gln Thr Asp Thr Ala Ile Tyr Tyr Cys Val
                85                  90                  95

Arg Asp Trp Gly Asn Phe Tyr Phe Asp Tyr Trp Gly Gln Gly Thr Thr
            100                 105                 110

Leu Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175
```

```
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
        195                 200                 205
Thr Lys Val Asp Lys Lys Val Glu Pro Lys Ser Cys Asp Arg Thr His
225                 230                 235                 240
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Leu Leu Gln Gly Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly
        435                 440                 445

<210> SEQ ID NO 16
<211> LENGTH: 336
<212> TYPE: DNA
<213> ORGANISM: Mus musculus

<400> SEQUENCE: 16
gacattgtga tgtcacagtc tccatcctcc ctggctgtgt cagtaggaga gaaggtcact      60
atgagctgca aatccagtca gagtctgctc agcagtggaa cccgaaagaa ctacttggct     120
tggtaccagc agaaaccagg gcagtctcct aaactgctga tctactgggc atccactagg     180
caatctgggg tccctgatcg cttcacaggc ggtggatctg ggacagattt cactctcacc     240
atcagcagtg tgcaggctga ggacctggca gtttattact gcagtcaatc ttataatcta     300
tacacattcg gagggggggac caagctggaa ataaaa                              336

<210> SEQ ID NO 17
<211> LENGTH: 112
<212> TYPE: PRT
<213> ORGANISM: Mus musculus

<400> SEQUENCE: 17
```

```
Asp Ile Val Met Ser Gln Ser Pro Ser Ser Leu Ala Val Ser Val Gly
1               5                   10                  15

Glu Lys Val Thr Met Ser Cys Lys Ser Gln Ser Leu Leu Ser Ser
                20                  25                  30

Gly Thr Arg Lys Asn Tyr Leu Ala Trp Tyr Gln Gln Lys Pro Gly Gln
            35                  40                  45

Ser Pro Lys Leu Leu Ile Tyr Trp Ala Ser Thr Arg Gln Ser Gly Val
    50                  55                  60

Pro Asp Arg Phe Thr Gly Gly Ser Gly Thr Asp Phe Thr Leu Thr
65                  70                  75                  80

Ile Ser Ser Val Gln Ala Glu Asp Leu Ala Val Tyr Tyr Cys Ser Gln
                85                  90                  95

Ser Tyr Asn Leu Tyr Thr Phe Gly Gly Gly Thr Lys Leu Glu Ile Lys
            100                 105                 110
```

<210> SEQ ID NO 18
<211> LENGTH: 17
<212> TYPE: PRT
<213> ORGANISM: Mus musculus

<400> SEQUENCE: 18

```
Lys Ser Ser Gln Ser Leu Leu Ser Ser Gly Thr Arg Lys Asn Tyr Leu
1               5                   10                  15

Ala
```

<210> SEQ ID NO 19
<211> LENGTH: 7
<212> TYPE: PRT
<213> ORGANISM: Mus musculus

<400> SEQUENCE: 19

```
Trp Ala Ser Thr Arg Gln Ser
1               5
```

<210> SEQ ID NO 20
<211> LENGTH: 8
<212> TYPE: PRT
<213> ORGANISM: Mus musculus

<400> SEQUENCE: 20

```
Ser Gln Ser Tyr Asn Leu Tyr Thr
1               5
```

<210> SEQ ID NO 21
<211> LENGTH: 10
<212> TYPE: PRT
<213> ORGANISM: Homo sapiens

<400> SEQUENCE: 21

```
Phe Gly Gly Gly Thr Lys Leu Glu Ile Lys
1               5                   10
```

<210> SEQ ID NO 22
<211> LENGTH: 107
<212> TYPE: PRT
<213> ORGANISM: Homo sapiens

<400> SEQUENCE: 22

```
Arg Thr Val Ala Ala Pro Ser Val Phe Ile Phe Pro Pro Ser Asp Glu
1               5                   10                  15
```

```
Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 23
<211> LENGTH: 219
<212> TYPE: PRT
<213> ORGANISM: Artificial Sequence
<220> FEATURE:
<223> OTHER INFORMATION: SYNTHETIC CONSTRUCT

<400> SEQUENCE: 23

```
Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Ser Ser
                20                  25                  30

Gly Thr Arg Lys Asn Tyr Leu Ala Trp Tyr Gln Gln Lys Pro Gly Gln
            35                  40                  45

Ser Pro Lys Leu Leu Ile Tyr Trp Ala Ser Thr Arg Gln Ser Gly Val
        50                  55                  60

Pro Asp Arg Phe Thr Gly Gly Ser Gly Thr Asp Phe Thr Leu Thr
65                  70                  75                  80

Ile Ser Ser Val Gln Ala Glu Asp Leu Ala Val Tyr Tyr Cys Ser Gln
                85                  90                  95

Ser Tyr Asn Leu Tyr Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 24
<211> LENGTH: 117
<212> TYPE: PRT
<213> ORGANISM: Homo sapiens

<400> SEQUENCE: 24

Glu Val Gln Leu Val Glu Ser Gly Gly Gly Leu Val Gln Pro Gly Gly

```
            1               5                  10                  15
Ser Leu Arg Leu Ser Cys Ala Ala Ser Gly Phe Ser Leu Thr Ser Gly
                    20                  25                  30

Asp Ile Ser Trp Val Arg Gln Ala Pro Gly Lys Gly Leu Glu Trp Val
                35                  40                  45

Ala Val Ile Trp Ser Gly Gly Thr Asn Tyr Gly Ser Arg Leu Met
        50                  55                  60

Ser Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                    85                  90                  95

Arg Asp Trp Gly Asn Phe Tyr Phe Asp Tyr Trp Gly Gln Gly Thr Leu
                100                 105                 110

Val Thr Val Ser Ser
            115
```

<210> SEQ ID NO 25
<211> LENGTH: 16
<212> TYPE: PRT
<213> ORGANISM: Homo sapiens

<400> SEQUENCE: 25

```
Val Ile Trp Ser Gly Gly Thr Asn Tyr Gly Ser Arg Leu Met Ser
1               5                   10                  15
```

<210> SEQ ID NO 26
<211> LENGTH: 11
<212> TYPE: PRT
<213> ORGANISM: Homo sapiens

<400> SEQUENCE: 26

```
Trp Gly Gln Gly Thr Leu Val Thr Val Ser Ser
1               5                   10
```

<210> SEQ ID NO 27
<211> LENGTH: 446
<212> TYPE: PRT
<213> ORGANISM: Homo sapiens

<400> SEQUENCE: 27

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ser Gly
                    20                  25                  30

Asp Ile Ser Trp Val Arg Gln Ala Pro Gly Lys Gly Leu Glu Trp Val
                35                  40                  45

Ala Val Ile Trp Ser Gly Gly Thr Asn Tyr Gly Ser Arg Leu Met
        50                  55                  60

Ser Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                    85                  90                  95

Arg Asp Trp Gly Asn Phe Tyr Phe Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140
```

```
Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser
        180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Arg Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Leu Leu Gln Gly Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 28
<211> LENGTH: 112
<212> TYPE: PRT
<213> ORGANISM: Homo sapiens

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ser Ser
            20                  25                  30

Gly Thr Arg Lys Asn Tyr Leu Ala Trp Tyr Gln Gln Lys Pro Gly Lys
        35                  40                  45

Ala Pro Lys Leu Leu Ile Tyr Trp Ala Ser Thr Arg Gln Ser Gly Val
    50                  55                  60

Pro Ser Arg Phe Ser Gly Ser Gly Ser Gly Thr Asp Phe Thr Leu Thr
```

```
                65                  70                  75                  80
Ile Ser Ser Leu Gln Pro Glu Asp Phe Ala Thr Tyr Tyr Cys Ser Gln
                    85                  90                  95

Ser Tyr Asn Leu Tyr Thr Phe Gly Gln Gly Thr Lys Leu Glu Ile Lys
                    100                 105                 110

<210> SEQ ID NO 29
<211> LENGTH: 10
<212> TYPE: PRT
<213> ORGANISM: Homo sapiens

<400> SEQUENCE: 29

Phe Gly Gln Gly Thr Lys Leu Glu Ile Lys
1               5                   10

<210> SEQ ID NO 30
<211> LENGTH: 219
<212> TYPE: PRT
<213> ORGANISM: Homo sapiens

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ser Ser
            20                  25                  30

Gly Thr Arg Lys Asn Tyr Leu Ala Trp Tyr Gln Gln Lys Pro Gly Lys
        35                  40                  45

Ala Pro Lys Leu Leu Ile Tyr Trp Ala Ser Thr Arg Gln Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Ser Gln
                85                  90                  95

Ser Tyr Asn Leu Tyr Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 31
<211> LENGTH: 355
<212> TYPE: DNA
<213> ORGANISM: Mus musculus

<400> SEQUENCE: 31
caggtgcagc tgaaggagtc aggacctggc ctggtggcgc cctcacagag cctgtccata    60
```

-continued

```
acctgcactg tctctgggtt ctcattaacc aactttgata taagttggat tcgccagcca    120
ccaggaaagg gtctggagtg gcttggagta atgtggactg gtggaggcac aaattataat    180
tcagctttca tgtccagact gagcatcagc agggacatct ccaaaagcca gtttccttta    240
aaaatgagca gtctgcaaac tgatgacaca gccatatatt actgtgtaag agggatact    300 tacttctttg ctatggacta ctggggtcaa ggaacctccg tcaccgtctc atcag         355
```

<210> SEQ ID NO 32
<211> LENGTH: 118
<212> TYPE: PRT
<213> ORGANISM: Mus musculus

<400> SEQUENCE: 32

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asn Phe
            20                  25                  30

Asp Ile Ser Trp Ile Arg Gln Pro Pro Gly Lys Gly Leu Glu Trp Leu
        35                  40                  45

Gly Val Met Trp Thr Gly Gly Gly Thr Asn Tyr Asn Ser Ala Phe Met
    50                  55                  60

Ser Arg Leu Ser Ile Ser Arg Asp Ile Ser Lys Ser Gln Val Ser Leu
65                  70                  75                  80

Lys Met Ser Ser Leu Gln Thr Asp Asp Thr Ala Ile Tyr Tyr Cys Val
                85                  90                  95

Arg Gly Asp Thr Tyr Phe Phe Ala Met Asp Tyr Trp Gly Gln Gly Thr
            100                 105                 110

Ser Val Thr Val Ser Ser
        115

<210> SEQ ID NO 33
<211> LENGTH: 10
<212> TYPE: PRT
<213> ORGANISM: Mus musculus

<400> SEQUENCE: 33

Gly Phe Ser Leu Thr Asn Phe Asp Ile Ser
1               5                   10

<210> SEQ ID NO 34
<211> LENGTH: 16
<212> TYPE: PRT
<213> ORGANISM: Mus musculus

<400> SEQUENCE: 34

Val Met Trp Thr Gly Gly Gly Thr Asn Tyr Asn Ser Ala Phe Met Ser
1               5                   10                  15

<210> SEQ ID NO 35
<211> LENGTH: 10
<212> TYPE: PRT
<213> ORGANISM: Mus musculus

<400> SEQUENCE: 35

Gly Asp Thr Tyr Phe Phe Ala Met Asp Tyr
1               5                   10

<210> SEQ ID NO 36
<211> LENGTH: 11
<212> TYPE: PRT

<213> ORGANISM: Mus musculus

<400> SEQUENCE: 36

Trp Gly Gln Gly Thr Ser Val Thr Val Ser Ser
1               5                   10

<210> SEQ ID NO 37
<211> LENGTH: 447
<212> TYPE: PRT
<213> ORGANISM: Artificial Sequence
<220> FEATURE:
<223> OTHER INFORMATION: SYNTHETIC CONSTRUCT

<400> SEQUENCE: 37

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asn Phe
            20                  25                  30

Asp Ile Ser Trp Ile Arg Gln Pro Pro Gly Lys Gly Leu Glu Trp Leu
        35                  40                  45

Gly Val Met Trp Thr Gly Gly Thr Asn Tyr Asn Ser Ala Phe Met
    50                  55                  60

Ser Arg Leu Ser Ile Ser Arg Asp Ile Ser Lys Ser Gln Val Ser Leu
65                  70                  75                  80

Lys Met Ser Ser Leu Gln Thr Asp Asp Thr Ala Ile Tyr Tyr Cys Val
                85                  90                  95

Arg Gly Asp Thr Tyr Phe Phe Ala Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Arg Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Leu Leu Gln Gly Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly
                435                 440                 445

<210> SEQ ID NO 38
<211> LENGTH: 336
<212> TYPE: DNA
<213> ORGANISM: Mus musculus

<400> SEQUENCE: 38
gacatccaga tgacccagtc tccatcctcc ctgtctgcat ctgtaggaga cagagtcacc     60
atcacttgca atccagtca gagtctgctc agcagtggaa cccgaaagaa cttcttgtct    120
tggtatcagc agaaaccagg gaaagcccct aagctcctga tctattgggc atccactagg    180
ggatctgggg tcccatcaag gttcagtggc agtggatctg ggacagattt cactctcacc    240
atcagcagtc tgcaacctga agattttgca acttactact gtaaacaatc ttataatcta    300
tacacgtttg gccaggggac caagctggag atcaaa                              336

<210> SEQ ID NO 39
<211> LENGTH: 112
<212> TYPE: PRT
<213> ORGANISM: Mus musculus

<400> SEQUENCE: 39

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Ser Ser
                20                  25                  30

Gly Thr Arg Lys Asn Phe Leu Ser Trp Tyr Gln Gln Lys Thr Gly Gln
            35                  40                  45

Ser Pro Lys Leu Leu Ile Tyr Trp Ala Ser Thr Arg Gly Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Thr Glu Asp Leu Ala Val Tyr Tyr Cys Lys Gln
                85                  90                  95

Ser Tyr Asn Leu Tyr Thr Phe Gly Gly Gly Thr Lys Leu Glu Ile Lys
                100                 105                 110

<210> SEQ ID NO 40
<211> LENGTH: 17
<212> TYPE: PRT
<213> ORGANISM: Mus musculus

<400> SEQUENCE: 40

```
Lys Ser Ser Gln Ser Leu Leu Ser Ser Gly Thr Arg Lys Asn Phe Leu
1               5                   10                  15
Ser
```

<210> SEQ ID NO 41
<211> LENGTH: 7
<212> TYPE: PRT
<213> ORGANISM: Mus musculus

<400> SEQUENCE: 41

```
Trp Ala Ser Thr Arg Gly Ser
1               5
```

<210> SEQ ID NO 42
<211> LENGTH: 8
<212> TYPE: PRT
<213> ORGANISM: Mus musculus

<400> SEQUENCE: 42

```
Lys Gln Ser Tyr Asn Leu Tyr Thr
1               5
```

<210> SEQ ID NO 43
<211> LENGTH: 219
<212> TYPE: PRT
<213> ORGANISM: Mus musculus

<400> SEQUENCE: 43

```
Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Ser Ser
            20                  25                  30

Gly Thr Arg Lys Asn Phe Leu Ser Trp Tyr Gln Gln Lys Thr Gly Gln
        35                  40                  45

Ser Pro Lys Leu Leu Ile Tyr Trp Ala Ser Thr Arg Gly Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Thr Glu Asp Leu Ala Val Tyr Tyr Cys Lys Gln
                85                  90                  95

Ser Tyr Asn Leu Tyr Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 44

<211> LENGTH: 118
<212> TYPE: PRT
<213> ORGANISM: Homo sapiens

<400> SEQUENCE: 44

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Asn Phe
            20                  25                  30

Asp Ile Ser Trp Val Arg Gln Ala Pro Gly Lys Gly Leu Glu Trp Val
        35                  40                  45

Ala Val Met Trp Thr Gly Gly Thr Asn Tyr Gln Ser Ala Phe Met
    50                  55                  60

Ser Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Gly Asp Val Tyr Phe Phe Ala Met Asp Tyr Trp Gly Gln Gly Thr
            100                 105                 110

Leu Val Thr Val Ser Ser
            115
```

<210> SEQ ID NO 45
<211> LENGTH: 16
<212> TYPE: PRT
<213> ORGANISM: Homo sapiens

<400> SEQUENCE: 45

```
Val Met Trp Thr Gly Gly Thr Asn Tyr Gln Ser Ala Phe Met Ser
1               5                   10                  15
```

<210> SEQ ID NO 46
<211> LENGTH: 10
<212> TYPE: PRT
<213> ORGANISM: Homo sapiens

<400> SEQUENCE: 46

```
Gly Asp Val Tyr Phe Phe Ala Met Asp Tyr
1               5                   10
```

<210> SEQ ID NO 47
<211> LENGTH: 447
<212> TYPE: PRT
<213> ORGANISM: Homo sapiens

<400> SEQUENCE: 47

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Asn Phe
            20                  25                  30

Asp Ile Ser Trp Val Arg Gln Ala Pro Gly Lys Gly Leu Glu Trp Val
        35                  40                  45

Ala Val Met Trp Thr Gly Gly Thr Asn Tyr Gln Ser Ala Phe Met
    50                  55                  60

Ser Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Gly Asp Val Tyr Phe Phe Ala Met Asp Tyr Trp Gly Gln Gly Thr
```

```
                100             105             110
Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Arg Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Leu Leu Gln Gly Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 48
<211> LENGTH: 112
<212> TYPE: PRT
<213> ORGANISM: Homo sapiens

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ser Ser
            20                  25                  30
```

```
Gly Thr Arg Lys Asn Phe Leu Ser Trp Tyr Gln Gln Lys Pro Gly Lys
            35                  40                  45

Ala Pro Lys Leu Leu Ile Tyr Trp Ala Ser Thr Arg Gly Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Lys Gln
                85                  90                  95

Ser Tyr Asn Leu Tyr Thr Phe Gly Gln Gly Thr Lys Leu Glu Ile Lys
            100                 105                 110

<210> SEQ ID NO 49
<211> LENGTH: 219
<212> TYPE: PRT
<213> ORGANISM: Homo sapiens

<400> SEQUENCE: 49

Asp Ile Gln Met Thr Gln Ser Pro Ser Ser Leu Ser Ala Ser Val Gly
  1               5                  10                  15

Asp Arg Val Thr Ile Thr Cys Lys Ser Ser Gln Ser Leu Leu Ser Ser
             20                  25                  30

Gly Thr Arg Lys Asn Phe Leu Ser Trp Tyr Gln Gln Lys Pro Gly Lys
            35                  40                  45

Ala Pro Lys Leu Leu Ile Tyr Trp Ala Ser Thr Arg Gly Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Lys Gln
                85                  90                  95

Ser Tyr Asn Leu Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 50
<211> LENGTH: 354
<212> TYPE: DNA
<213> ORGANISM: Mus musculus

<400> SEQUENCE: 50
gaggtccagc tacaacagtc tggacctgaa ctggtgaagc ctggggcttc agtgaagatg    60
tcctgtaagg cttctggata caccttcagt gactacttca tgaagtgggt gaaacagagc   120
catggaaaga gacttgagtg gattggagat attaatccta caatggtga  aactttctac   180
```

```
aaccatcatt tcaagggcaa ggccacattg acaatagaca aatcctccag tacagcctac    240
atgcagctca acagcctgac atctgacgac tctgcagtct attactgtgc aagaccccgg    300
cgggggaatg ctatggactt ctggggtcaa ggaacctcag tcaccgtctc ctca          354
```

```
<210> SEQ ID NO 51
<211> LENGTH: 118
<212> TYPE: PRT
<213> ORGANISM: Mus musculus

<400> SEQUENCE: 51
```

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Ser Asp Tyr
            20                  25                  30

Phe Met Lys Trp Val Lys Gln Ser His Gly Lys Arg Leu Glu Trp Ile
        35                  40                  45

Gly Asp Ile Asn Pro Asn Asn Gly Glu Thr Phe Tyr Asn His His Phe
    50                  55                  60

Lys Gly Lys Ala Thr Leu Thr Ile Asp Lys Ser Ser Ser Thr Ala Tyr
65                  70                  75                  80

Met Gln Leu Asn Ser Leu Thr Ser Asp Asp Ser Ala Val Tyr Tyr Cys
                85                  90                  95

Ala Arg Pro Arg Arg Gly Asn Ala Met Asp Phe Trp Gly Gln Gly Thr
            100                 105                 110

Ser Val Thr Val Ser Ser
        115

```
<210> SEQ ID NO 52
<211> LENGTH: 10
<212> TYPE: PRT
<213> ORGANISM: Mus musculus

<400> SEQUENCE: 52
```

Gly Tyr Thr Phe Ser Asp Tyr Phe Met Lys
1               5                   10

```
<210> SEQ ID NO 53
<211> LENGTH: 17
<212> TYPE: PRT
<213> ORGANISM: Mus musculus

<400> SEQUENCE: 53
```

Asp Ile Asn Pro Asn Asn Gly Glu Thr Phe Tyr Asn His His Phe Lys
1               5                   10                  15

Gly

```
<210> SEQ ID NO 54
<211> LENGTH: 9
<212> TYPE: PRT
<213> ORGANISM: Mus musculus

<400> SEQUENCE: 54
```

Pro Arg Arg Gly Asn Ala Met Asp Phe
1               5

```
<210> SEQ ID NO 55
<211> LENGTH: 447
<212> TYPE: PRT
<213> ORGANISM: Artificial Sequence
<220> FEATURE:
```

<223> OTHER INFORMATION: SYNTHETIC CONSTRUCT

<400> SEQUENCE: 55

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Ser Asp Tyr
            20                  25                  30

Phe Met Lys Trp Val Lys Gln Ser His Gly Lys Arg Leu Glu Trp Ile
        35                  40                  45

Gly Asp Ile Asn Pro Asn Asn Gly Glu Thr Phe Tyr Asn His His Phe
    50                  55                  60

Lys Gly Lys Ala Thr Leu Thr Ile Asp Lys Ser Ser Thr Ala Tyr
65                  70                  75                  80

Met Gln Leu Asn Ser Leu Thr Ser Asp Asp Ser Ala Val Tyr Tyr Cys
                85                  90                  95

Ala Arg Pro Arg Arg Gly Asn Ala Met Asp Phe Trp Gly Gln Gly Thr
                100                 105                 110

Ser Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
                180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Arg Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Leu Leu Gln Gly Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400
```

-continued

Ser Asp Gly Ser Phe Phe Leu Tyr Ser Lys Leu Thr Val Asp Lys Ser
              405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly
        435                 440                 445

<210> SEQ ID NO 56
<211> LENGTH: 339
<212> TYPE: DNA
<213> ORGANISM: Mus musculus

<400> SEQUENCE: 56
gacattgtga tgacacagtc tccatcctcc ctggctatgt cagtaggaca gaaggtcacc      60
atgagctgca gtccagtca gagcctttta aatagaggca atcaaaagaa ctatttggcc     120
tggtaccagc agaaaccagg acagtctcct aaatttctgg tatattttgc atccactagg    180
gaatctgggg tccctgatcg cttcataggc agtggatctg ggacagattt cactcttacc    240
atcagcagtg tgcaggctga agacctggca gattattttt gtcagcaaca ttatagtatt    300
ccgtacacgt tcggaggggg gaccaagctg gaaatacaa                           339

<210> SEQ ID NO 57
<211> LENGTH: 113
<212> TYPE: PRT
<213> ORGANISM: Mus musculus

<400> SEQUENCE: 57

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Arg
            20                  25                  30

Gly Asn Gln Lys Asn Tyr Leu Ala Trp Tyr Gln Gln Lys Pro Gly Gln
        35                  40                  45

Ser Pro Lys Phe Leu Val Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Ile Pro Tyr Thr Phe Gly Gly Gly Thr Lys Leu Glu Ile
            100                 105                 110

Gln

<210> SEQ ID NO 58
<211> LENGTH: 17
<212> TYPE: PRT
<213> ORGANISM: Mus musculus

<400> SEQUENCE: 58

Lys Ser Ser Gln Ser Leu Leu Asn Arg Gly Asn Gln Lys Asn Tyr Leu
1               5                   10                  15

Ala

<210> SEQ ID NO 59
<211> LENGTH: 7
<212> TYPE: PRT
<213> ORGANISM: Mus musculus

```
<400> SEQUENCE: 59

Phe Ala Ser Thr Arg Glu Ser
1               5

<210> SEQ ID NO 60
<211> LENGTH: 9
<212> TYPE: PRT
<213> ORGANISM: Mus musculus

<400> SEQUENCE: 60

Gln Gln His Tyr Ser Ile Pro Tyr Thr
1               5

<210> SEQ ID NO 61
<211> LENGTH: 10
<212> TYPE: PRT
<213> ORGANISM: Mus musculus

<400> SEQUENCE: 61

Phe Gly Gly Gly Thr Lys Leu Glu Ile Gln
1               5                   10

<210> SEQ ID NO 62
<211> LENGTH: 220
<212> TYPE: PRT
<213> ORGANISM: Artificial Sequence
<220> FEATURE:
<223> OTHER INFORMATION: SYNTHETIC CONSTRUCT

<400> SEQUENCE: 62

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Arg
            20                  25                  30

Gly Asn Gln Lys Asn Tyr Leu Ala Trp Tyr Gln Gln Lys Pro Gly Gln
        35                  40                  45

Ser Pro Lys Phe Leu Val Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Ile Pro Tyr Thr Phe Gly Gly Gly Thr Lys Leu Glu Ile
            100                 105                 110

Gln Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 63
<211> LENGTH: 369
<212> TYPE: DNA
<213> ORGANISM: Mus musculus

<400> SEQUENCE: 63
gaagtacagc tgcagcagtc tgggcccgag cttcggagac ctgggacctc agtcaagctg    60
tcttgtaagg cttctggcta cagtattaca gatttcctta tgtactgggt aaaacatagg   120
ccagaatacg gcctggaatg gattggatgg attgatcctg aggatggtga acaaaatat    180 gctcagaagt tccaaagcaa ggcccgactg actgcagata cgtcctccaa aacagcctac   240
atggaactca gcagcctgac gtctgaggac acagcaacct attttttgtgc tagatggggc   300 tatatcacgg attatttcta tggcgggttt acttactggg gccgaggcac tctggtcact   360
gtctcttca                                                            369

<210> SEQ ID NO 64
<211> LENGTH: 123
<212> TYPE: PRT
<213> ORGANISM: Mus musculus

<400> SEQUENCE: 64

Glu Val Gln Leu Gln Gln Ser Gly Pro Glu Leu Arg Arg Pro Gly Thr
1               5                   10                  15

Ser Val Lys Leu Ser Cys Lys Ala Ser Gly Tyr Ser Ile Thr Asp Phe
            20                  25                  30

Leu Met Tyr Trp Val Lys His Arg Pro Glu Tyr Gly Leu Glu Trp Ile
        35                  40                  45

Gly Trp Ile Asp Pro Glu Asp Gly Glu Thr Lys Tyr Ala Gln Lys Phe
    50                  55                  60

Gln Ser Lys Ala Arg Leu Thr Ala Asp Thr Ser Ser Lys Thr Ala Tyr
65                  70                  75                  80

Met Glu Leu Ser Ser Leu Thr Ser Glu Asp Thr Ala Thr Tyr Phe Cys
                85                  90                  95

Ala Arg Trp Gly Tyr Ile Thr Asp Tyr Phe Tyr Gly Gly Phe Thr Tyr
            100                 105                 110

Trp Gly Arg Gly Thr Leu Val Thr Val Ser Ser
        115                 120

<210> SEQ ID NO 65
<211> LENGTH: 10
<212> TYPE: PRT
<213> ORGANISM: Mus musculus

<400> SEQUENCE: 65

Gly Tyr Ser Ile Thr Asp Phe Leu Met Tyr
1               5                   10

<210> SEQ ID NO 66
<211> LENGTH: 17
<212> TYPE: PRT
<213> ORGANISM: Mus musculus

<400> SEQUENCE: 66

Trp Ile Asp Pro Glu Asp Gly Glu Thr Lys Tyr Ala Gln Lys Phe Gln
1               5                   10                  15

Ser

```
<210> SEQ ID NO 67
<211> LENGTH: 14
<212> TYPE: PRT
<213> ORGANISM: Mus musculus

<400> SEQUENCE: 67

Trp Gly Tyr Ile Thr Asp Tyr Phe Tyr Gly Gly Phe Thr Tyr
1               5                   10

<210> SEQ ID NO 68
<211> LENGTH: 11
<212> TYPE: PRT
<213> ORGANISM: Mus musculus

<400> SEQUENCE: 68

Trp Gly Arg Gly Thr Leu Val Thr Val Ser Ser
1               5                   10

<210> SEQ ID NO 69
<211> LENGTH: 454
<212> TYPE: PRT
<213> ORGANISM: Artificial Sequence
<220> FEATURE:
<223> OTHER INFORMATION: SYNTHETIC CONSTRUCT

<400> SEQUENCE: 69

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Thr Asp Phe
                20                  25                  30

Leu Met Tyr Trp Val Arg Gln Ala Pro Gly Lys Gly Leu Glu Trp Val
            35                  40                  45

Ala Trp Ile Asp Pro Glu Asp Gly Glu Thr Lys Tyr Ala Gln Lys Phe
        50                  55                  60

Gln Ser Lys Ala Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Trp Gly Tyr Ile Thr Asp Tyr Phe Tyr Gly Gly Phe
            100                 105                 110

Thr Tyr Trp Gly Arg Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Arg Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255
```

-continued

```
Asp Thr Leu Met Ile Ser Arg Thr Pro Glu Val Thr Cys Val Val
            260                 265                 270
Asp Val Ser His Glu Asp Pro Glu Val Lys Phe Asn Trp Tyr Val Asp
        275                 280                 285
Gly Val Glu Val His Asn Ala Lys Thr Lys Pro Arg Glu Leu Leu Gln
    290                 295                 300
Gly Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Ala Leu
                325                 330                 335
Pro Ala Pro Ile Glu Lys Thr Ile Ser Lys Ala Lys Gly Gln Pro Arg
            340                 345                 350
Glu Pro Gln Val Tyr Thr Leu Pro Pro Ser Arg Glu Glu Met Thr Lys
        355                 360                 365
Asn Gln Val Ser Leu Thr Cys Leu Val Lys Gly Phe Tyr Pro Ser Asp
    370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
            420                 425                 430
Cys Ser Val Met His Glu Ala Leu His Asn His Tyr Thr Gln Lys Ser
        435                 440                 445
Leu Ser Leu Ser Pro Gly
    450

<210> SEQ ID NO 70
<211> LENGTH: 318
<212> TYPE: DNA
<213> ORGANISM: Mus musculus

<400> SEQUENCE: 70
gacatccaga tgacccagtc tcctccagtc ctgtctgcat ctgtgggaga cagagtcact    60
ctcagctgca aagcaagtca gaatattaat aagaacttag actggtatca gcaaaagcat   120
ggagaagctc caaaactcct gatatatcat acaaacactt tgcaaatggg catcccatca   180
aggttcagtg gcagtggatc tggtacagat tacgcactca ccatcaccag cctgcagcct   240
gaagatgttg ccacatatta ctgctatcaa tataacagtg ggcccacgtt tggagctggg   300
accaagctgg aactgaga                                                 318

<210> SEQ ID NO 71
<211> LENGTH: 106
<212> TYPE: PRT
<213> ORGANISM: Mus musculus

<400> SEQUENCE: 71

Asp Ile Gln Met Thr Gln Ser Pro Pro Val Leu Ser Ala Ser Val Gly
1               5                   10                  15
Asp Arg Val Thr Leu Ser Cys Lys Ala Ser Gln Asn Ile Asn Lys Asn
            20                  25                  30
Leu Asp Trp Tyr Gln Gln Lys His Gly Glu Ala Pro Lys Leu Leu Ile
        35                  40                  45
Tyr His Thr Asn Thr Leu Gln Met Gly Ile Pro Ser Arg Phe Ser Gly
    50                  55                  60
```

Ser Gly Ser Gly Thr Asp Tyr Ala Leu Thr Ile Thr Ser Leu Gln Pro
65                  70                  75                  80

Glu Asp Val Ala Thr Tyr Tyr Cys Tyr Gln Tyr Asn Ser Gly Pro Thr
                85                  90                  95

Phe Gly Ala Gly Thr Lys Leu Glu Leu Arg
            100                 105

<210> SEQ ID NO 72
<211> LENGTH: 11
<212> TYPE: PRT
<213> ORGANISM: Mus musculus

<400> SEQUENCE: 72

Lys Ala Ser Gln Asn Ile Asn Lys Asn Leu Asp
1               5                   10

<210> SEQ ID NO 73
<211> LENGTH: 7
<212> TYPE: PRT
<213> ORGANISM: Mus musculus

<400> SEQUENCE: 73

His Thr Asn Thr Leu Gln Met
1               5

<210> SEQ ID NO 74
<211> LENGTH: 8
<212> TYPE: PRT
<213> ORGANISM: Mus musculus

<400> SEQUENCE: 74

Tyr Gln Tyr Asn Ser Gly Pro Thr
1               5

<210> SEQ ID NO 75
<211> LENGTH: 10
<212> TYPE: PRT
<213> ORGANISM: Mus musculus

<400> SEQUENCE: 75

Phe Gly Ala Gly Thr Lys Leu Glu Leu Arg
1               5                   10

<210> SEQ ID NO 76
<211> LENGTH: 213
<212> TYPE: PRT
<213> ORGANISM: Artificial Sequence
<220> FEATURE:
<223> OTHER INFORMATION: SYNTHETIC CONSTRUCT

<400> SEQUENCE: 76

Asp Ile Gln Met Thr Gln Ser Pro Pro Val Leu Ser Ala Ser Val Gly
1               5                   10                  15

Asp Arg Val Thr Leu Ser Cys Lys Ala Ser Gln Asn Ile Asn Lys Asn
                20                  25                  30

Leu Asp Trp Tyr Gln Gln Lys His Gly Glu Ala Pro Lys Leu Leu Ile
            35                  40                  45

Tyr His Thr Asn Thr Leu Gln Met Gly Ile Pro Ser Arg Phe Ser Gly
        50                  55                  60

Ser Gly Ser Gly Thr Asp Tyr Ala Leu Thr Ile Thr Ser Leu Gln Pro
65                  70                  75                  80

Glu Asp Val Ala Thr Tyr Tyr Cys Tyr Gln Tyr Asn Ser Gly Pro Thr

```
                    85                  90                  95
Phe Gly Ala Gly Thr Lys Leu Glu Leu Arg Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 77
<211> LENGTH: 9
<212> TYPE: PRT
<213> ORGANISM: Artificial Sequence
<220> FEATURE:
<223> OTHER INFORMATION: SYNTHETIC CONSTRUCT

<400> SEQUENCE: 77

Gln Leu Gln Gly Leu Leu Gln Gly Gly
1               5

<210> SEQ ID NO 78
<211> LENGTH: 4
<212> TYPE: PRT
<213> ORGANISM: Artificial Sequence
<220> FEATURE:
<223> OTHER INFORMATION: SYNTHETIC CONSTRUCT

<400> SEQUENCE: 78

Leu Leu Gln Gly
1

<210> SEQ ID NO 79
<211> LENGTH: 6
<212> TYPE: PRT
<213> ORGANISM: Artificial Sequence
<220> FEATURE:
<223> OTHER INFORMATION: SYNTHETIC CONSTRUCT

<400> SEQUENCE: 79

Leu Ser Leu Ser Gln Gly
1               5

<210> SEQ ID NO 80
<211> LENGTH: 8
<212> TYPE: PRT
<213> ORGANISM: Artificial Sequence
<220> FEATURE:
<223> OTHER INFORMATION: SYNTHETIC CONSTRUCT

<400> SEQUENCE: 80

Gly Gly Gly Leu Leu Gln Gly Gly
1               5
```

```
<210> SEQ ID NO 81
<211> LENGTH: 5
<212> TYPE: PRT
<213> ORGANISM: Artificial Sequence
<220> FEATURE:
<223> OTHER INFORMATION: SYNTHETIC CONTRUCT

<400> SEQUENCE: 81

Gly Leu Leu Gln Gly
1               5

<210> SEQ ID NO 82
<211> LENGTH: 13
<212> TYPE: PRT
<213> ORGANISM: Artificial Sequence
<220> FEATURE:
<223> OTHER INFORMATION: SYNTHETIC CONSTRUCT

<400> SEQUENCE: 82

Leu Leu Gln Gly Ser Pro Leu Ala Gln Ser His Gly Gly
1               5                   10

<210> SEQ ID NO 83
<211> LENGTH: 7
<212> TYPE: PRT
<213> ORGANISM: Artificial Sequence
<220> FEATURE:
<223> OTHER INFORMATION: SYNTHETIC CONSTRUCT

<400> SEQUENCE: 83

Gly Leu Leu Gln Gly Gly Gly
1               5

<210> SEQ ID NO 84
<211> LENGTH: 6
<212> TYPE: PRT
<213> ORGANISM: Artificial Sequence
<220> FEATURE:
<223> OTHER INFORMATION: SYNTHETIC CONSTRUCT

<400> SEQUENCE: 84

Gly Leu Leu Gln Gly Gly
1               5

<210> SEQ ID NO 85
<211> LENGTH: 4
<212> TYPE: PRT
<213> ORGANISM: Artificial Sequence
<220> FEATURE:
<223> OTHER INFORMATION: SYNTHETIC CONSTRUCT

<400> SEQUENCE: 85

Gly Leu Leu Gln
1

<210> SEQ ID NO 86
<211> LENGTH: 8
<212> TYPE: PRT
<213> ORGANISM: Artificial Sequence
<220> FEATURE:
<223> OTHER INFORMATION: SYNTHETIC CONSTRUCT

<400> SEQUENCE: 86

Leu Leu Gln Leu Leu Gln Gly Ala
1               5

<210> SEQ ID NO 87
```

```
<211> LENGTH: 5
<212> TYPE: PRT
<213> ORGANISM: Artificial Sequence
<220> FEATURE:
<223> OTHER INFORMATION: SYNTHETIC CONSTRUCT

<400> SEQUENCE: 87

Leu Leu Gln Gly Ala
1               5

<210> SEQ ID NO 88
<211> LENGTH: 7
<212> TYPE: PRT
<213> ORGANISM: Artificial Sequence
<220> FEATURE:
<223> OTHER INFORMATION: SYNTHETIC CONSTRUCT

<400> SEQUENCE: 88

Leu Leu Gln Tyr Gln Gly Ala
1               5

<210> SEQ ID NO 89
<211> LENGTH: 6
<212> TYPE: PRT
<213> ORGANISM: Artificial Sequence
<220> FEATURE:
<223> OTHER INFORMATION: SYNTHETIC CONSTRUCT

<400> SEQUENCE: 89

Leu Leu Gln Gly Ser Gly
1               5

<210> SEQ ID NO 90
<211> LENGTH: 6
<212> TYPE: PRT
<213> ORGANISM: Artificial Sequence
<220> FEATURE:
<223> OTHER INFORMATION: SYNTHETIC CONSTRUCT

<400> SEQUENCE: 90

Leu Leu Gln Tyr Gln Gly
1               5

<210> SEQ ID NO 91
<211> LENGTH: 7
<212> TYPE: PRT
<213> ORGANISM: Artificial Sequence
<220> FEATURE:
<223> OTHER INFORMATION: SYNTHETIC CONSTRUCT

<400> SEQUENCE: 91

Leu Leu Gln Leu Leu Gln Gly
1               5

<210> SEQ ID NO 92
<211> LENGTH: 5
<212> TYPE: PRT
<213> ORGANISM: Artificial Sequence
<220> FEATURE:
<223> OTHER INFORMATION: SYNTHETIC CONSTRUCT

<400> SEQUENCE: 92

Ser Leu Leu Gln Gly
1               5

<210> SEQ ID NO 93
<211> LENGTH: 5
```

```
<212> TYPE: PRT
<213> ORGANISM: Artificial Sequence
<220> FEATURE:
<223> OTHER INFORMATION: SYNTHETIC CONSTRUCT

<400> SEQUENCE: 93

Leu Leu Gln Leu Gln
1               5

<210> SEQ ID NO 94
<211> LENGTH: 6
<212> TYPE: PRT
<213> ORGANISM: Artificial Sequence
<220> FEATURE:
<223> OTHER INFORMATION: SYNTHETIC CONSTRUCT

<400> SEQUENCE: 94

Leu Leu Gln Leu Leu Gln
1               5

<210> SEQ ID NO 95
<211> LENGTH: 5
<212> TYPE: PRT
<213> ORGANISM: Artificial Sequence
<220> FEATURE:
<223> OTHER INFORMATION: SYNTHETIC CONSTRUCT

<400> SEQUENCE: 95

Leu Leu Gln Gly Arg
1               5

<210> SEQ ID NO 96
<211> LENGTH: 6
<212> TYPE: PRT
<213> ORGANISM: Artificial Sequence
<220> FEATURE:
<223> OTHER INFORMATION: SYNTHETIC CONSTRUCT

<400> SEQUENCE: 96

Leu Leu Gln Gly Pro Pro
1               5

<210> SEQ ID NO 97
<211> LENGTH: 6
<212> TYPE: PRT
<213> ORGANISM: Artificial Sequence
<220> FEATURE:
<223> OTHER INFORMATION: SYNTHETIC CONSTRUCT

<400> SEQUENCE: 97

Leu Leu Gln Gly Pro Ala
1               5

<210> SEQ ID NO 98
<211> LENGTH: 8
<212> TYPE: PRT
<213> ORGANISM: Artificial Sequence
<220> FEATURE:
<223> OTHER INFORMATION: SYNTHETIC CONSTRUCT

<400> SEQUENCE: 98

Gly Gly Leu Leu Gln Gly Pro Pro
1               5

<210> SEQ ID NO 99
<211> LENGTH: 7
<212> TYPE: PRT
```

```
<213> ORGANISM: Artificial Sequence
<220> FEATURE:
<223> OTHER INFORMATION: SYNTHETIC CONSTRUCT

<400> SEQUENCE: 99

Gly Gly Leu Leu Gln Gly Ala
1               5

<210> SEQ ID NO 100
<211> LENGTH: 7
<212> TYPE: PRT
<213> ORGANISM: Artificial Sequence
<220> FEATURE:
<223> OTHER INFORMATION: SYNTHETIC CONSTRUCT

<400> SEQUENCE: 100

Leu Leu Gln Gly Pro Gly Lys
1               5

<210> SEQ ID NO 101
<211> LENGTH: 6
<212> TYPE: PRT
<213> ORGANISM: Artificial Sequence
<220> FEATURE:
<223> OTHER INFORMATION: SYNTHETIC CONSTRUCT

<400> SEQUENCE: 101

Leu Leu Gln Gly Pro Gly
1               5

<210> SEQ ID NO 102
<211> LENGTH: 5
<212> TYPE: PRT
<213> ORGANISM: Artificial Sequence
<220> FEATURE:
<223> OTHER INFORMATION: SYNTHETIC CONSTRUCT

<400> SEQUENCE: 102

Leu Leu Gln Gly Pro
1               5

<210> SEQ ID NO 103
<211> LENGTH: 4
<212> TYPE: PRT
<213> ORGANISM: Artificial Sequence
<220> FEATURE:
<223> OTHER INFORMATION: SYNTHETIC CONSTRUCT

<400> SEQUENCE: 103

Leu Leu Gln Pro
1

<210> SEQ ID NO 104
<211> LENGTH: 6
<212> TYPE: PRT
<213> ORGANISM: Artificial Sequence
<220> FEATURE:
<223> OTHER INFORMATION: SYNTHETIC CONSTRUCT

<400> SEQUENCE: 104

Leu Leu Gln Pro Gly Lys
1               5

<210> SEQ ID NO 105
<211> LENGTH: 7
<212> TYPE: PRT
<213> ORGANISM: Artificial Sequence
```

```
<220> FEATURE:
<223> OTHER INFORMATION: SYNTHETIC CONSTRUCT

<400> SEQUENCE: 105

Leu Leu Gln Ala Pro Gly Lys
1               5

<210> SEQ ID NO 106
<211> LENGTH: 7
<212> TYPE: PRT
<213> ORGANISM: Artificial Sequence
<220> FEATURE:
<223> OTHER INFORMATION: SYNTHETIC CONSTRUCT

<400> SEQUENCE: 106

Leu Leu Gln Gly Ala Pro Gly
1               5

<210> SEQ ID NO 107
<211> LENGTH: 6
<212> TYPE: PRT
<213> ORGANISM: Artificial Sequence
<220> FEATURE:
<223> OTHER INFORMATION: SYNTHETIC CONSTRUCT

<400> SEQUENCE: 107

Leu Leu Gln Gly Ala Pro
1               5

<210> SEQ ID NO 108
<211> LENGTH: 6
<212> TYPE: PRT
<213> ORGANISM: Artificial Sequence
<220> FEATURE:
<223> OTHER INFORMATION: SYNTHETIC CONSTRUCT

<400> SEQUENCE: 108

Leu Leu Gln Leu Gln Gly
1               5
```